US009719064B2

(12) United States Patent
Selber et al.

(10) Patent No.: US 9,719,064 B2
(45) Date of Patent: Aug. 1, 2017

(54) GENOMICS OF ACTINOPLANES UTAHENSIS

(75) Inventors: Klaus Selber, Haan (DE); Bernhard Weingaertner, Wülfrath (DE); Hermann Wehlmann, Wuppertal (DE); Winfried Rosen, Remscheid (DE); Alfred Pühler, Bielefeld (DE); Patrick Schwientek, Bielefeld (DE); Jörn Kalinowski, Bielefeld (DE); Udo Wehmeier, Wuppertal (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 191 days.

(21) Appl. No.: 13/814,235

(22) PCT Filed: Aug. 1, 2011

(86) PCT No.: PCT/EP2011/063243
§ 371 (c)(1),
(2), (4) Date: Jun. 13, 2013

(87) PCT Pub. No.: WO2012/016960
PCT Pub. Date: Feb. 9, 2012

(65) Prior Publication Data
US 2013/0302855 A1 Nov. 14, 2013

(30) Foreign Application Priority Data
Aug. 4, 2010 (EP) .................................... 10171831

(51) Int. Cl.
*C12N 1/20* (2006.01)
*C07K 14/365* (2006.01)
*C12P 19/26* (2006.01)

(52) U.S. Cl.
CPC .............. *C12N 1/20* (2013.01); *C07K 14/365* (2013.01); *C12P 19/26* (2013.01)

(58) Field of Classification Search
None
See application file for complete search history.

(56) References Cited

FOREIGN PATENT DOCUMENTS

| CA | 2282735 A1 | * | 3/1998 |
| CA | 2 282 735 A1 | | 9/1998 |
| DE | 10021667 A1 | | 11/2001 |
| EP | 1852508 A2 | * | 11/2007 |
| WO | 98/38313 A1 | | 9/1998 |

OTHER PUBLICATIONS

Altschu et al., "Basic Local Alignment Search Tool," Journal of Molecular Biology, 1990, 215:403-410.
Badger et al., "CRITICA: Coding Region Identification Tool Invoking Comparative Analysis," J. Mol. Evol., 1999, 512-524 (Downloaded from http://mbe.oxfordjournals.org/ by guest on May 30, 2013).
Bendtsen et al., "Non-classical protein secretion in bacteria," BMC Microbiology, 2005, 5:58.
Bendtsen et al., "Improved Prediction of Signal Peptides: SignalP 3.0," Journal of Molecular Biology, 2004, 340:783-795.
Caspary et al., "Inhibition of Human Intestinal α-Glucosidehydrolases by a New Complex Oligosaccharide," Research in Experimental Medicine (Berl.) 1979, 175:1-6.
Couch, J. N., "Some New Genera and Species of the Actinoplanaceae," The Journal of the Mitchell Society,1963, 79:53-70 (Kopie von subito e.V., geliefert für Bayer Business Services GmbH BBS-PTS-IC-LS (DTL9900221).
Coulson, A., "High-performance searching of biosequence databases," Trends in Biotechnology, Mar. 1994, 12:76-80.
Delcher et al., "Improved microbial gene identification with GLIMMER," Nucleic Acids Research, 1999, 27(23):4636-4641.
Gordon et al., "Consed: A Graphical Tool for Sequence Finishing," Genome Research, 1998, 8:195-202.
Krogh et al., "Predicting Transmembrane Protein Topology with a Hidden Markov Model: Application to Complete Genomes," Journal of Molecular Biology, 2001, 305:567-580.
Lee et al., "Three trehalose synthetic pathways in the acarbose-producing *Actinoplanes* sp. SN223/29 and evidence for the TreY role in biosynthesis of component C," Appl. Microbiol. Biotechnol., 2008, 80:767-778.
McHardy et al., "Development of joint application strategies for two microbial gene finders," Bioinformatics, 2004, 20(10)1622-1631 (Downloaded from http://bioinformatics.oxfordjournals.org/ by guest on May 30, 2013).
Nielsen et al., "Identification of prokaryotic and eukaryotic signal pep tides and prediction of their cleavage sites," Protein Engineering, 1997, 10(1):1-6.
Salgado et al., "Operons in *Escherichia coli*: Genomic analyses and predictions," Proceeding of the National Academy of Sciences, Jun. 6, 2000, 97(12):6652-6657.
Sanger et al., "A Rapid Method for Determining Sequences in DNA by Primed Synthesis with DNA Polymerase," Journal of Molecular Biology, 1975, 94:441-448.
Schmidt et al., "α-Glucosidase Inhibitors New Complex Oligosaccharides of Microbial Origin," Naturwissenschaften, 1977, 64:535-536.
Sonnhammer et al., "A hidden Markov model for predicting transmembrane helices in protein sequences," Proceedings of ISMB 6, 1998, 175-182.

(Continued)

*Primary Examiner* — Paul Holland
(74) *Attorney, Agent, or Firm* — Morrison & Foerster LLP

(57) ABSTRACT

The present invention describes the DNA-sequence of the wild type genome as well as all genetic modifications which were introduced into the wild type—and further developed strains, based thereon. Thereby the first genotypic characterization of the developed strains, including the latest production strain, has been accomplished, accounting for the major part of the invention. Furthermore, on the basis of the determined DNA-sequences, potential genes were identified and account, combined with their functional annotation, for another part of the invention. In particular, the gene- and DNA-sequences, as well as protein-sequences derived there out, contribute to the invention which were affected by mutagenic modifications throughout the strain development process, potentially contributing to the increased production yield.

3 Claims, 3 Drawing Sheets

(56) References Cited

OTHER PUBLICATIONS

Figure 1:
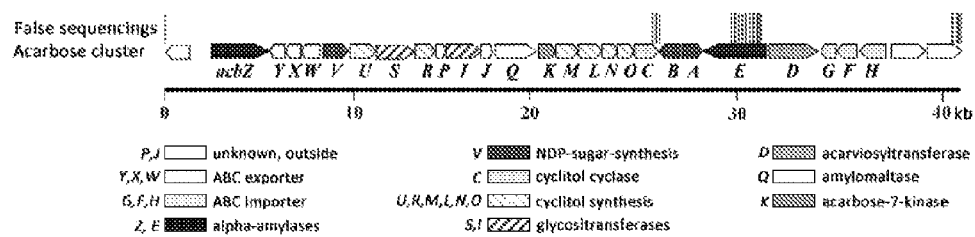

Steffen et al., "RNAshapes: an integrated RNA analysis package based on abstract shapes," Bioinformatics, 2006, 22(4):500-503 (Downloaded from http://bioinformatics.oxfordjournals.org/ by guest on May 30, 2013).

Tatusov et al., "The COG database: new developments in phylogenetic classification of proteins from complete genomes," Nucleic Acids Research, 2001, 29(1):22-28.

Tatusov et al., "A Genomic Perspective on Protein Families," Science, Oct. 24, 1997, 278:631-637 (Downloaded from www.sciencemag.org on May 30, 2013).

Ventura et al., "Genomics of Actinobacteria: Tracing the Evolutionary History of an Ancient Phylum," Microbiology and Molecular Biology Reviews, Sep. 2007, 71(3):495-548.

Wehmeier et al., "Biotechnology and molecular biology of the α-glucosidase inhibitor acarbose," Appl. Microbiol. Biotechnol. 2004, 63:613-625.

Wehmeier, U. F., "The Biosynthesis and Metabolism of *Acarbose Actinoplanes* sp. SE 50/110: A Progress Report," Biocatalysis and Biotransformation, 2003, 21(415):279-284.

Meyer et al., "GenDB-,an open source genome annotation system for prokaryote genomes," Nucleic Acids Research, 2003, 31(8):2187-2195.

Christian et al. "Targeting double-Strand Breaks with TAL Effector Nucleases", Genetics, 2010, 186(2): 757-761.

Frommer et al., "New Enzyme Inhibitors from Microorganisms," Planta Medica Journal of Medicinal Plant Research,1979, 35(3):195-217 (German article with English Abstract).

Hyum et al., "Molecular Detection of α-Glucosidase Inhibitor-producing Actinomycetes," Journal of Microbiology, 2005, 43(3):313-318.

\* cited by examiner

GENOMICS OF ACTINOPLANES UTAHENSIS

DESCRIPTION OF THE INVENTION

The gram-positive prokaryote *Actinoplanes utahensis* was described for the first time by John Couch in 1963 (Couch, J. N., Elisha Mitchell Sci. Soc., 1963, 79:53-70). Thereafter, in the year 1977, acarbose and its homologues were first found in the supernatant of an *Actinoplanes utahensis* culture (Schmidt et al., Naturwissenschaften, 1977, 64:535-536). Two years later, the medical effect of acarbose as an α-glucosidase-inhibitor within the human intestine was discovered (Caspary et al., Res. Exp. Med., 1979, 175:1-6) and within the same year, its potential application for the treatment of type-2 diabetes mellitus was propagated (Frommer et al., J. Med. Plant Res., 1979, 35:195-217).

Since 1990 the α-glucosidase-inhibitor acarbose is produced and marketed for the treatment of type-2 diabetes mellitus. Starting from the *A. utahensis* wild type strain the production has been continuously improved with regard to an ever increasing acarbose yield by optimization of the fermentation process as well as the production strain itself. The strain development has been driven by a multitude of mutagenesis experiments, which are primarily responsible for the raising acarbose production.

The genetic modifications in the organism, triggered by the mutagenesis experiments have so far only been recognizable by phenotypic characteristics (e.g. the increase of acarbose yield). More precisely, the genetic bases for the raising production yields have, until now, been completely unknown. However, this knowledge is of fundamental interest for the understanding of the mechanisms, leading to the rise in production. Furthermore it forms the most important prerequisite for the process of further, targeted genetic modification of the organism, optimizing *A. utahensis* to an even greater extend.

The present invention describes the DNA-sequence of the wild type genome as well as all genetic modifications which were introduced into the wild type- and further developed strains, based thereon. Thereby the first genotypic characterization of the developed strains, including the latest production strain, has been accomplished, accounting for the major part of the invention. Furthermore, on the basis of the determined DNA-sequences, potential genes were identified and account, combined with their functional annotation, for another part of the invention. In particular, the gene- and DNA-sequences, as well as protein-sequences derived there out which were affected by mutagenic modifications throughout the strain development process, potentially contributing to the increased production yield, contribute to the invention.

Material and Methods

As briefly described above, a series of mutagenesis experiments has been performed on the *Actinoplanes utahensis* wild type strain SE50-100, originally isolated from a soil sample. These experiments were aimed at the identification of mutants with an improved production of acarbose as well as other parameters, relevant for industrial production by fermentation such as high growth rate, optimized nutrient needs and consumption as well as low formation of cumbersome byproducts. Initially based on the wild type strain, further mutagenesis experiments were continuously performed on the mutant strains selected from the previous experiments. During the course of the strain development, several mutants with outstanding attributes were selected as new production strains and transferred into large scale production. Of these, seven strains were selected, including the latest production strain as well as the wild type strain, to be sequenced by Bielefeld University's Center for Biotechnology (CeBiTec) Universitätsstrasse 27, 33615 Bielefeld, Germany. Table 1 lists all seven strains that have been used during this project in the chronological order of their development.

Table 1 list all *A. utahensis* strains used in this study in their chronological order.

| Strain Symbol | Development Order | Remark |
| --- | --- | --- |
| SE50-100 | (1) | wild type strain |
| SN223-29-47 | 2 | |
| C445-P47 | 3 | |
| SN12755-48 | 4 | |
| SC3687-18-43 | 5 | |
| SC7177-40-17 | 6 | |
| SN19910-37-21 | 7 | latest production strain |

Strain Cultivation

Cultivation of strains in order to check their acarbose productivity was done as described previously (Schmidt et al., Naturwissenschaften, 1977, 64:535-536). In order to isolate DNA, the *Actinoplanes* strains were cultivated in a two-step shake flask system. Beside inorganic salts the medium contained starch hydrolysate as carbon source and yeast extract as nitrogen source. Preculture and main culture were run for 3 days and 4 days, respectively, on a rotary shaker at 28° C. Then the biomass was collected by centrifugation.

Strain Mutagenesis

The strain development of the Acarbose producer was performed by the method of stepwise selection of higher producing strains. This method uses the process of random mutation by chemical or physical means. Chemicals used to induce mutations were either alkylating agents or intercalating dyes that serve as frameshift mutagens. Physical treatment of cells to induce mutagenesis was done with UV light of 365 nm. Fragments of the mycelium were used for mutagenesis treatment in appropriate buffer systems. After the treatment the biological material was grown for a short period in liquid medium to allow phenotypic expression of the induced alterations and then plated on agar plates. A random selection of clones that survived the mutagenesis treatment was checked for their acarbose productivity in small scale shake flask experiments. The best mutant clones obtained during a mutation cycle of this kind were chosen for the next mutation step. Several such steps of mutation and selection resulted in a gradual increase of productivity.

Preparation of Genomic DNA

The preparation of genomic DNA of *A. utahensis* strain SE50-110 was performed by a modification of the general described procedure (Maniatis T., Fritsch E. F., Sambrook J., Molecular Cloning—A Laboratory Manual, Cold Spring Harbor Press, 1982). The mycel of 50 mL of freshly grown culture was harvested by centrifugation (10 min., 4.000 rpm, 4° C.) in a Christ centrifuge. The pellet was washed 4 times in a buffer containing 15% sucrose (Merck KGaA, Darmstadt, Germany, cat. 7651), 25 mM TrisHCl pH 7.2 (Merck KGaA, Darmstadt, Germany, cat. 1.08382.1000), and 25 mM EDTA (Merck KGaA, Darmstadt, Germany, cat. 8418) under the same conditions. Finally the pellet was resuspended in 4.5 mL of the same buffer and lysozyme (Merck KGaA, Darmstadt, Germany, cat. 1.05281.0010) and RNAse (Qiagen, Hilden, Germany, cat. 19101) were added to final concentrations of 5 mg/mL and 50 µg/mL respectively and the mixture was incubated at 37° C. for 45 minutes. After the addition of SDS (Serva, Heidelberg, Germany, cat. 20767) and proteinase K (Qiagen, Hilden, Germany, cat. 19133) to 0.5% and 2 μg/mL final concentrations respectively, the incubation was continued at 50° C. for 5 minutes. NaCl (Merck KGaA, Darmstadt, Germany, cat. 1.06404.1000) was added to a final concentration of 300 mM and the volume adjusted with WFI to 8 mL. The lysate was subjected to three successive phenol/SEVAG extractions (SEVAG is a mixture of 24 parts chloroform [Merck KGaA, Darmstadt, Germany, cat. 1.02445.1000] and 1 part isoamylalcohol [Merck KGaA, Darmstadt, Germany, cat. 1.979.1000]) and the phenol was removed by washing the DNA solution with 10 mL SEVAG. The DNA was precipitated by the addition of 0.1 volume of 3 M sodium acetate (pH 4.8) (Merck KGaA, Darmstadt, Germany, cat. 6268) and 1 volume of cold isopropanol (Merck KGaA, Darmstadt, Germany, cat. 1.09634.1011). The DNA was pelleted by centrifugation (25 minutes, 4.000 rpm, 4° C.; Christ centrifuge) and the DNA pellet was washed thoroughly (5×) with 70% ethanol (Merck KGaA, Darmstadt, Germany, cat. 1.00983.1011) (10 minutes, 4000 rpm, 4° C.; Christ centrifuge) and air-dried. Finally the pellet was resuspended in 200 μL Tris pH 8.5 over night at 4° C. and the DNA concentration was determined by measuring the optical density at 260 nm and 280 nm. The size of the prepared DNA was analysed by subjecting an aliquot (10 μL) of the DNA solution to electrophoresis through a 1% agarose gel as quality check.

Fosmid-Library Construction

Fosmids are commonly used for preparing genomic libraries when a smaller insert size is desired. The inserts have an average size of 40 kb and are produced by random shearing, yielding a more uniform coverage of the genome than other library types. Fosmids are excellent candidates for closing gaps in a whole genome sequencing projects due to their uniform coverage. The fosmid-library construction for *Actinoplanes utahensis* wild type has been carried out on genomic DNA by IIT Biotech GmbH, Universitätsstr. 25, 33615 Bielefeld, Germany. For construction in *E. coli* EPI300 cells, the CopyControl™ Cloning System (EPICENTRE Biotechnologies, 726 Post Road, Madison, Wis. 53713, USA) has been used. The kit was obtained from Biozym Scientific GmbH, Steinbrinksweg 27, 31840 Hessisch Oldendorf, Germany.

Fosmid-Library Sequencing

Fosmid-library sequencing for *Actinoplanes utahensis* wild type has been carried out on a 3730xl DNA-Analyzer (Applied Biosystems, 850 Lincoln Centre Drive, Foster City, Calif. 94404, USA) by IIT Biotech GmbH, Universitätsstr. 25, 33615 Bielefeld, Germany. The device performs parallel Sanger-sequencing in 96 capillaries (Sanger et al., J. Mol. Biol., 1975, 94 (3):441-448). The resulting flowgram files were base called and stored in FASTA format. Both files were later used for gap-closure and quality assessment.

High-Throughput Genome Sequencing

Genome Sequencer FLX

The Genome Sequencer FLX (GS FLX) system (454 Life Sciences, 15 Commercial Street, Branford, Conn. 06405, USA) has been used for pyrosequencing of the *A. utahensis* wild type strain SE50-100 as well as the latest production strain SN19910-37-21. Two different protocols and reagent series were used on the GS FLX platform:

1. Standard series with long paired end (PE) protocol. The genome-DNA fragment size for the PE-library construction was 2.5-3.0 kb. The protocol yields an average read length of 2×100 bases and a total number of sequenced bases of about 100 Mb.
2. Titanium series with whole genome shotgun (WGS) protocol. The genome-DNA fragment size for the WGS-library construction was 500-800 bp. The protocol yields a read length of 400-500 bases and a total number of sequenced bases ranging from 400-600 Mb.

Details on the protocols are provided in the manufacturers manuals, namely the *GS FLX Sequencing Method Manual* (December 2007), *GS FLX Paired End DNA Library Preparation Method Manual* (December 2007), *GS FLX Titanium Sequencing Method Manual* (October 2008) and the *GS FLX Titanium General Library Preparation Method Manual* (October 2008)

Genome Analyzer IIx

The Genome Analyzer IIx (GA IIx) system (Illumina, Inc., 9885 Towne Centre Drive, San Diego, Calif. 92121, USA) including Cluster-Station and Paired-End-Module has been used for sequencing-by-synthesis of the five former productions strains SN223-29-47, C445-P47, SN12755-48, SC3687-18-43 and SC7177-40-17. For all five strains, the paired end protocol with a genome-DNA fragment size of approximately 330 bp and a read length of 2×36 bases was used. Library preparation, cluster generation and sequencing were performed according to the manufacturers manuals *Paired-End sequencing Sample Preparation Guide* (Part #1005063 Rev. B September 2009), *Using the Paired-End Cluster Generation Kit v2 on the Cluster Station and Paired-End Module* (Part #1005629 Rev. C February 2009) and *Using SBS Sequencing Kit v3 on the Genome Analyzer* (Part #1005637 Rev. A November 2008).

Wild Type Draft Genome Assembly

The automated assembly of all *Actinoplanes utahensis* wild type reads generated by the GS FLX platform was performed with the Newbler assembler software (gsAssembler version 2.0.00.22, 454 Life Science). For detailed information on the assembly algorithm see the *Genome Sequencer FLX System Software Manual Part C*, version 2.3 (October 2009).

Wild Type Genome Finishing

In order to close remaining gaps between contiguouse sequences (contigs) still present after the automated de novo assembly by the Newbler program, the visual assembly software package Consed (Gordon et al., Genome Research, 1998, 8:195-202) was utilized. Within the graphical user interface, primer pairs at the ends of contiguous contigs were selected. These primer pairs were then used to amplify desired sequences from clones originating from the previously constructed fosmid-library in order to bridge the gaps between contiguous contigs.

After the DNA sequence of these fosmid-reads had been determined, manual assembly of all applicable reads was performed with the aid of different program features. In detail, a fosmid-read is first aligned to the 5' end of a contig, extending it by its 5' remainder. Afterwards, the 3' end of the neighboring contig is aligned to this extension, spanning the previously existing gap and joining the two contigs.

In cases were the length or quality of one fosmid-read was not sufficient to span the gap, multiple rounds of primer selection, sequencing and manual assembly were performed.

Wild Type Genome Annotation

Identification of Coding Sequences (CDS)

The potential genes and partial gene sequences on the wild type genome (see Appendix) were identified by a series of computational analysis. All utilized programs are part of the GenDB annotation-pipeline (Meyer et al., Nucleic Acids Research, 2003, 31(8):2187-95). For the identification of CDSs intrinsic, extrinsic and combined methods were applied in order to achieve optimal results.

The program responsible for the intrinsic prediction of CDSs is Glimmer (Delcher et al., Nucleic Acid Research, 1999, 27:4636-41). It first constructs a training set from CDSs with optimal characteristics taken from the genome to be analyzed. Based upon this set, an interpolated Markov Model is calculated, which is used in the actual search-run to identify all CDSs of the genomic sequence. Glimmer tends to calculate more CDSs as are actually there.

The extrinsic CDS-prediction has been carried out by CRITICA (Badger et al., Mol. Biol. Evol., 1999, 16:512-24). CRITICA first makes use of the BLASTN algorithm (Altschul et al., J. Mol. Biol., 1990, 215(3):403-10) in order to determine a list of genomic sequences which show at least slight similarity to sequences from public DNA-databases. If the translated amino acid sequence possesses a higher similarity than it would be expected based on the DNA-similarities, this is interpreted as evidence for being a conserved coding sequence. CRITICA combines these results with intrinsic analysis based on the distribution of hexa nucleotides to improve the prediction of previously unknown sequences. Despite this, CRITICA still tends to predict fewer CDS in cases where no homolog sequence is already stored in a public database.

The Reganor software (McHardy et al., Bioinformatics, 2004, 20(10):1622-31) has been used to optimize the results calculated by Glimmer and CRITICA. It combines the results of both programs and thus minimizes their respective shortcomings. Moreover, the CDS predicted by CRITICA form the basis of the combined results, complemented by the intrinsic predictions calculated by Glimmer.

Annotation and Functional Prediction

The identified open reading frames were analyzed through a variety of different software packages in order to draw conclusions from their RNA- and/or amino acid-sequences regarding their potential function. Besides their functional prediction, further characteristics and structural features have also been calculated.

Homology-based searches were applied to identify conserved sequences by means of comparison to public and/or proprietary nucleotide- and protein-databases. If a significant sequence similarity was found throughout the major section of a gene, it was concluded that the gene should have a similar function in *A. utahensis*. The homology-based method, which was used to annotate the gene list of *Actinoplanes utahensis*, is termed BLASTX (Coulson, Trends in Biotechnology, 1994, 12:76-80). BLASTX translates a given nucleotide sequence into three forward and three reverse complementary reading frames before it compares them against protein databases (e.g. the public, non-redundant protein database (nr-aa) at the National Center for Biotechnology Information (NCBI)).

Enzymatic classification has been performed on the basis of enzyme commission (EC) numbers (Webb, Edwin C., San Diego: Published for the International Union of Biochemistry and Molecular Biology by Academic Press, 1992, ISBN 0-12-227164-5. For further functional gene prediction, the cluster of orthologous groups of proteins (COG) classification system has been applied (*Tatusov* et al., Science, 1997, 278(5338):631-7 and Tatusov et al., *Nucleic Acids Res.* 2001, 29(1):22-8).

To identify potential transmembrane proteins, the software TMHMM (Krogh et al., J. Mol. Biol., 2001, 305(3): 567-80 and Sonnhammer et al., Proc. Int. Conf. Intell. Syst. Mol. Biol., 1998, 6:175-82) has been utilized. It makes use of Hidden Markov Models to predict transmembrane helices and other characteristics of transmembrane proteins. With information gained thereof, membrane associated functional predictions obtain significantly stronger conclusiveness.

The software SignalP (Bendtsen et al., J. Mol. Biol., 2004, 340:783-95 and Nielsen et al., protein Engineering, 2997, 10:1-6) was used to predict the secretion capability of the identified CDSs. This is done by means of Hidden Markov Models and neural networks, searching for the appearance and position of potential signal peptide cleavage sites within the amino acid sequence. The resulting score can be interpreted as a probability measure for the secretion of the translated protein. SignalP retrieves only those proteins which are secreted by the classical signal-peptide-bound mechanisms.

In order to identify further proteins from *Actinoplanes utahensis* which are not secreted via the classical way, the software SecretomeP has been applied (Bendtsen et al., BMC Microbiology, 2005, 5:58). The underlying neural network has been trained with secreted proteins, known to lack signal peptides despite their occurrence in the exoproteome. The final secretion capability of the translated genes was been derived by the combined results of SignalP and SecretomeP predictions.

To reveal polycistronic transcriptional units, proprietary software has been developed which predicts jointly transcribed genes by their orientation and proximity to neighboring genes (adopted from Salgado et al., Proc. Natl. Acad. Sci. USA, 2000, 97(12):6652-7). In light of these predictions, operon structures can be determined and based upon them further sequence regions can be derived with high probability of contained promoter and operator elements.

Secondary structures of single-stranded DNA-respective RNA-molecules were calculated by the RNAshapes software (Steffen et al., Bioinformatics, 2006, 22(4):500-503). The results were used for the intrinsic prediction of transcriptional terminators which indicate operon and gene ends, respectively.

Production Strain Reference Assembly

The assembly of reads obtained for all six production strains has been achieved by mapping them onto the wild type reference genome. For this task, two different software programs were utilized, taking the two read types into account which originated from the Genome Sequencer FLX (read-length 400-500 bases WGS) and Genome Analyzer IIx (read length 2×36 bases PE) system, respectively.

The gsMapper software (version 2.3, 454 Life Science) was used to align the reads from the Genome Sequencer FLX platform against the wild type reference genome. The program implements a heuristic to find the best alignment position for each read within the reference sequence. After all reads have been aligned, multiple alignments for the reads that align contiguously to the reference are performed in order to form contigs. From the contigs' multiple alignments, consensus basecall sequences are produced using the flow-signals of the reads in the multiple alignments, resulting in quality and confidence values for each base. For detailed information on the mapping algorithm see the *Genome Sequencer FLX System Software Manual Part C*, version 2.3 (October 2009).

As part of the CLC Genomics Workbench (CLC bio, Finlandsgade 10-12, Katrinebjerg, 8200 Aarhus N, Denmark), the short read assembly algorithm with PE information has been used to align reads from the Genome Analyzer IIx platform against the reference genome. For detailed information on the mapping algorithm see the *CLC Genomics Workbench User Manual* 3.7.1.

Identification of Mutations in the Production Strains

Genetic variations between the wild type strain SE50-100 and the latest production strain SN19910-37-2 have been automatically determined during the reference assembly process by means of the gsAssembler software (version 2.3, 454 Life Science). The details of the algorithm, determining single nucleotide polymorphisms (SNPs) as well as structural variations, can be found in the *Genome Sequencer FLX System Software Manual Part C*, version 2.3 (October 2009).

Mutations between the wild type strain and the five former productions strains have been determined using the CLC Genomics Workbench (CLC bio, Finlandsgade 10-12 Katrinebjerg, 8200 Aarhus N, Denmark). Specialized algorithms for high-throughput data analysis of SNPs and deletion/insertion polymorphisms (DIPs) have used, described in detail in *CLC Genomics Workbench User Manual* 3.7.1.

Sequencing, Assembly and Annotation of the *Actinoplanes utahensis* Wild Type Strain The draft genome sequence of the *Actinoplanes utahensis* wild type strain SE50-100 has been determined by a combination of sequencing information from three high-throughput runs. These were carried out on a Genome Sequencer FLX system, using two paired-end (PE) and one whole genome shotgun (WGS) approaches. The sequencings resulted in the successful nucleotide sequence determination of about 2 million reads, accounting for approximately 407 million sequenced bases in total (see table 2 for detailed information on the outcomes of each run).

Table 2 shows the results of the three high-throughput sequencing runs for the *A. utahensis* wild type strain SE50-100. Two paired-end (PE) and one whole genome shotgun (WGS) run were performed.

| Run | 454 Technology | Reads | Paired Reads | Bases |
|---|---|---|---|---|
| 1 | Standard, PE | 742,169 | 259,260 | 103,840,588 |
| 2 | Standard, PE | 751,570 | 265,457 | 105,329,378 |
| 3 | Titanium, WGS | 481,602 | — | 197,732,895 |
| | Total | 1,975,341 | 524,717 | 406,902,861 |

The sequenced reads were then successfully (99.65%) assembled into 476 contiguous sequences (contigs) exceeding 500 bases in length. Considering the resulting draft genome size of 9,122,632 bases, a genome coverage of 43.88-fold has been accomplished. Due to 480,030 (91.48%) successfully mapped paired-end reads, these contigs could already be ordered and oriented into eleven scaffolds (multiple contigs whose order and orientation are known from paired-end information). Table 3 gives further inside into the success- and error-rates of the assembly process leading to the preliminary draft genome sequence of the *Actinoplanes utahensis* wild type strain SE50-100.

Table 3 displays the results of successfully assembled reads, bases and the inferred read error. The inferred read error is calculated from mismatches between the reads and the consensus sequence of the final assembled contigs and measures the frequency of incorrectly called bases.

| Run | 454 Technology | Assembled Reads | Assembled Bases | Inferred Read Error |
|---|---|---|---|---|
| 1 | Standard, PE | 99.58% (739,079) | 98.08% (101,847,643) | 0.36% (370,520) |
| 2 | Standard, PE | 99.59% (748,526) | 98.18% (103,411,267) | 0.35% (364,397) |
| 3 | Titanium, WGS | 99.85% (480,863) | 99.33% (196,416,109) | 0.52% (1,018,256) |
| | Total | 99.65% (1,968,468) | 98.72% (401,675,019) | 0.44% (1,753,173) |

Interestingly, the genome sequence of the previously published acarbose cluster (Wehmeier, Biocat. Biotrans., 2003, 21:279-285 and Wehmeier and Piepersberg, Appl. Microbiol. Biotechnol., 2004, 63:613-625) was not identical to the sequencing results described above. In total, 37 single nucleotide polymorphisms (SNPs) and 24 deletion/insertion polymorphisms (DIPs) were found to be artificially introduced into the wild type sequence by the former sequencing attempt (see FIG. 1). The correction of these flawed sequencings lead to a minor elongation (42 bases) of the acbC gene as well as to the correction of several temporary frameshifts within the acbE gene. This however, had no consequence on overall annotation of the gene and the whole acarbose cluster.

FIG. 1 shows former false sequencings of the acarbose cluster which were corrected by the performed high-throughput sequencing described here.

Finishing of the Draft Genome Sequence by Fosmid Library Sequencing

Figure 2:
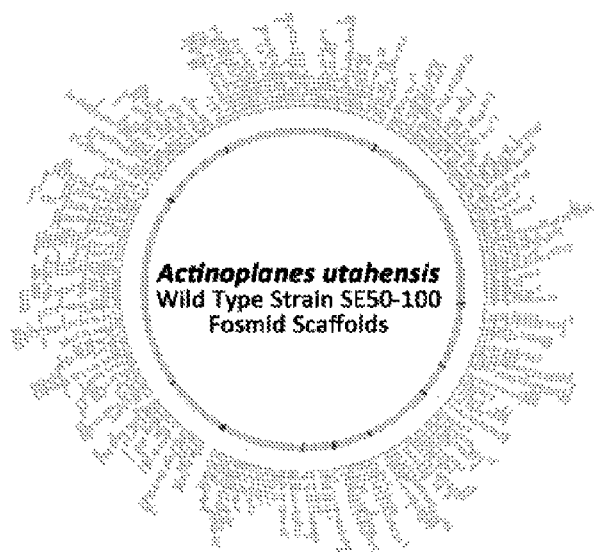

In order to obtain a whole genome scaffold of the wild type strain SE50-100, terminal insert sequences of 999 randomly selected fosmid clones have been determined (FIG. 2). No inconsistencies between the eleven paired-end-based scaffolds and the fosmid-library-based whole genome scaffold were found, corroborating the quality of the sequencing runs as well as the accuracy of the assembly process. In total 600 Sanger reads were derived from selected clones covering most of the remaining gaps of the draft genome. By manual assembly of these reads, 411 gaps between contigs could be bridged and closed respectively. The remaining 64 contigs form a single, circular scaffold and could not be bridged with this method due to long repetitive DNA-sequences and/or uncovered regions within the fosmid library. The resulting improved genome sequence of the *A. utahensis* wild type strain SE50-100 and is deposited in the appendix of this document.

FIG. 2 depicts the circular mapping of the fosmid clones (grey) used to build the genomic scaffold. The eleven scaffolds, which were based on the paired-end information, are marked in black.

Based on the improved genome sequence, a guanine-cytosine (G+C) content of 71.29% has been calculated which is typical for actinobacteria closely related to the *Actinoplanes* genus (Ventura et al., Microbiol. Mol. Biol. Rev., 2007, 71(3): 495-548).

Annotation of the *Actinoplanes utahensis* Wild Type Genome

On the foundation of the improved genome sequence, a full genome annotation has been performed, resulting in the determination of 8,027 putative coding sequences (CDS) with an average gene length of 985 nucleotides. Based thereon, *Actinoplanes utahensis* exhibits a coding density of 86.35% with notable G+C content difference of about 3% between coding (71.68%) and non-coding (68.70%) DNA regions. By examining the structural gene composition, 1,793 putative polycistronic transcriptional units were predicted, hosting 5,980 genes (74.50%) with an average number of 3.34 genes per operon. All nucleotide sequences as well as their amino acid translations are deposited in the appendix of this document. Table 4 summarizes the outcomes of the gene prediction process.

Table 4 shows the results of the gene prediction software for the A. utahensis wild type strain.

| Gene Prediction Parameter | Value |
| --- | --- |
| Coding sequences | 8,027 |
| Coding bases | 7,904,275 (86.35%) |
| Average gene length (bp) | 985 |
| Coding G + C content (%) | 71.68 |
| Non-coding G + C content (%) | 68.70 |
| Putative monocistronic transcriptional units | 2,047 |
| Putative polycistronic transcriptional units (PTU) | 1,793 |
| Average number of genes per PTU | 3.34 |

A variety of different programs were used to perform the functional annotation of the identified open reading frames. Due to extrinsic protein database comparisons 2,839 CDSs (35.67%) could be enzymatically characterized with an enzyme commission (EC) number. In addition 701 CDSs (8.73%), possessing typical transmembrane spanning regions, have been identified and classified as membrane-associated proteins. For a total number of 600 proteins signal peptides, and thus a high probability of being secreted into the extracellular medium, have been predicted. For additional 657 proteins, other secretion mechanisms were proposed. However, these predictions would result in an unusual high number of secreted proteins. Furthermore, the cluster of orthologous groups of proteins (COG) classification system has been applied and revealed an assignment of 3,983 (49.62%) CDSs to one or multiple COG-categories. Appendix table 9 offers a more comprehensive outline of the COG-categories and its subdivisions whereas the results of the general annotation are summarized in table 5. After full annotation, 2,684 genes (33.44%) had still no associated function. However, distant similarities to other sequences were found in public databases. For 434 (5.41%) orphan genes, not even distant related sequences were found in the databases.

Table 5 lists the results of the functional gene annotation for the A. utahensis wild type strain.

| Functional Annotation Parameter | Value |
| --- | --- |
| CDSs with annotated function | 4,909 (61.16%) |
| CDSs with EC-number | 2,839 (35.67%) |
| CDSs with COG-category | 3,983 (49.62%) |
| CDSs with unknown function | 2,684 (33.44%) |
| Orphan CDSs | 434 (5.41%) |
| Membrane associated proteins | 701 (8.73%) |
| Signal peptide predicted (75% confidence) | 600 (7.47%) |
| Other secretion mechanism predicted (95% conf.) | 657 (8.18%) |

Figure 3:
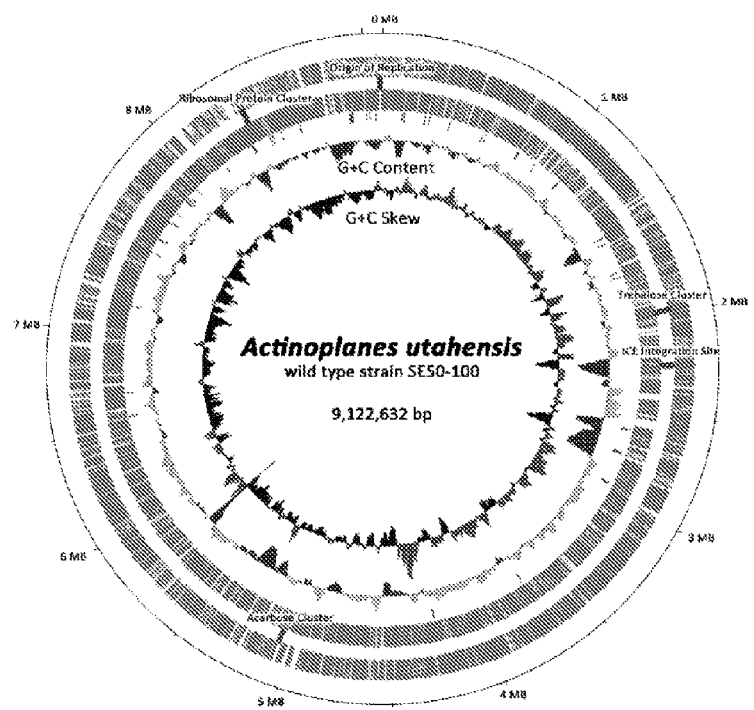

The annotated wild type genome is shown as a circular plot in FIG. 3. In addition to the depicted genes on the forward (outmost circle) and reverse strand (second circle), the G+C content (third circle) as well as the G+C skew (forth circle) is drawn in. Furthermore, several sites of high importance are marked, including the origin of replication, the previously described trehalose (Lee et al., Appl. Microbiol. Biotechnol., 2008, 80:767-778) and acarbose clusters, an interesting protein cluster consisting of about 25 contiguous ribosomal proteins as well as the location of an integrative and conjugative element (ICE). Table 6 lists the general features of the Actinoplanes utahensis wild type genome.

FIG. 3 shows a circular genome plot of the Actinoplanes utahensis SE50-100 wild type chromosome. On the outmost circle, genes in forward orientation are depicted. The second circle hosts genes on the reverse strand. The G+C content and the G+C skew are shown on the third and fourth circle, respectively.

Table 6 lists the general features of the A. utahensis SE50-100 genome.

| Feature | Genome |
| --- | --- |
| Total size (bp) | 9,122,632 |
| G + C content (%) | 71.29 |
| No. of CDS | 8,027 |
| No. of orphans | 434 |
| Coding density (%) | 86.35 |
| Average gene length (bp) | 985 |
| No. of rRNAs | 4 × 16S-23S-5S |
| No. of transposease genes | 39 |

By means of further extrinsic database searches, the most homologous gene and the organism it originates from have been assigned to each open reading frame. Together with the detailed annotations described above, this information is listed for each CDS in appendix table 10.

For many genes, an even more detailed manual annotation has been added to the (semi-) automated information described above. These genes include, but are not limited to all elements of the acarbose cluster (Wehmeier and Piepersberg, Appl. Microbiol. Biotechnol., 2004, 63: 613-625), the trehalose cluster (Lee et al., Appl. Microbiol. Biotechnol., 2008, 80:767-778) as well as certain classes of proteins such as starch degrading- and synthesizing-enzymes, sugar epimerases, genes involved in the uptake, transport and metabolism of maltose, secreted proteins, cellulases and genes involved in nitrogen metabolism and sporulation associated genes and their protein translations.

Metabolic Potential of the A. utahensis Wild Type Strain

Through the use of annotated EC numbers, it was possible to analyze the metabolic capabilities of Actinoplanes utahensis. Mapping of the EC numbers onto canonical pathways of the Kyoto Encyclopedia of Genes and Genomes (KEGG) revealed the availability of all major pathways regarding the central metabolism such as the glycolysis, the TCA cycle and the penthose-phosphate-pathway. For the utilization of the Entner-Dudoroff-pathway however, the key enzyme phosphogluconate dehydratase is missing for the catalysis of 6-Phospho-D-gluconate to 2-Dehydro-3-deoxy-D-gluconate-6P.

Genome Sequencing of the A. utahensis Production Strains

In addition to the wild type strain SE50-100, the latest production strain SN19910-37-21 as well as five former strains were sequenced in order to reveal genetic differences responsible for the increased acarbose production in these strains. The latest strain has been sequenced on the Genome Sequencer FLX (GS FLX) system, whereas the former strains were sequenced using the Genome Analyzer IIx (GA IIx) platform solely based on paired-end data. The results are summarized in table 7. In total, 5.6 billion bases were sequenced.

Table 7 lists all sequenced *A. utahensis* production strains in the order of their acarbose production.

| Strain Symbol | Platform | Protocol | Reads | Bases | Coverage |
|---|---|---|---|---|---|
| SN223-29-47 | GA IIx | PE | 34,571,040 | 1,209,986,400 | 132.64 |
| C445-P47 | GA IIx | PE | 30,360,960 | 1,062,633,600 | 116.48 |
| SN12755-48 | GA IIx | PE | 29,292,960 | 1,025,253,600 | 112.39 |
| SC3687-18-43 | GA IIx | PE | 28,105,200 | 983,682,000 | 107.83 |
| SC7177-40-17 | GA IIx | PE | 27,332,400 | 956,634,000 | 104.86 |
| SN19910-37-21 | GS FLX | Titanium, WGS | 776,085 | 297,036,826 | 32.56 |

Identification of Genetic Variations Between the Mutated Strains and the Wild Type Consequent reference mapping against the previously finished wild type genome lead to the assembly of all six production strains. In addition, all genetic variations between the production strains and the wild type strain could be determined. Interestingly, no major deletion mutations had taken place, as the wild type genome is generally completely covered by the reads originating from the production strains. However, 1,826 single nucleotide polymorphisms (SNPs) and 128 deletion/insertion polymorphisms (DIPs) were discovered between the wild type genome and the latest production strain. The number of SNPs introduced into each genome, as listed in table 8, rises with the chronological development of the strain. All mutations and their exact transitions are listed in appendix table 11 together with the production strains, showing their first occurrence.

Table 8 lists the number of single nucleotide polymorphisms (SNPs) and deletion/insertion polymorphisms (DIPs) that were detected between the corresponding production strain and the *A. utahensis* wild type genome.

| Strain Symbol | SNPs | DIPs |
|---|---|---|
| SN223-29-47 | 428 | 7 |
| C445-P47 | 1,040 | 6 |
| SN12755-48 | 1,204 | 6 |
| SC3687-18-43 | 1,331 | 5 |
| SC7177-40-17 | 1,533 | 7 |
| SN19910-37-21 | 1,826 | 128 |

Figure 4:
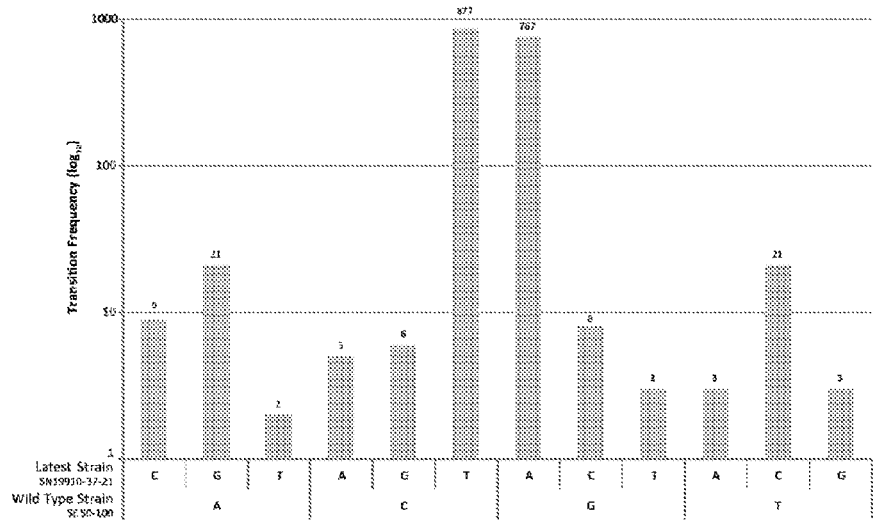

The SNP based nucleotide transitions were not gaussian distributed but show a more than 100-fold preference for the two transition G→A and C→T. FIG. 4 depicts these findings.

FIG. 4 shows the transition frequency of SNP mutations between the wild type and the latest production strain.

Figure 5:
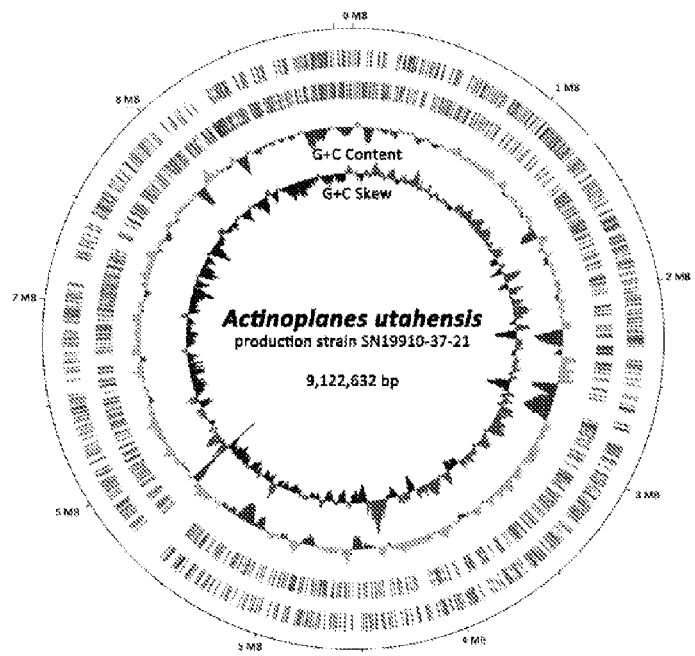

By comparison of annotated gene loci against positions were SNPs and DIPs were introduced, it was found that 1,896 genes (23.62%) were affected by these mutations on the nucleotide level as can be seen in FIG. 5. Of these, 376 genes were still coding for the identical protein sequence, holding only silent mutations. On the other side, the protein sequence of 816 genes changed on individual positions, leaving the amino acid sequence unchanged for the most part. However, the 704 residuary genes were hit by mutations changing their length and/or reading frame. In detail, 429 genes were predicted to have an increased length compared to the wild type whereas 275 genes were shortened.

FIG. 5 visualizes only the 1,896 genes which were hit by a mutation event. On the outmost circle, forward oriented genes are listed. On the second circle, backward genes are depicted.

The third and forth circles represent the G+C content and the G+C skew, respectively.

Modifications of the Central Metabolism

The enzyme encoding genes which were affected by mutagenesis events are likely to have an impact on the overall metabolism as well as special pathways like the one encoding for the formation of acarbose. For this reason, these genes were mapped according to their EC numbers onto canonical pathways of the KEGG database to identify loss of functionality introduced by the mutagenesis experiments. While several enzymes of the central metabolism were affected by SNPs, only few genes were hit by mutations leading to a probable loss of function. In addition, for each of these severely changed genes at least one other gene, annotated with the same EC number, was still available, probably assisting for the knocked out version.

Modifications of the Acarbose Cluster and the Use of Former Production Strains

Figure 6:
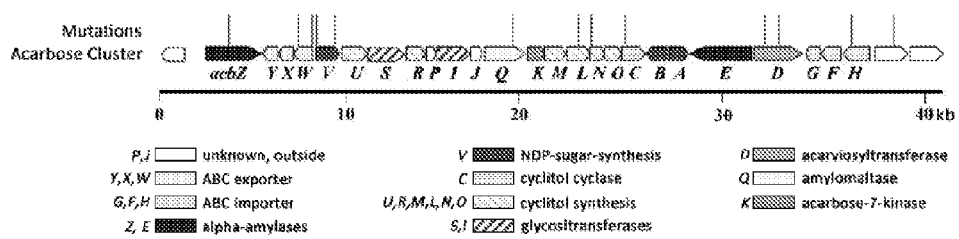

By sequencing of the former production strains, it was possible to trace mutations back through time to the strain they were first introduced into. This analysis was especially enlightening on the sequence of the acarbose cluster as depicted in FIG. 6. The 13 SNPs which hit the cluster were sequentially introduced as mutation experiments were executed. Two SNPs were introduced into the intragenic region between genes acbW and acbV. Furthermore, two SNPs were introduced to the acbD gene. The acbD encoding protein, an acarviosyltransferase is believed to load acarbose with maltodextrins in the extracellular space prior to reimport through the acarbose importer complex. Another mutation is located in the acbH gene which encodes the subject binding protein of the acarbose importer complex.

FIG. 6 shows the acarbose cluster in conjunction with the mutations which were introduced therein during the development of the depicted former production strains.

LIST OF ALL MUTATIONS

Table 9 lists all mutations introduced into the *Actinoplanes utahensis* wild type strain SE50-100 by the corresponding production strains.

| Position in reference wild type strain SE50-100 | Base in Reference strain | SN223-29-47 | C445-P47 | SN12755-48 | SC3687-18-43 | SC7177-40-17 | SN19910-27-21 | Affected Gene ID |
|---|---|---|---|---|---|---|---|---|
| 7102 | G | | A | A | A | A | A | cds_wt_4 |
| 11919 | G | A | A | A | A | A | A | cds_wt_7 |
| 12285 | G | A | A | A | A | A | A | cds_wt_7 |
| 12651 | G | A | A | A | A | A | A | cds_wt_7 |
| 13511 | G | A | A | A | A | A | A | cds_wt_7 |
| 46974 | C | T | T | T | T | T | T | cds_wt_41 |
| 62542 | C | | T | T | T | T | T | cds_wt_52 |
| 64957 | C | T | T | T | T | T | T | cds_wt_54 |
| 65055 | C | T | T | T | T | T | T | cds_wt_54 |
| 65455 | C | C/T | | | | | T/C | — |
| 65460 | C | C/T | | | | | T | — |
| 65882 | G | A | A | A | A | A | A | cds_wt_55 |
| 72685 | A | | | | | | A/G | — |
| 72693 | A | | | | | | A/G | — |
| 72701 | A | | | | | | A/G | — |
| 73373 | C | | T | T | T | T | T | cds_wt_61 |
| 73467 | C | | T | T | T | T | T | cds_wt_61 |
| 76845 | C | T | T | T | T | T | T | cds_wt_64 |
| 78965 | C | T | T | T | T | T | T | cds_wt_66 |
| 80653 | G | | A | A | A | A | A | cds_wt_67 |
| 85503 | G | | A | A | A | A | A | cds_wt_70 |
| 88269 | G | | A | A | A | A | A | cds_wt_72 |
| 88369 | G | | A | A | A | A | A | cds_wt_72 |
| 89368 | C | T | T | T | T | T | T | cds_wt_72 |
| 89901 | C | | T | T | T | T | T | cds_wt_72 |
| 90029 | C | | T | T | T | T | T | cds_wt_72 |
| 91949 | C | T | T | T | T | T | T | cds_wt_74 |
| 93427 | C | T | T | T | T | T | T | — |
| 101351 | G | | A | A | A | A | A | cds_wt_82 |
| 103967 | C | | | | | | T | cds_wt_84 |
| 104063 | C | T | | T | T | T | T | cds_wt_84 |
| 110857 | C | | T | T | T | T | T | cds_wt_88 |
| 112637 | G | | A | A | A | A | A | cds_wt_90 |
| 114499 | G | | A | A | A | A | A | cds_wt_90 |
| 115250 | G | | A | A | A | A | A | cds_wt_92 |
| 115873 | C | | T | T | T | T | T | cds_wt_92 |
| 115983 | C | | T | | | | T | cds_wt_93 |
| 117494 | C | | T | T | T | T | T | cds_wt_93 |
| 119344 | G | | A | A | A | A | A | cds_wt_94 |
| 134489 | C | T | T | T | T | T | T | cds_wt_106 |
| 139515 | C | | T | T | T | T | T | — |
| 146767 | C | T | T | T | T | T | T | cds_wt_119 |
| 161035 | G | | A | A | A | A | A | cds_wt_133 |
| 172303 | G | | A | A | A | A | A | cds_wt_143 |
| 176176 | G | | | | | A | A | cds_wt_146 |
| 178880 | G | | | | | | G/A | cds_wt_148 |
| 180754 | C | | | T | T | | T | cds_wt_150 |
| 180925 | C | | | T | | | T | cds_wt_150 |
| 184674 | G | | | A | A | A | A | cds_wt_154 |
| 190568 | C | | T | T | T | T | T | cds_wt_159 |
| 190644 | C | | T | T | T | T | T | cds_wt_159 |
| 191971 | C | | T | T | T | T | T | cds_wt_161 |
| 193584 | G | | A | A | A | A | A | cds_wt_162 |
| 196028 | C | | T | T | T | T | T | cds_wt_164 |
| 196338 | C | | T | T | T | T | T | — |
| 214992 | G | | A | A | A | A | A | — |
| 222841 | G | | | | | A | A | cds_wt_187 |
| 222924 | C | | | | | T | T | cds_wt_187 |
| 228543 | C | | | | T | T | T | cds_wt_193 |
| 247200 | C | | | | | T | T | cds_wt_205 |
| 248952 | C | T | T | T | T | T | T | cds_wt_206 |
| 253299 | G | | | | | | A | cds_wt_209 |
| 254551 | G | | | | | | A | cds_wt_210 |
| 259829 | C | | | T | T | | T | — |
| 268705 | C | | T | T | T | T | T | cds_wt_224 |
| 270822 | G | A | A | A | A | A | A | cds_wt_227 |
| 273723 | G | A | | A | A | | A | cds_wt_229 |
| 276430 | C | | T | T | T | T | T | cds_wt_232 |
| 276561 | C | | | T | T | T | T | cds_wt_232 |
| 283007 | G | A | A | A | A | A | A | — |
| 283062 | G | A | A | A | A | A | A | — |
| 287132 | C | | | | T | T | T | cds_wt_247 |
| 294767 | G | | | | | A | A | cds_wt_253 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 295356 | C | T | T | T | T | T | T | cds_wt_254 |
| 300028 | C | | | | | | T | cds_wt_256 |
| 303810 | G | | | | | A | A | cds_wt_259 |
| 313837 | C | | | | | T | T | cds_wt_271 |
| 316698 | G | | | | | A | A | cds_wt_273 |
| 316929 | G | | A | A | A | A | A | cds_wt_273 |
| 325503 | C | T | T | T | T | T | T | cds_wt_283 |
| 331088 | G | | | A | A | | A | — |
| 340040 | G | | A | A | | | A | cds_wt_297 |
| 342987 | G | | A | A | A | A | A | cds_wt_299 |
| 343915 | G | A | A | A | A | A | A | cds_wt_300 |
| 352688 | C | T | T | T | T | T | T | cds_wt_308 |
| 353668 | G | | A | A | A | A | A | cds_wt_308 |
| 361019 | G | | A | A | A | A | A | cds_wt_314 |
| 362742 | G | | A | A | A | A | A | cds_wt_315 |
| 375835 | C | T | T | T | T | T | T | cds_wt_329 |
| 381358 | G | | A | A | | | A | cds_wt_335 |
| 382029 | G | | A | A | A | A | A | cds_wt_335 |
| 391677 | C | T | | T | T | T | T | cds_wt_345 |
| 400166 | C | | T | T | T | T | T | cds_wt_350 |
| 406413 | G | | | A | A | | A | cds_wt_355 |
| 409544 | G | | A | A | A | A | A | cds_wt_358 |
| 416199 | G | | | | | | A | cds_wt_364 |
| 419938 | C | T | T | T | T | T | T | cds_wt_369 |
| 425067 | G | | | | | A | A | cds_wt_374 |
| 425419 | G | | | | | A | A | cds_wt_374 |
| 426464 | G | | A | A | A | A | A | cds_wt_376 |
| 438324 | C | | T | T | T | T | T | cds_wt_385 |
| 446368 | G | | A | A | A | A | A | cds_wt_390 |
| 446984 | G | | A | A | A | A | A | cds_wt_392 |
| 447392 | G | | A | A | A | A | A | — |
| 450492 | G | | | | | | A | cds_wt_395 |
| 458678 | C | | T | T | T | T | T | cds_wt_403 |
| 459753 | C | | | | | | T | — |
| 459833 | A | G | | G | | G | G | cds_wt_405 |
| 466505 | G | | A | A | A | A | A | cds_wt_416 |
| 474923 | G | | | | | | A | cds_wt_423 |
| 482599 | G | | | A | A | A | A | cds_wt_430 |
| 494993 | G | | A | A | A | A | A | cds_wt_445 |
| 500358 | C | T | T | T | T | T | T | cds_wt_449 |
| 510408 | C | | | T | T | T | T | cds_wt_459 |
| 511515 | G | | A | A | A | A | A | cds_wt_460 |
| 512816 | G | | | | | | A | cds_wt_463 |
| 513902 | C | T | T | T | T | T | T | cds_wt_464 |
| 515197 | G | | | | | | A | cds_wt_465 |
| 518156 | G | | A | A | A | A | A | cds_wt_468 |
| 533618 | G | A | A | A | A | A | A | cds_wt_485 |
| 536327 | C | T | | T | T | | T | cds_wt_488 |
| 542891 | G | | A | A | A | A | A | cds_wt_493 |
| 548989 | C | | T | T | T | T | T | cds_wt_496 |
| 553081 | G | | A | A | A | A | A | cds_wt_500 |
| 553332 | G | | A | A | A | A | A | cds_wt_500 |
| 557884 | G | | | | | | A | cds_wt_502 |
| 557907 | G | | | | | | A | cds_wt_502 |
| 567026 | C | T | T | T | T | T | T | — |
| 587166 | A | G | G | G | G | G | G | cds_wt_528 |
| 590721 | G | | | | | | A | cds_wt_530 |
| 602225 | C | T | T | T | T | T | T | cds_wt_543 |
| 604184 | C | | | | | | T | cds_wt_544 |
| 605918 | C | T | T | T | T | T | T | cds_wt_546 |
| 621774 | C | | | | | T | T | — |
| 624361 | C | T | T | T | T | T | T | — |
| 625600 | C | T | T | T | T | T | T | — |
| 626283 | G | | A | A | A | A | A | — |
| 629283 | G | | A | A | A | A | A | cds_wt_565 |
| 636108 | C | | | | | T | T | — |
| 648981 | G | | A | A | A | A | A | cds_wt_582 |
| 684062 | G | | A | A | A | A | A | cds_wt_613 |
| 702171 | C | | | | | T | T | cds_wt_627 |
| 702650 | C | | | | | T | T | cds_wt_627 |
| 703452 | C | | T | T | T | T | T | cds_wt_628 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 706109 | C | | | | | | T | cds_wt_631 |
| 711168 | G | | A | A | A | | A | — |
| 712462 | A | | | | | | A/G | cds_wt_637 |
| 714678 | G | | | A | A | A | A | cds_wt_639 |
| 714785 | G | | A | A | A | A | A | cds_wt_639 |
| 717602 | G | | | A | A | A | A | cds_wt_641 |
| 719600 | G | | | A | A | A | A | cds_wt_643 |
| 724097 | G | | | A | A | A | A | cds_wt_646 |
| 738525 | C | | | | | T | T | cds_wt_655 |
| 744594 | G | | | | | | A | cds_wt_662 |
| 746362 | G | | | A | A | A | A | cds_wt_664 |
| 750285 | C | | T | T | T | T | T | cds_wt_667 |
| 752663 | G | | A | A | A | A | A | cds_wt_670 |
| 763762 | C | | | | | | C/G | — |
| 763785 | G | | | | | | G/C | — |
| 763792 | C | | | | | | C/G | — |
| 763951 | C | | | | | | C/G | — |
| 765635 | G | A | A | A | A | A | A | cds_wt_682 |
| 766073 | G | | A | A | A | A | A | cds_wt_682 |
| 769289 | G | | A | A | A | A | A | cds_wt_686 |
| 776043 | C | | | T | T | T | T | cds_wt_692 |
| 780677 | C | | | | | T | T | — |
| 781916 | C | | | T | T | T | T | cds_wt_698 |
| 783900 | C | | | T | T | T | T | cds_wt_699 |
| 786653 | G | A | A | A | A | A | A | cds_wt_702 |
| 795572 | C | T | T | T | T | T | T | cds_wt_709 |
| 796824 | G | | | A | A | A | A | cds_wt_710 |
| 798663 | G | | | A | A | A | A | cds_wt_712 |
| 810530 | G | | | | | | A | cds_wt_724 |
| 810533 | C | | | | | | G | — |
| 810556 | T | | | | | | T/C | cds_wt_725 |
| 810557 | G | | | | | | G/C | cds_wt_725 |
| 810563 | C | | | | | | C/T | cds_wt_725 |
| 810576 | A | | | | | | A/G | cds_wt_725 |
| 819250 | G | | A | A | A | A | A | cds_wt_730 |
| 829153 | C | T | T | T | T | T | T | cds_wt_739 |
| 830171 | C | | | | | | T | cds_wt_740 |
| 831404 | G | | A | A | A | A | A | cds_wt_741 |
| 838352 | G | | | | | | A | cds_wt_748 |
| 842068 | G | | A | A | A | A | A | cds_wt_750 |
| 847887 | G | | | | | A | A | cds_wt_753 |
| 861775 | C | T | T | T | T | T | T | cds_wt_768 |
| 870304 | G | | A | A | A | A | A | cds_wt_776 |
| 880820 | C | T | T | T | T | T | T | cds_wt_785 |
| 897424 | C | T | T | T | T | T | T | cds_wt_794 |
| 907842 | G | A | A | A | A | A | A | cds_wt_799 |
| 908987 | C | T | T | T | T | T | T | — |
| 921289 | G | | A | A | A | A | A | cds_wt_813 |
| 941088 | G | A | A | A | A | A | A | cds_wt_829 |
| 945666 | G | | | | A | A | A | cds_wt_834 |
| 959932 | C | | | | | | T | cds_wt_847 |
| 964504 | G | | A | A | A | A | A | cds_wt_850 |
| 964558 | C | | | | | T | T | cds_wt_850 |
| 970334 | C | T | T | T | T | T | T | cds_wt_857 |
| 972781 | C | | T | T | T | | T | cds_wt_860 |
| 995285 | G | | A | A | A | A | A | cds_wt_879 |
| 1004653 | C | | | | | | T | — |
| 1006503 | C | T | T | T | T | T | T | cds_wt_889 |
| 1008680 | G | | | | | | A | cds_wt_890 |
| 1009674 | G | A | A | A | A | A | A | cds_wt_893 |
| 1009813 | G | | | | | | A | cds_wt_893 |
| 1023301 | C | | T | T | T | T | T | cds_wt_902 |
| 1028963 | G | | A | A | A | A | A | cds_wt_908 |
| 1030345 | C | T | T | T | T | T | T | cds_wt_910 |
| 1030822 | G | | A | A | A | A | A | cds_wt_911 |
| 1037262 | G | | A | A | A | A | A | cds_wt_917 |
| 1041811 | C | | T | T | T | T | T | cds_wt_919 |
| 1054013 | C | | T | T | T | T | T | — |
| 1055406 | C | T | T | T | T | T | T | — |
| 1082623 | G | | A | A | | | A | cds_wt_952 |
| 1085482 | C | | | | | T | T | cds_wt_953 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 1085499 | C | | T | T | T | T | T | cds_wt_953 |
| 1088995 | C | T | T | T | T | T | T | cds_wt_956 |
| 1097530 | C | | | T | T | T | T | cds_wt_967 |
| 1107807 | T | | | | | | A | — |
| 1117905 | C | | | | | T | T | — |
| 1119169 | G | | | | | A | A | cds_wt_987 |
| 1120103 | G | A | | | | | A | cds_wt_989 |
| 1120852 | G | A | A | A | A | A | A | cds_wt_990 |
| 1122832 | C | | | | | T | T | cds_wt_990 |
| 1123080 | C | | T | T | T | T | T | cds_wt_990 |
| 1128153 | G | | A | A | A | A | A | cds_wt_993 |
| 1130585 | G | | A | A | A | A | A | cds_wt_999 |
| 1145784 | C | | | | | T | T | cds_wt_1014 |
| 1146897 | G | | A | A | A | A | A | cds_wt_1015 |
| 1153166 | C | | | | | | T | cds_wt_1021 |
| 1163219 | C | | | | | T | T | cds_wt_1027 |
| 1163309 | G | | A | A | A | A | A | cds_wt_1027 |
| 1163538 | G | | | A | A | | A | cds_wt_1027 |
| 1169629 | C | | | | T | T | T | cds_wt_1032 |
| 1169882 | C | | | | | T | T | cds_wt_1032 |
| 1170591 | C | | | | T | T | T | cds_wt_1032 |
| 1172808 | C | | | | | T | T | cds_wt_1035 |
| 1172940 | C | | T | T | T | T | T | cds_wt_1035 |
| 1173551 | C | | T | T | T | T | T | cds_wt_1035 |
| 1179238 | C | | T | T | T | T | T | — |
| 1192548 | C | | | | | T | T | cds_wt_1050 |
| 1194346 | C | | T | T | T | T | T | cds_wt_1051 |
| 1194637 | G | A | A | A | A | A | A | cds_wt_1051 |
| 1196403 | C | T | T | T | T | T | T | cds_wt_1053 |
| 1208932 | C | | | | | | T | cds_wt_1065 |
| 1221399 | C | | | | | T | T | cds_wt_1081 |
| 1222202 | C | | T | T | T | T | T | cds_wt_1083 |
| 1225212 | C | | | | | T | T | cds_wt_1086 |
| 1242677 | G | | A | A | A | A | A | cds_wt_1101 |
| 1249095 | C | | | | | T | T | cds_wt_1105 |
| 1250477 | G | | | | | | A | — |
| 1255855 | C | T | T | T | T | T | T | — |
| 1260719 | C | T | | T | T | | T | cds_wt_1114 |
| 1261347 | C | | | | | | T | cds_wt_1114 |
| 1261926 | C | T | T | T | T | T | T | cds_wt_1115 |
| 1262307 | G | | A | A | A | A | A | cds_wt_1115 |
| 1262367 | G | | A | A | A | A | A | cds_wt_1115 |
| 1267545 | C | | | | | T | T | cds_wt_1120 |
| 1270664 | C | | | | | T | T | cds_wt_1122 |
| 1272928 | C | | | | | T | T | cds_wt_1123 |
| 1273797 | C | | | | | T | T | cds_wt_1124 |
| 1277491 | G | A | | A | A | | A | cds_wt_1127 |
| 1282245 | G | | | | | | A | cds_wt_1131 |
| 1284346 | C | | | | | T | T | cds_wt_1134 |
| 1285883 | C | T | T | T | T | T | T | cds_wt_1136 |
| 1291340 | C | | | | | T | T | cds_wt_1144 |
| 1300654 | G | | A | A | A | A | A | cds_wt_1155 |
| 1306705 | C | | | | | T | T | — |
| 1307526 | C | T | T | T | T | T | T | — |
| 1308200 | C | T | T | T | T | T | T | cds_wt_1161 |
| 1315876 | C | | | | | T | T | cds_wt_1170 |
| 1317961 | G | A | A | A | A | A | A | cds_wt_1172 |
| 1321981 | C | | | | T | T | T | cds_wt_1176 |
| 1322304 | C | | | | | T | T | cds_wt_1176 |
| 1325473 | C | | | | | T | T | cds_wt_1179 |
| 1325983 | G | A | A | A | A | A | A | cds_wt_1180 |
| 1327837 | C | | | | | T | T | cds_wt_1183 |
| 1329364 | C | | | | T | T | T | cds_wt_1185 |
| 1330802 | G | | A | A | A | A | A | cds_wt_1186 |
| 1335338 | C | | T | T | T | | T | cds_wt_1189 |
| 1342390 | C | | | | | T | T | cds_wt_1195 |
| 1343472 | A | | | | C | C | C | cds_wt_1196 |
| 1344261 | C | | | | | T | T | cds_wt_1196 |
| 1346995 | C | | | | | T | T | — |
| 1348395 | G | | | | | A | A | cds_wt_1202 |
| 1351344 | C | | | | | T | T | cds_wt_1204 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 1352745 | C | | | | T | T | T | cds_wt_1206 |
| 1356389 | C | | | | T | T | T | — |
| 1359105 | G | | A | A | A | A | A | cds_wt_1210 |
| 1359182 | C | | | | | T | T | cds_wt_1210 |
| 1362032 | C | | | | | T | T | cds_wt_1212 |
| 1370065 | G | | A | A | A | A | A | cds_wt_1221 |
| 1370088 | C | T | T | T | T | T | T | cds_wt_1221 |
| 1379821 | C | | | | | | T | cds_wt_1228 |
| 1382638 | G | | A | A | A | A | A | cds_wt_1232 |
| 1388800 | C | | T | T | T | T | T | cds_wt_1238 |
| 1404278 | C | T | | | | | T | cds_wt_1248 |
| 1409508 | G | | | | | A | A | cds_wt_1254 |
| 1410045 | G | | | | | A | A | — |
| 1413757 | G | | | | | A | A | cds_wt_1259 |
| 1415711 | G | | | | | A | A | cds_wt_1262 |
| 1415773 | G | | | | | A | A | cds_wt_1262 |
| 1418132 | C | | | | | T | T | cds_wt_1264 |
| 1419671 | G | | | | | A | A | cds_wt_1265 |
| 1420016 | C | | | | | T | T | cds_wt_1265 |
| 1428228 | C | | T | T | T | T | T | cds_wt_1270 |
| 1428233 | C | T | T | T | T | T | T | cds_wt_1270 |
| 1435884 | C | | | | | T | T | cds_wt_1279 |
| 1438355 | C | | | | | T | T | cds_wt_1282 |
| 1440872 | G | | | | A | A | A | cds_wt_1282 |
| 1443149 | C | | | | | | T | cds_wt_1285 |
| 1450678 | G | | A | A | A | A | A | cds_wt_1294 |
| 1453590 | G | | A | A | A | A | A | cds_wt_1296 |
| 1454075 | C | | | | | | T | cds_wt_1297 |
| 1455191 | G | | A | A | A | A | A | cds_wt_1298 |
| 1463521 | C | | | T | T | T | T | cds_wt_1303 |
| 1473239 | C | | T | T | T | T | T | cds_wt_1311 |
| 1474775 | G | | | | | A | A | cds_wt_1312 |
| 1482297 | C | | | | T | T | T | cds_wt_1318 |
| 1494980 | G | | | | | A | A | cds_wt_1326 |
| 1502729 | G | A | A | A | A | A | A | cds_wt_1332 |
| 1514463 | C | T | | | | | T | — |
| 1525258 | G | | | | | | A | cds_wt_1357 |
| 1533361 | C | | | | | | T | cds_wt_1364 |
| 1545597 | T | | | | | | T/C | — |
| 1563822 | C | | T | T | T | T | T | cds_wt_1394 |
| 1563854 | C | T | T | T | T | T | T | cds_wt_1394 |
| 1565818 | C | | | | | | T | cds_wt_1396 |
| 1566866 | C | | | | | T | T | cds_wt_1397 |
| 1570236 | G | | | | | A | A | cds_wt_1398 |
| 1570636 | C | T | T | T | T | T | T | cds_wt_1399 |
| 1581033 | T | | C | C | C | C | C | cds_wt_1411 |
| 1594972 | G | A | A | A | A | A | A | cds_wt_1426 |
| 1614616 | C | | T | T | T | T | T | cds_wt_1441 |
| 1615586 | C | | T | T | T | T | T | cds_wt_1441 |
| 1616152 | C | | T | T | T | T | T | cds_wt_1442 |
| 1616981 | C | | | T | T | T | T | cds_wt_1443 |
| 1617561 | C | | | T | | T | T | cds_wt_1443 |
| 1617928 | C | T | T | T | T | T | T | cds_wt_1444 |
| 1622589 | G | A | A | A | A | A | A | cds_wt_1447 |
| 1641656 | C | T | | | | | T | cds_wt_1457 |
| 1641711 | C | | | | | | T | cds_wt_1457 |
| 1641953 | C | | T | | | T | T | cds_wt_1458 |
| 1648653 | G | | A | A | A | A | A | cds_wt_1466 |
| 1648676 | G | | A | A | A | A | A | cds_wt_1466 |
| 1649444 | C | | | | | T | T | — |
| 1650400 | G | A | A | A | A | A | A | — |
| 1658589 | G | | | | | A | A | cds_wt_1467 |
| 1661376 | G | | | | | | A | cds_wt_1469 |
| 1664324 | C | | | | | T | T | cds_wt_1474 |
| 1680524 | C | T | T | T | T | T | T | cds_wt_1485 |
| 1682349 | G | | A | A | A | A | A | cds_wt_1485 |
| 1682842 | C | | | | | T | T | cds_wt_1486 |
| 1686608 | C | | | | T | T | T | cds_wt_1490 |
| 1695571 | C | | T | T | T | T | T | cds_wt_1495 |
| 1699167 | G | | A | A | A | A | A | cds_wt_1499 |
| 1700705 | G | | | | | | A | cds_wt_1501 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 1715788 | T | | | | | | C | cds_wt_1517 |
| 1727072 | G | | A | A | A | A | A | cds_wt_1526 |
| 1747963 | C | T | T | T | T | T | T | cds_wt_1546 |
| 1748448 | C | | | | | T | T | cds_wt_1547 |
| 1778278 | C | | | | | T | T | cds_wt_1569 |
| 1779396 | C | | T | T | T | T | T | cds_wt_1570 |
| 1779723 | C | | T | T | T | T | T | cds_wt_1570 |
| 1792608 | G | | A | A | A | A | A | cds_wt_1583 |
| 1793069 | C | | | | | T | T | cds_wt_1584 |
| 1795610 | C | | | | | T | T | cds_wt_1588 |
| 1803172 | C | | T | T | T | T | T | — |
| 1805902 | C | T | T | T | T | T | T | cds_wt_1595 |
| 1815104 | C | T | T | T | T | T | T | cds_wt_1601 |
| 1848170 | G | | | | | | A | cds_wt_1640 |
| 1858054 | C | | | | T | T | T | cds_wt_1649 |
| 1874864 | G | | A | A | A | A | A | cds_wt_1664 |
| 1878368 | C | | T | T | T | T | T | cds_wt_1669 |
| 1878456 | C | | T | T | T | T | T | cds_wt_1669 |
| 1881797 | G | | A | A | A | A | A | cds_wt_1671 |
| 1881821 | G | | A | A | A | A | A | cds_wt_1671 |
| 1883780 | G | | A | A | A | A | A | cds_wt_1673 |
| 1886024 | G | A | A | A | A | A | A | cds_wt_1677 |
| 1886177 | G | | A | A | A | A | A | cds_wt_1677 |
| 1886499 | G | A | A | A | A | A | A | cds_wt_1677 |
| 1888003 | G | | | | | | A | cds_wt_1678 |
| 1888277 | G | | A | A | A | A | A | — |
| 1891012 | G | | A | A | A | A | A | cds_wt_1680 |
| 1891205 | C | T | T | T | T | T | T | cds_wt_1681 |
| 1891493 | G | | A | A | A | A | A | cds_wt_1682 |
| 1891608 | G | | A | A | A | A | A | cds_wt_1682 |
| 1895230 | C | | | | | | T | cds_wt_1683 |
| 1896121 | G | | A | A | A | A | A | cds_wt_1684 |
| 1898465 | G | | A | A | A | A | A | cds_wt_1686 |
| 1904126 | G | | A | A | A | A | A | cds_wt_1689 |
| 1904415 | G | | A | A | A | A | A | cds_wt_1689 |
| 1918600 | G | | | | | A | A | cds_wt_1702 |
| 1926767 | G | | | | | A | A | cds_wt_1710 |
| 1930239 | G | A | A | A | A | A | A | — |
| 1933689 | G | | A | A | A | A | A | cds_wt_1718 |
| 1935111 | G | | | A | A | A | A | cds_wt_1721 |
| 1938524 | G | | A | A | A | A | A | cds_wt_1725 |
| 1941158 | G | | A | A | A | A | A | cds_wt_1729 |
| 1950155 | C | | | | T | | T | cds_wt_1737 |
| 1961896 | C | | | | T | T | T | cds_wt_1749 |
| 1964247 | C | | | | | | T | — |
| 1971635 | A | | | | | C | C | cds_wt_1755 |
| 1973884 | G | | A | A | A | A | A | cds_wt_1756 |
| 1985968 | G | A | A | A | A | A | A | cds_wt_1769 |
| 1986215 | C | | | | | | T | cds_wt_1769 |
| 1987891 | C | | | | | T | T | cds_wt_1770 |
| 1987907 | C | | | | | T | T | cds_wt_1770 |
| 1993612 | G | | A | A | A | A | A | cds_wt_1778 |
| 1997079 | C | | T | T | T | T | T | cds_wt_1783 |
| 2043866 | G | | | | | A | A | cds_wt_1830 |
| 2043889 | G | | | | | A | A | cds_wt_1830 |
| 2048938 | C | | | | | | T | cds_wt_1835 |
| 2058063 | G | | A | A | A | A | A | cds_wt_1841 |
| 2058998 | G | A | A | A | A | A | A | cds_wt_1841 |
| 2060664 | G | | A | A | A | A | A | cds_wt_1843 |
| 2060796 | G | | A | A | A | A | A | cds_wt_1843 |
| 2067415 | G | | | | | | A | — |
| 2067911 | G | A | A | A | A | A | A | cds_wt_1851 |
| 2071535 | G | | | | | | A | cds_wt_1854 |
| 2077305 | A | | | | | | G/A | — |
| 2077309 | T | | | | | | C/T | — |
| 2077321 | A | | | | | | G/A | — |
| 2077324 | G | | | | | | A/G | — |
| 2077336 | A | | | | | | G/A | — |
| 2077351 | C | | | | | | T/C | — |
| 2077353 | A | | | | | | G/A | — |
| 2077369 | C | | | | | | T/C | — |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 2077383 | G | G/A | G/A | G/A | G/A | G/A | A/G | — |
| 2077384 | C | C/G | C/G | C/G | C/G | C/G | G/C | — |
| 2077398 | G | G/C | G/C | G/C | G/C | G/C | G/C | — |
| 2077432 | T | | | | | | C/T | — |
| 2077603 | A | | | | | | G/A | cds_wt_1862 |
| 2077615 | C | | | | | | A/C | cds_wt_1862 |
| 2077618 | G | | | | | | A/G | cds_wt_1862 |
| 2077636 | T | | | | | | C/T | cds_wt_1862 |
| 2077645 | G | | | | | | C/G | cds_wt_1862 |
| 2077651 | G | | | | | | C/G | cds_wt_1862 |
| 2077652 | A | | | | | | G/A | cds_wt_1862 |
| 2077654 | A | | | | | | G/A | cds_wt_1862 |
| 2077663 | C | | | | | | A/C | cds_wt_1862 |
| 2077669 | G | | | | | | C/G | cds_wt_1862 |
| 2077671 | T | | | | | | C/T | cds_wt_1862 |
| 2077682 | C | | | | | | G/C | cds_wt_1862 |
| 2077688 | G | | | | | | A/G | cds_wt_1862 |
| 2077691 | C | | | | | | G/C | cds_wt_1862 |
| 2077694 | A | | | | | | C/A | cds_wt_1862 |
| 2077697 | G | | | | | | C/G | cds_wt_1862 |
| 2077703 | T | | | | | | G/T | cds_wt_1862 |
| 2077715 | G | | | | | | A/G | cds_wt_1862 |
| 2077724 | A | | | | | | G/A | cds_wt_1862 |
| 2077726 | C | | | | | | T/C | cds_wt_1862 |
| 2077730 | G | | | | | | C/G | cds_wt_1862 |
| 2077733 | G | | | | | | A/G | cds_wt_1862 |
| 2077736 | C | | | | | | C/T | cds_wt_1862 |
| 2077742 | G | | | | | | C/G | cds_wt_1862 |
| 2077745 | A | | | | | | G/A | cds_wt_1862 |
| 2077751 | G | | | | | | A/G | cds_wt_1862 |
| 2077762 | T | | | | | | C/T | cds_wt_1862 |
| 2077769 | T | | | | | | C/T | cds_wt_1862 |
| 2077772 | A | | | | | | G/A | cds_wt_1862 |
| 2077775 | G | | | | | | A/G | cds_wt_1862 |
| 2077793 | G | | | | | | C/G | cds_wt_1862 |
| 2077794 | A | | | | | | G/A | cds_wt_1862 |
| 2077795 | C | | | | | | T/C | cds_wt_1862 |
| 2077805 | C | | | | | | T/C | cds_wt_1862 |
| 2080486 | C | | | | | | T | cds_wt_1864 |
| 2086608 | G | | A | A | A | A | A | cds_wt_1866 |
| 2096915 | G | | A | A | A | A | A | cds_wt_1878 |
| 2098836 | C | T | T | T | T | T | T | cds_wt_1880 |
| 2099830 | G | | | | | | A | cds_wt_1880 |
| 2126265 | C | | T | T | T | T | T | — |
| 2131730 | G | | A | A | A | A | A | cds_wt_1909 |
| 2135109 | C | | | | | | T | cds_wt_1912 |
| 2136848 | C | | T | T | T | T | T | — |
| 2144528 | G | A | A | A | A | A | A | cds_wt_1918 |
| 2147486 | G | | A | A | A | A | A | cds_wt_1921 |
| 2154132 | C | T | T | T | T | T | T | cds_wt_1927 |
| 2154136 | C | T | T | T | T | T | T | cds_wt_1927 |
| 2188490 | C | | | | T | T | T | cds_wt_1959 |
| 2191494 | C | T | T | T | T | T | T | cds_wt_1960 |
| 2199567 | G | | A | A | A | A | A | cds_wt_1969 |
| 2208975 | G | A | A | A | A | A | A | cds_wt_1977 |
| 2212324 | G | | | | A | A | A | cds_wt_1979 |
| 2212659 | G | | A | A | A | A | A | cds_wt_1980 |
| 2230643 | G | | A | A | A | A | A | cds_wt_1996 |
| 2235434 | G | | A | A | A | A | A | cds_wt_2000 |
| 2250499 | C | T | T | T | T | T | T | cds_wt_2012 |
| 2259118 | C | | | T | T | | T | cds_wt_2019 |
| 2260582 | G | | | | | | A | cds_wt_2019 |
| 2266821 | C | T | T | | T | T | T | cds_wt_2023 |
| 2271223 | G | A | A | A | A | A | A | cds_wt_2027 |
| 2273696 | C | T | T | T | T | T | T | — |
| 2277990 | C | T | | | | | T | cds_wt_2031 |
| 2291798 | C | | T | T | T | T | T | cds_wt_2032 |
| 2293101 | C | | | | | | C/T | cds_wt_2033 |
| 2293102 | G | | | | | | G/T | cds_wt_2033 |
| 2293121 | G | C/G | C/G | C/G | C/G | C/G | G/C | cds_wt_2033 |
| 2293139 | A | C/A | C/A | C/A | C/A | C/A | A/C | cds_wt_2033 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 2293157 | G | G/A | G/A | G/A | G/A | G/A | G/A | cds_wt_2033 |
| 2293169 | G | | | | | | G/C | cds_wt_2033 |
| 2293175 | G | | | | | | G/A | cds_wt_2033 |
| 2293176 | A | | | | | | A/T | cds_wt_2033 |
| 2293184 | C | | | | | | C/G | cds_wt_2033 |
| 2293185 | G | | | | | | G/A | cds_wt_2033 |
| 2293187 | A | | | | | | A/G | cds_wt_2033 |
| 2293196 | G | | | | | | A/G | cds_wt_2033 |
| 2293202 | G | | | | | | G/C | cds_wt_2033 |
| 2293205 | G | | | | | | C/G | cds_wt_2033 |
| 2293214 | G | | | | | | G/C | cds_wt_2033 |
| 2293219 | A | | | | | | A/T | cds_wt_2033 |
| 2293220 | G | | | | | | G/C | cds_wt_2033 |
| 2293226 | G | | | | | | C/G | cds_wt_2033 |
| 2293228 | G | | | | | | G/A | cds_wt_2033 |
| 2293234 | A | | | | | | A/T | cds_wt_2033 |
| 2293235 | G | | | | | | G/C | cds_wt_2033 |
| 2293238 | G | | | | | | G/C | cds_wt_2033 |
| 2293244 | G | | | | | | G/C | cds_wt_2033 |
| 2293247 | G | | | | | | A/G | cds_wt_2033 |
| 2293253 | G | G/A | A | G/A | G/A | A/G | A/G | cds_wt_2033 |
| 2293268 | G | G/C | C | C | C | C | C/G | cds_wt_2033 |
| 2293310 | G | | | | | | G/A | cds_wt_2033 |
| 2293313 | G | | | | | | G/C | cds_wt_2033 |
| 2293316 | G | | | | | | G/A | cds_wt_2033 |
| 2293319 | G | | | | | | G/A | cds_wt_2033 |
| 2293328 | G | | | | | | G/C | cds_wt_2033 |
| 2293337 | G | | | | | | G/C | cds_wt_2033 |
| 2293346 | G | | | | | | G/C | cds_wt_2033 |
| 2293352 | C | | | | | | C/G | cds_wt_2033 |
| 2293367 | G | G/C | C/G | G/C | | | G/C | cds_wt_2033 |
| 2293376 | C | G/C | G/C | C/G | C/G | C/G | C/G | cds_wt_2033 |
| 2293403 | C | | | | | | C/G | cds_wt_2033 |
| 2293463 | C | | | | | | C/G | cds_wt_2033 |
| 2302130 | G | | | | | | A | cds_wt_2039 |
| 2312744 | C | | | | | T | T | cds_wt_2051 |
| 2313183 | G | | | A | A | | A | cds_wt_2051 |
| 2315988 | C | T | T | T | T | T | T | cds_wt_2052 |
| 2323085 | C | T | T | T | T | T | T | cds_wt_2057 |
| 2329242 | C | T | T | T | T | T | T | cds_wt_2063 |
| 2332081 | G | | A | A | A | A | A | cds_wt_2066 |
| 2341627 | C | | | | T | | T | cds_wt_2073 |
| 2347673 | C | T | T | T | T | T | T | cds_wt_2076 |
| 2348681 | G | A | A | A | A | A | A | cds_wt_2077 |
| 2359598 | G | | A | A | A | A | A | cds_wt_2088 |
| 2362060 | A | | | | | | G | cds_wt_2091 |
| 2368326 | G | | | | | A | A | cds_wt_2097 |
| 2376154 | G | A | A | A | A | A | A | cds_wt_2107 |
| 2380176 | C | | T | T | T | T | T | cds_wt_2113 |
| 2382542 | C | | T | T | T | T | T | cds_wt_2115 |
| 2382567 | C | | T | T | T | T | T | cds_wt_2115 |
| 2382748 | C | T | T | T | T | T | T | — |
| 2389975 | C | | | | T | T | T | — |
| 2392147 | C | | | | T | T | T | cds_wt_2122 |
| 2396255 | G | | | | | A | A | cds_wt_2123 |
| 2415101 | G | | A | A | A | | A | cds_wt_2140 |
| 2422620 | C | | | | T | T | T | cds_wt_2147 |
| 2437185 | G | | A | A | A | A | A | cds_wt_2158 |
| 2448470 | G | | A | A | A | A | A | cds_wt_2169 |
| 2452760 | G | | A | A | A | A | A | cds_wt_2173 |
| 2456608 | C | | | | T | T | T | cds_wt_2175 |
| 2459347 | C | | | | T | T | T | cds_wt_2177 |
| 2459641 | G | | | | | A | A | cds_wt_2178 |
| 2460824 | C | | | | T | T | T | cds_wt_2180 |
| 2463427 | C | | | | | | T | cds_wt_2182 |
| 2482048 | C | T | T | T | T | T | T | cds_wt_2197 |
| 2482381 | G | A | A | A | A | A | A | cds_wt_2197 |
| 2483453 | C | | T | T | T | T | T | cds_wt_2199 |
| 2487377 | G | A | A | A | A | A | A | cds_wt_2203 |
| 2489641 | G | | A | A | A | A | A | cds_wt_2206 |
| 2492054 | G | | | | | A | A | — |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 2502775 | G | | | | | A | A | — |
| 2515457 | G | | | | | A | A | cds_wt_2228 |
| 2518872 | G | | | A | A | A | A | cds_wt_2232 |
| 2530466 | G | | A | A | A | A | A | cds_wt_2252 |
| 2532233 | G | | A | A | A | A | A | cds_wt_2256 |
| 2533237 | G | | A | A | A | A | A | cds_wt_2259 |
| 2536306 | G | | A | A | A | A | A | — |
| 2538874 | G | | A | A | A | A | A | cds_wt_2265 |
| 2542087 | G | | A | A | A | A | A | cds_wt_2270 |
| 2544720 | C | | | | | T | T | cds_wt_2270 |
| 2553277 | G | | | | | | A | cds_wt_2277 |
| 2556662 | C | | | | | T | T | cds_wt_2283 |
| 2559280 | G | A | A | A | A | A | A | — |
| 2562212 | G | | | | | A | A | cds_wt_2288 |
| 2564253 | G | | | | | A | A | — |
| 2564620 | G | | | | | A | A | — |
| 2566353 | G | | | | | A | A | cds_wt_2290 |
| 2572994 | G | | A | A | A | A | A | cds_wt_2297 |
| 2573153 | C | | T | T | T | T | T | cds_wt_2297 |
| 2575327 | G | | | | A | | A | cds_wt_2299 |
| 2599645 | G | | | | | A | A | cds_wt_2323 |
| 2599894 | G | | | | | A | A | cds_wt_2324 |
| 2601319 | G | | | | | A | A | cds_wt_2324 |
| 2606340 | G | | | | | A | A | cds_wt_2330 |
| 2608948 | G | | | | | A | A | cds_wt_2334 |
| 2610422 | C | | | | | T | T | — |
| 2614778 | G | | | | | | A | cds_wt_2339 |
| 2617082 | G | | | | | A | A | cds_wt_2340 |
| 2618776 | C | | T | T | T | T | T | cds_wt_2342 |
| 2618805 | C | | T | T | T | T | T | cds_wt_2342 |
| 2620558 | G | | | | | A | A | cds_wt_2344 |
| 2626414 | A | | | G | G | G | G | cds_wt_2350 |
| 2636037 | C | | | | | T | T | cds_wt_2357 |
| 2639682 | G | | | | | A | A | cds_wt_2361 |
| 2642753 | G | | A | A | A | A | A | cds_wt_2364 |
| 2644984 | C | | | | | T | T | cds_wt_2364 |
| 2651718 | C | | T | T | T | T | T | cds_wt_2367 |
| 2652733 | C | | | | | T | T | cds_wt_2368 |
| 2653074 | C | | | | | T | T | cds_wt_2368 |
| 2653159 | C | T | T | T | T | T | T | cds_wt_2368 |
| 2653337 | G | | A | A | A | A | A | cds_wt_2369 |
| 2655271 | C | | | | | | T | cds_wt_2371 |
| 2655308 | C | | | | | | T | cds_wt_2371 |
| 2657059 | C | | | | | T | T | cds_wt_2371 |
| 2658261 | G | | | | | A | A | cds_wt_2372 |
| 2659295 | C | | | | | T | T | cds_wt_2373 |
| 2663775 | C | | | | | T | T | cds_wt_2376 |
| 2670944 | C | | | | | T | T | cds_wt_2378 |
| 2671043 | C | | | | | T | T | cds_wt_2378 |
| 2672551 | C | | | | | T | T | cds_wt_2380 |
| 2676880 | C | T | T | T | T | T | T | cds_wt_2382 |
| 2677056 | G | | A | A | A | A | A | cds_wt_2382 |
| 2677196 | C | T | T | T | T | T | T | cds_wt_2382 |
| 2678066 | G | | A | A | A | A | A | cds_wt_2382 |
| 2679900 | C | | | | | T | T | cds_wt_2383 |
| 2686364 | C | | | | | T | T | cds_wt_2390 |
| 2687028 | C | | | | | T | T | cds_wt_2391 |
| 2688632 | C | | | | | T | T | cds_wt_2392 |
| 2694405 | G | | | | | | A | cds_wt_2396 |
| 2701281 | G | | | | | A | A | cds_wt_2403 |
| 2712327 | G | | | | | A | A | — |
| 2720850 | C | T | T | T | T | T | T | cds_wt_2418 |
| 2728435 | G | | | | | A | A | cds_wt_2425 |
| 2731397 | G | | A | A | A | A | A | cds_wt_2428 |
| 2735550 | G | G/A | G/A | G/A | G/A | G/A | G/A | — |
| 2735576 | G | | | | | | G/C | — |
| 2738768 | C | | | T | T | T | T | cds_wt_2433 |
| 2744600 | C | T | T | T | T | T | T | cds_wt_2438 |
| 2748694 | C | T | T | T | T | T | T | cds_wt_2442 |
| 2756873 | C | | T | T | T | T | T | cds_wt_2449 |
| 2760595 | G | | | | | A | A | — |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 2762887 | G | | | A | A | A | A | cds_wt_2453 |
| 2763137 | G | | A | A | A | A | A | cds_wt_2453 |
| 2764279 | C | | T | T | T | T | T | cds_wt_2454 |
| 2766645 | C | | | T | T | T | T | cds_wt_2456 |
| 2770562 | C | | | | | T | T | — |
| 2773173 | C | T | T | T | T | T | T | cds_wt_2462 |
| 2774095 | G | | A | A | A | A | A | cds_wt_2464 |
| 2774734 | G | | A | A | A | A | A | cds_wt_2465 |
| 2774874 | G | | A | A | A | A | A | cds_wt_2465 |
| 2776314 | C | | | | | T | T | cds_wt_2466 |
| 2776919 | C | | T | T | T | T | T | cds_wt_2467 |
| 2778598 | G | | | | | A | A | cds_wt_2468 |
| 2779539 | G | | | | | A | A | — |
| 2782696 | C | | | | | T | T | cds_wt_2473 |
| 2783578 | C | | | | | T | T | — |
| 2783738 | C | | | | | T | T | cds_wt_2474 |
| 2785372 | C | | | | | T | T | cds_wt_2475 |
| 2785531 | C | | | | | T | T | cds_wt_2475 |
| 2787379 | G | | A | A | A | A | A | cds_wt_2476 |
| 2788015 | C | | | | | T | T | cds_wt_2477 |
| 2788247 | C | | | | | T | T | cds_wt_2477 |
| 2789216 | C | | T | T | T | T | T | cds_wt_2478 |
| 2790626 | C | | T | T | T | T | T | cds_wt_2479 |
| 2791577 | C | | | | | T | T | cds_wt_2480 |
| 2792510 | C | | | | | T | T | cds_wt_2481 |
| 2792715 | G | A | A | A | A | A | A | cds_wt_2481 |
| 2797814 | C | T | T | T | T | T | T | cds_wt_2487 |
| 2799953 | C | | T | T | T | T | T | cds_wt_2489 |
| 2800033 | C | | | | | T | T | cds_wt_2489 |
| 2802765 | C | | | | | T | T | — |
| 2803789 | C | | T | T | T | T | T | cds_wt_2493 |
| 2804694 | C | | T | T | T | T | T | cds_wt_2494 |
| 2806670 | C | | T | T | T | T | T | cds_wt_2496 |
| 2814611 | G | | | | | | A | — |
| 2815199 | C | | | | | | C/T | cds_wt_2502 |
| 2816239 | G | | | | | | A | cds_wt_2503 |
| 2821693 | G | | | | A | A | A | cds_wt_2509 |
| 2838356 | C | | | | | T | T | — |
| 2841171 | T | | | | | | T/A | cds_wt_2526 |
| 2841177 | C | | | | | | C/G | cds_wt_2526 |
| 2841183 | C | | | | | | C/G | cds_wt_2526 |
| 2841213 | T | | | | | | T/C | cds_wt_2526 |
| 2841228 | C | | | | | | C/G | cds_wt_2526 |
| 2841237 | G | | | | | | G/C | cds_wt_2526 |
| 2841251 | G | | | | | | G/T | cds_wt_2526 |
| 2841255 | C | | | | | | C/G | cds_wt_2526 |
| 2841258 | G | | | | | | G/T | cds_wt_2526 |
| 2841276 | C | G/C | | G | G | G | C/G | cds_wt_2526 |
| 2841293 | C | | | | | | C/G | cds_wt_2526 |
| 2841297 | C | | | | | | C/A | cds_wt_2526 |
| 2841303 | C | | | | | | C/T | cds_wt_2526 |
| 2841306 | G | | | | | | G/A | cds_wt_2526 |
| 2841312 | T | | | | | | C/T | cds_wt_2526 |
| 2841315 | C | | | | | | G/C | cds_wt_2526 |
| 2841322 | A | | | | | | A/T | cds_wt_2526 |
| 2841323 | G | | | | | | G/T | cds_wt_2526 |
| 2841327 | C | | | | | | G/C | cds_wt_2526 |
| 2841335 | G | | | | | | C/G | cds_wt_2526 |
| 2841357 | G | | | | | | C/G | cds_wt_2526 |
| 2841360 | G | | | | | | C/G | cds_wt_2526 |
| 2841369 | G | | | | | | C/G | cds_wt_2526 |
| 2841376 | T | | | | | | T/C | cds_wt_2526 |
| 2841377 | G | | | | | | T/G | cds_wt_2526 |
| 2841384 | G | | | | | | C/G | cds_wt_2526 |
| 2841389 | T | | | | | | T/C | cds_wt_2526 |
| 2841397 | G | | | | | | G/T | cds_wt_2526 |
| 2841398 | A | | | | | | C/A | cds_wt_2526 |
| 2841402 | G | | | | | | A/G | cds_wt_2526 |
| 2841403 | G | | | | | | C/G | cds_wt_2526 |
| 2841409 | T | | | | | | A/T | cds_wt_2526 |
| 2841413 | G | | | | | | T/G | cds_wt_2526 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 2841423 | C | | | | | | G/C | cds_wt_2526 |
| 2841444 | G | | | | | | C/G | cds_wt_2526 |
| 2841451 | C | | | | | | T/C | cds_wt_2526 |
| 2841477 | C | | | | | | G/C | cds_wt_2526 |
| 2841514 | G | | | | | | T/G | cds_wt_2526 |
| 2841531 | A | | | | | | G/A | cds_wt_2526 |
| 2841534 | G | | | | | | C/G | cds_wt_2526 |
| 2841536 | T | | | | | | A/T | cds_wt_2526 |
| 2841540 | C | | | | | | C/G | cds_wt_2526 |
| 2841546 | G | | | | | | C/G | cds_wt_2526 |
| 2841552 | G | | | | | | C | cds_wt_2526 |
| 2841554 | T | | | | | | C/T | cds_wt_2526 |
| 2841555 | C | | | | | | T/C | cds_wt_2526 |
| 2841562 | C | | | | | | T/C | cds_wt_2526 |
| 2841563 | A | | | | | | C/A | cds_wt_2526 |
| 2841569 | A | | | | | | C/A/T | cds_wt_2526 |
| 2841575 | C | | | | | | T/C | cds_wt_2526 |
| 2841585 | C | | | | | | C/G | cds_wt_2526 |
| 2841588 | G | | | | | | C/G | cds_wt_2526 |
| 2841594 | G | | | | | | A/G | cds_wt_2526 |
| 2841605 | C | | | | | | C/A | cds_wt_2526 |
| 2841609 | C | | | | | | C/G | cds_wt_2526 |
| 2841617 | T | | | | | | G/T | cds_wt_2526 |
| 2841636 | G | C | | C | C | | C/G | cds_wt_2526 |
| 2841656 | A | | | | | | C/A | cds_wt_2526 |
| 2841660 | G | | | | | | C/G | cds_wt_2526 |
| 2841668 | C | | | | | | T/C | cds_wt_2526 |
| 2841690 | G | | | | | | C/G | — |
| 2841700 | G | | | | | | T | — |
| 2841701 | C | | | | | | T | — |
| 2841708 | G | | | | | | A/G | — |
| 2841734 | T | | | | | | C | — |
| 2841735 | C | | | | | | T | — |
| 2841738 | G | | | | | | C | — |
| 2841744 | C | | | | | | G/C | — |
| 2841747 | G | | | | | | A | — |
| 2841756 | C | | | | | | G | — |
| 2841759 | G | | | | | | C | — |
| 2841762 | C | | | | | | G | — |
| 2841776 | G | | | | | | T | — |
| 2841778 | T | | | | | | G | — |
| 2841783 | G | | | | | | C | — |
| 2841786 | A | | | | | | T | — |
| 2841789 | C | | | | | | T | — |
| 2845157 | G | | A | A | A | A | A | cds_wt_2528 |
| 2850318 | G | | | A | A | A | A | cds_wt_2533 |
| 2851372 | G | | | | | | A | cds_wt_2534 |
| 2853353 | C | | T | T | T | T | T | cds_wt_2535 |
| 2853817 | G | | | | | | A | cds_wt_2535 |
| 2868405 | C | T | T | T | T | T | T | cds_wt_2548 |
| 2874011 | C | | T | T | T | T | T | cds_wt_2551 |
| 2875055 | G | | A | A | A | A | A | — |
| 2875488 | G | | | | A | A | A | — |
| 2876911 | G | A | | | | | A | cds_wt_2553 |
| 2882407 | C | | T | T | T | T | T | cds_wt_2558 |
| 2888545 | C | | T | T | T | T | T | cds_wt_2562 |
| 2890510 | C | T | T | T | T | T | T | cds_wt_2565 |
| 2892791 | G | | | | | | A | cds_wt_2566 |
| 2896239 | G | A | | | | | A | cds_wt_2568 |
| 2896828 | G | A | A | A | A | A | A | cds_wt_2568 |
| 2896833 | G | A | A | A | A | A | A | cds_wt_2568 |
| 2899845 | C | T | T | T | T | T | T | — |
| 2899865 | C | T | T | T | T | T | T | — |
| 2901123 | C | | T | T | T | T | T | cds_wt_2572 |
| 2905469 | C | | T | T | T | T | T | cds_wt_2574 |
| 2912026 | G | A | A | A | A | A | A | cds_wt_2580 |
| 2921100 | C | | | | | T | T | cds_wt_2587 |
| 2934976 | G | A | A | A | A | A | A | — |
| 2935134 | G | | | | | | A | — |
| 2935223 | G | | | | A | A | A | — |
| 2945715 | G | | A | A | A | A | A | cds_wt_2611 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 2953167 | C | T | T | T | T | T | T | cds_wt_2616 |
| 2956464 | C | T | T | T | T | T | T | cds_wt_2620 |
| 2965167 | G | | | | | | A | cds_wt_2630 |
| 2971031 | C | T | T | T | T | T | T | cds_wt_2633 |
| 2971761 | C | T | T | T | T | T | T | cds_wt_2633 |
| 2973653 | C | T | T | T | T | T | T | cds_wt_2634 |
| 2976296 | C | T | | | | | T | cds_wt_2637 |
| 2978371 | C | T | T | T | T | T | T | cds_wt_2638 |
| 2983351 | G | | A | A | A | A | A | cds_wt_2644 |
| 2986416 | C | T | T | T | T | T | T | cds_wt_2649 |
| 2987675 | C | T | T | T | T | T | T | cds_wt_2650 |
| 2988967 | C | T | T | T | T | T | T | cds_wt_2650 |
| 2992035 | C | | | | | T | T | cds_wt_2651 |
| 2993614 | A | | | | | | G | cds_wt_2652 |
| 2994097 | G | A | A | A | A | A | A | cds_wt_2652 |
| 3000921 | G | A | A | A | A | A | A | cds_wt_2658 |
| 3002748 | G | | | | A | A | A | cds_wt_2659 |
| 3003382 | G | | | | A | A | A | — |
| 3005352 | G | | | | A | A | A | cds_wt_2662 |
| 3006201 | C | | | | T | | T | cds_wt_2662 |
| 3021497 | G | | A | A | A | A | A | cds_wt_2674 |
| 3026718 | C | | | | | T | T | — |
| 3027132 | G | | | | A | A | A | — |
| 3031683 | C | | T | T | T | T | T | — |
| 3032969 | C | | T | T | T | T | T | — |
| 3044082 | G | | | | | | A | cds_wt_2679 |
| 3045579 | G | A | A | A | A | A | A | cds_wt_2679 |
| 3049857 | G | | | | | | A | cds_wt_2681 |
| 3066905 | C | | | | | T | T | cds_wt_2697 |
| 3079916 | T | | | | | | A/T | — |
| 3079923 | C | | | | | | C/T | — |
| 3079936 | G | | | | | | A/G | — |
| 3079950 | A | T/A | | | | | T/A | — |
| 3080004 | C | | | | | | C/T | — |
| 3080006 | A | | | | | | T/A | — |
| 3080035 | C | C/T | | | | | C/T | cds_wt_2713 |
| 3080043 | A | C/A | C/A | C/A | C/A | C/A | C/A | cds_wt_2713 |
| 3080063 | G | C/G | C/G | C/G | C/G | C/G | C/G | cds_wt_2713 |
| 3080084 | C | C/T | C/T | C/T | C/T | C/T | C/T | cds_wt_2713 |
| 3080087 | G | G/C/T | G/C/T | C/G/T | G/C/T | G/T/C | C/T/G | cds_wt_2713 |
| 3080098 | C | | | | | C/A | C/A | cds_wt_2713 |
| 3080128 | C | | | | | T/C | T/C | cds_wt_2713 |
| 3080136 | A | | | | | G/A | G/A | cds_wt_2713 |
| 3080160 | C | | | | | | G/C | cds_wt_2713 |
| 3080161 | T | | | | | | C/T | cds_wt_2713 |
| 3080163 | T | | | | | | C/T | cds_wt_2713 |
| 3080183 | T | T/C | T/C | T/C | T/C | T/C | C/T | cds_wt_2713 |
| 3080192 | G | C/G | C/G | C/G | C/G | C/G | C/G | cds_wt_2713 |
| 3080204 | G | C/G | C/G | C/G | C/G | C/G | C/G | cds_wt_2713 |
| 3080237 | G | | | | | | C/G | cds_wt_2713 |
| 3080288 | G | | | | | | C/G | cds_wt_2713 |
| 3080294 | G | | | | | | T/G | cds_wt_2713 |
| 3080316 | C | | | | | | C/T | — |
| 3080321 | T | T/C | T/C | T/C | T/C | T/C | — |  |
| 3080325 | G | G/T | G/T | G/T | G/T | G/T | T/G | — |
| 3080326 | C | C/T | C/T | C/T | C/T | C/T | T/C | — |
| 3080355 | A | A/T | A/T | A/T | A/T | A/T | T/A | — |
| 3080356 | A | | | | | | A/G | — |
| 3080357 | A | A/G | A/G | A/G | A/G | A/G | A/G | — |
| 3080359 | A | | | | | | A/G | — |
| 3080372 | A | A/G | A/G | A/G | A/G | A/G | A/G | — |
| 3080375 | A | | | | | | A/C | — |
| 3080382 | G | | | | | | G/A | — |
| 3080391 | A | | | | | | A/G | — |
| 3080393 | C | | | | | | C/T | — |
| 3080394 | G | | | | | | G/A | — |
| 3080402 | A | | | | | | A/G | — |
| 3080406 | A | | | | | | A/G | — |
| 3080418 | A | | | | | | A/G | — |
| 3080447 | C | | | | | | C/T | — |
| 3080465 | T | | | | | | T/C | — |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 3080472 | C | | | | | | C/T | — |
| 3080482 | A | | | | | | A/G | — |
| 3080485 | C | | | | | | C/T | — |
| 3080496 | T | | | | | | T/C | — |
| 3082062 | G | | | | | | A | — |
| 3084014 | G | A | A | A | A | A | A | cds_wt_2717 |
| 3087970 | C | | T | T | T | T | T | cds_wt_2721 |
| 3089578 | G | | A | A | A | A | | — |
| 3090231 | G | | | | | | G/C | cds_wt_2723 |
| 3101153 | G | | A | A | A | A | A | cds_wt_2729 |
| 3120006 | C | | | T | T | T | T | — |
| 3121040 | C | | T | T | T | T | T | — |
| 3125035 | C | | T | T | T | T | T | cds_wt_2746 |
| 3125407 | C | | | | | | T | cds_wt_2746 |
| 3128098 | C | | T | T | T | T | T | cds_wt_2749 |
| 3131738 | C | | T | T | T | T | T | cds_wt_2753 |
| 3133651 | C | | T | T | T | T | T | cds_wt_2755 |
| 3133766 | G | A | A | A | A | A | A | cds_wt_2755 |
| 3137673 | C | | | | | | T | cds_wt_2759 |
| 3138173 | G | A | A | A | A | A | A | cds_wt_2760 |
| 3147694 | C | | | T | T | T | T | cds_wt_2765 |
| 3148142 | C | | T | T | T | T | T | cds_wt_2766 |
| 3148342 | C | | T | T | T | T | T | cds_wt_2766 |
| 3148452 | C | | T | T | T | T | T | cds_wt_2766 |
| 3148777 | C | | T | T | T | T | T | cds_wt_2766 |
| 3148960 | C | | T | T | T | T | T | cds_wt_2766 |
| 3149335 | C | | T | T | T | T | T | cds_wt_2766 |
| 3151547 | C | | | | | | T | — |
| 3152279 | C | | T | T | T | T | T | — |
| 3153365 | G | A | A | A | A | A | A | — |
| 3156844 | C | | | | T | T | T | cds_wt_2777 |
| 3175067 | G | A | A | A | A | A | A | cds_wt_2796 |
| 3176311 | C | | T | | | T | T | cds_wt_2797 |
| 3180510 | C | | | T | T | T | T | cds_wt_2801 |
| 3181134 | C | | T | T | T | T | T | cds_wt_2803 |
| 3196810 | C | | | | | | T | cds_wt_2815 |
| 3198674 | G | A | A | A | A | A | A | cds_wt_2817 |
| 3203788 | G | | | | | | A | cds_wt_2823 |
| 3204764 | G | | | | | | A | cds_wt_2823 |
| 3208464 | G | | | A | A | A | A | cds_wt_2826 |
| 3213080 | C | | T | T | T | T | T | cds_wt_2831 |
| 3214059 | C | | | | | T | T | cds_wt_2832 |
| 3216019 | C | | | T | T | | T | cds_wt_2834 |
| 3216133 | C | | | | | | T | cds_wt_2834 |
| 3218109 | C | | | T | T | T | T | cds_wt_2834 |
| 3226281 | C | | | | | T | T | cds_wt_2841 |
| 3229241 | G | | | | A | A | A | cds_wt_2845 |
| 3230387 | G | | | | A | A | A | cds_wt_2847 |
| 3235932 | C | | T | T | T | T | T | cds_wt_2851 |
| 3237109 | C | T | T | T | T | T | T | cds_wt_2851 |
| 3238700 | C | | T | T | T | T | T | cds_wt_2854 |
| 3241279 | C | | T | T | T | T | T | cds_wt_2857 |
| 3241643 | G | | | | A | A | A | cds_wt_2857 |
| 3245145 | C | | | | T | T | T | cds_wt_2860 |
| 3247705 | G | | A | A | A | A | A | cds_wt_2861 |
| 3248186 | G | | A | A | A | A | A | cds_wt_2862 |
| 3249319 | C | | T | T | T | T | T | cds_wt_2862 |
| 3251559 | G | | A | A | A | A | A | — |
| 3253347 | C | | T | T | T | T | T | — |
| 3253453 | C | | T | T | T | T | T | cds_wt_2867 |
| 3253884 | G | | | | A | A | A | — |
| 3254464 | G | | | | A | A | A | — |
| 3258028 | G | | A | A | A | A | A | cds_wt_2872 |
| 3258094 | G | | A | A | | A | A | — |
| 3258637 | C | | T | T | T | T | T | — |
| 3259667 | C | | | T | T | | T | cds_wt_2874 |
| 3261792 | G | | | A | A | A | A | cds_wt_2876 |
| 3262978 | C | T | T | T | T | T | T | cds_wt_2876 |
| 3266668 | G | | A | A | A | A | A | cds_wt_2879 |
| 3266806 | C | T | T | T | T | T | T | cds_wt_2879 |
| 3267341 | G | | | A | A | A | A | cds_wt_2880 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 3267927 | C | | T | T | T | T | T | cds_wt_2880 |
| 3268140 | T | | C | C | C | C | C | cds_wt_2880 |
| 3269676 | G | | A | A | A | A | A | cds_wt_2882 |
| 3270548 | G | | | A | A | A | A | cds_wt_2882 |
| 3275254 | A | | G | G | G | G | G | cds_wt_2885 |
| 3276870 | C | | T | T | T | T | T | cds_wt_2888 |
| 3277187 | C | T | T | T | T | T | T | — |
| 3279932 | C | | T | T | T | T | T | — |
| 3285105 | C | | T | T | T | T | T | cds_wt_2902 |
| 3289175 | C | | | | | | T | cds_wt_2903 |
| 3289533 | C | | | T | T | T | T | cds_wt_2903 |
| 3290417 | G | | | A | | | A | cds_wt_2904 |
| 3290880 | C | | | T | T | T | T | — |
| 3291408 | C | T | T | T | T | T | T | cds_wt_2906 |
| 3294618 | C | | T | T | T | T | T | cds_wt_2909 |
| 3295292 | C | | T | T | T | T | T | — |
| 3296150 | C | | T | T | T | T | T | — |
| 3296689 | C | | T | T | T | T | T | cds_wt_2910 |
| 3297254 | C | | T | T | T | T | T | cds_wt_2910 |
| 3297593 | G | | | | | | A | cds_wt_2910 |
| 3297802 | C | | T | T | T | T | T | cds_wt_2910 |
| 3297816 | G | | | | | | A | cds_wt_2910 |
| 3299219 | C | | T | T | T | T | T | — |
| 3300457 | C | | T | T | T | T | T | cds_wt_2914 |
| 3300838 | C | T | | T | T | T | T | cds_wt_2914 |
| 3300849 | C | T | T | T | T | T | T | cds_wt_2914 |
| 3307410 | G | | A | A | A | A | A | — |
| 3307738 | G | | A | A | A | A | A | — |
| 3309205 | C | | T | T | T | T | T | cds_wt_2919 |
| 3309441 | G | | | | | | A | cds_wt_2919 |
| 3313410 | C | | T | T | T | T | T | cds_wt_2923 |
| 3314734 | C | | T | T | T | T | T | cds_wt_2925 |
| 3315483 | C | | T | T | T | T | T | cds_wt_2925 |
| 3316995 | C | | | | | | T | cds_wt_2926 |
| 3318906 | C | | T | T | T | T | T | cds_wt_2927 |
| 3319964 | C | | | T | T | T | T | cds_wt_2928 |
| 3321895 | G | | A | A | A | A | A | cds_wt_2929 |
| 3326784 | G | | A | A | A | A | A | cds_wt_2933 |
| 3327191 | G | | A | A | A | A | A | cds_wt_2934 |
| 3328753 | C | | T | T | T | T | T | cds_wt_2934 |
| 3336319 | C | | T | T | T | T | T | cds_wt_2941 |
| 3337206 | G | | | | | A | A | cds_wt_2941 |
| 3338688 | C | | T | T | T | T | T | cds_wt_2943 |
| 3345311 | C | | T | T | T | T | T | cds_wt_2947 |
| 3346757 | G | | | | | A | A | cds_wt_2947 |
| 3347355 | C | | | | T | T | T | cds_wt_2947 |
| 3347540 | C | | | | T | T | T | cds_wt_2947 |
| 3347560 | C | | | | T | T | T | cds_wt_2947 |
| 3348860 | C | | T | T | T | T | T | — |
| 3349015 | C | | | | T | T | T | cds_wt_2949 |
| 3349651 | C | | | | T | T | T | cds_wt_2949 |
| 3350820 | C | | T | T | T | T | T | cds_wt_2951 |
| 3351613 | C | | T | T | T | T | T | cds_wt_2953 |
| 3353030 | C | | | T | T | T | T | cds_wt_2954 |
| 3354271 | C | | | | T | T | T | cds_wt_2954 |
| 3354637 | C | | | | T | T | T | cds_wt_2955 |
| 3358411 | G | | | | | | G/A | — |
| 3358883 | G | | | | | A | A | — |
| 3361525 | G | A | A | A | A | A | A | cds_wt_2960 |
| 3363657 | C | | T | T | T | T | T | — |
| 3368167 | C | | T | T | T | T | T | — |
| 3368381 | C | | | | | | C/T | cds_wt_2966 |
| 3375301 | C | | T | T | T | T | T | cds_wt_2971 |
| 3381507 | C | | | | | | T | cds_wt_2978 |
| 3383846 | C | | T | T | T | T | T | cds_wt_2982 |
| 3386322 | C | | | T | T | T | T | cds_wt_2985 |
| 3386914 | G | | A | A | A | A | A | cds_wt_2986 |
| 3388650 | C | | T | T | T | T | T | cds_wt_2988 |
| 3388663 | C | | | T | T | T | T | cds_wt_2988 |
| 3388840 | G | A | A | A | A | A | A | cds_wt_2988 |
| 3390202 | G | | | A | A | A | A | cds_wt_2990 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 3391187 | C | | T | T | T | T | T | cds_wt_2991 |
| 3394129 | C | | T | T | T | T | T | cds_wt_2995 |
| 3395838 | C | | T | T | T | T | T | cds_wt_2996 |
| 3396692 | C | | | | | | T | cds_wt_2997 |
| 3397717 | C | | T | T | T | T | T | cds_wt_2998 |
| 3400152 | C | | T | T | T | T | T | cds_wt_3000 |
| 3402866 | G | | A | A | A | A | A | cds_wt_3004 |
| 3403044 | C | | | | | T | T | cds_wt_3004 |
| 3403253 | C | | T | T | T | T | T | cds_wt_3004 |
| 3404959 | C | | T | T | T | T | T | cds_wt_3006 |
| 3405078 | C | T | T | T | T | T | T | — |
| 3409620 | G | | | | A | | A | cds_wt_3009 |
| 3412544 | G | | A | A | A | A | A | cds_wt_3012 |
| 3415574 | A | G | G | G | G | G | G | cds_wt_3016 |
| 3418558 | C | | | T | T | T | T | — |
| 3418906 | G | | A | A | A | A | A | — |
| 3420004 | C | | T | T | T | | T | cds_wt_3019 |
| 3420345 | C | | | | | T | T | cds_wt_3019 |
| 3429994 | C | | | | | T | T | cds_wt_3030 |
| 3430020 | G | A | A | A | A | A | A | cds_wt_3030 |
| 3431269 | C | | T | T | T | T | T | cds_wt_3032 |
| 3432683 | G | | | | A | A | A | — |
| 3433788 | G | | | | A | A | A | — |
| 3434662 | C | | T | T | T | T | T | cds_wt_3034 |
| 3435439 | G | | | | A | A | A | cds_wt_3035 |
| 3435661 | G | | | | A | A | A | cds_wt_3035 |
| 3440357 | G | | | | A | A | A | cds_wt_3039 |
| 3441404 | C | | | | | T | T | — |
| 3453288 | C | | | | | T | T | cds_wt_3048 |
| 3454769 | G | | | | A | A | A | cds_wt_3048 |
| 3456480 | C | | T | T | T | T | T | — |
| 3457161 | C | | | | T | T | T | cds_wt_3050 |
| 3461043 | C | T | T | T | T | T | T | cds_wt_3053 |
| 3461116 | G | | A | A | A | A | A | cds_wt_3053 |
| 3464902 | C | T | T | T | T | T | T | cds_wt_3057 |
| 3469479 | C | | T | T | T | T | T | — |
| 3473066 | G | A | | A | A | | A | cds_wt_3065 |
| 3474749 | C | | T | T | T | T | T | — |
| 3484337 | G | | A | A | A | A | A | cds_wt_3076 |
| 3484696 | C | | T | T | T | T | T | cds_wt_3077 |
| 3490633 | G | A | A | A | A | A | A | cds_wt_3080 |
| 3511395 | C | | T | T | T | T | T | — |
| 3517523 | G | A | A | A | A | A | A | — |
| 3518338 | C | | T | T | T | T | T | cds_wt_3100 |
| 3519210 | C | T | T | T | T | T | T | cds_wt_3102 |
| 3519280 | C | T | T | T | T | T | T | cds_wt_3102 |
| 3526212 | G | A | A | A | A | A | A | cds_wt_3108 |
| 3526229 | G | A | A | | | | A | cds_wt_3108 |
| 3532172 | C | | | | | T | T | cds_wt_3117 |
| 3532281 | C | | | T | T | T | T | cds_wt_3117 |
| 3539856 | C | | T | T | T | T | T | cds_wt_3124 |
| 3540438 | C | | | | T | T | T | cds_wt_3124 |
| 3540952 | C | | | T | T | T | T | cds_wt_3125 |
| 3553678 | G | | | | | A | A | cds_wt_3135 |
| 3558780 | G | | A | A | A | A | A | cds_wt_3138 |
| 3559503 | G | A | A | A | A | A | A | cds_wt_3139 |
| 3560298 | T | | C | C | C | C | C | cds_wt_3140 |
| 3572036 | C | | T | T | T | T | T | cds_wt_3152 |
| 3587529 | C | | T | T | T | T | T | — |
| 3590513 | C | | T | T | T | T | T | cds_wt_3168 |
| 3590937 | C | | T | T | T | T | T | cds_wt_3168 |
| 3596971 | C | | | | | | T | cds_wt_3175 |
| 3601304 | C | | T | T | T | T | T | — |
| 3610733 | G | | A | A | A | | A | — |
| 3613460 | C | | | | | | T | cds_wt_3186 |
| 3617806 | G | | A | A | A | A | A | cds_wt_3189 |
| 3618063 | C | T | T | T | T | T | T | cds_wt_3189 |
| 3618082 | G | | | | | | A | cds_wt_3189 |
| 3621113 | G | | A | A | A | A | A | cds_wt_3191 |
| 3625554 | C | | T | T | T | T | T | cds_wt_3196 |
| 3626449 | C | | | T | T | T | T | cds_wt_3198 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 3626548 | C | | | | T | T | T | cds_wt_3198 |
| 3627377 | C | T | T | T | T | T | T | cds_wt_3199 |
| 3627686 | C | | | | T | T | T | cds_wt_3199 |
| 3628977 | C | | T | T | T | T | T | cds_wt_3199 |
| 3632788 | C | | | | | T | T | cds_wt_3200 |
| 3647003 | C | | | T | T | T | T | cds_wt_3215 |
| 3650159 | G | | | | | | A | cds_wt_3219 |
| 3658514 | C | | | | | T | T | cds_wt_3227 |
| 3659174 | C | T | T | T | T | T | T | cds_wt_3228 |
| 3672218 | G | A | A | A | A | A | A | cds_wt_3242 |
| 3695232 | G | A | A | A | A | A | A | cds_wt_3263 |
| 3702963 | C | | T | T | T | T | T | cds_wt_3268 |
| 3704185 | C | | T | T | T | T | T | cds_wt_3269 |
| 3704278 | G | | | | | | G/C | cds_wt_3269 |
| 3704281 | T | | | | | | T/G | cds_wt_3269 |
| 3704282 | C | | | | | | C/T | cds_wt_3269 |
| 3704293 | T | | | | | | T/G | cds_wt_3269 |
| 3704327 | G | | | | | | A/G | cds_wt_3269 |
| 3704335 | C | | | | | | T/C | cds_wt_3269 |
| 3704338 | C | | | | | | G/C | cds_wt_3269 |
| 3704340 | A | | | | | | C/A | cds_wt_3269 |
| 3704371 | G | | | | | | C/G | cds_wt_3269 |
| 3704386 | T | | | | | | C/T | cds_wt_3269 |
| 3704389 | C | | | | | | G/C | cds_wt_3269 |
| 3704395 | G | | | | | | C/G | cds_wt_3269 |
| 3704404 | G | | | | | | C/G | cds_wt_3269 |
| 3704415 | C | | | | | | T/C | cds_wt_3269 |
| 3704427 | G | G/A | G/A | G/A | G/A | G/A | A/G | cds_wt_3269 |
| 3704428 | C | C/T | T/C | C/T | C/T | C/T | T/C | cds_wt_3269 |
| 3704464 | C | C/T | C/T | C/T | C/T | C/T | T/C | cds_wt_3269 |
| 3704484 | A | | | | | | C/A | cds_wt_3269 |
| 3704485 | C | | | | | | G/C | cds_wt_3269 |
| 3704491 | G | | | | | | C/G | cds_wt_3269 |
| 3704512 | G | | | | | | C/G | cds_wt_3269 |
| 3704519 | A | | | | | | G/A | cds_wt_3269 |
| 3704531 | A | | | | | | G/A | cds_wt_3269 |
| 3704534 | G | | | | | | C/G | cds_wt_3269 |
| 3704536 | C | | | | | | G/C | cds_wt_3269 |
| 3704543 | C | | | | | | G/C | cds_wt_3269 |
| 3704544 | T | | | | | | C/T | cds_wt_3269 |
| 3704554 | T | | | | | | T/G | cds_wt_3269 |
| 3704563 | C | | | | | | G/C | cds_wt_3269 |
| 3704573 | A | | | | | | G/A | cds_wt_3269 |
| 3704574 | A | | | | | | G/A | cds_wt_3269 |
| 3704577 | G | | | | | | C/G | cds_wt_3269 |
| 3704584 | C | | | | | | G/C | cds_wt_3269 |
| 3704587 | G | | | | | | A/G | cds_wt_3269 |
| 3704590 | G | | | | | | C/G | cds_wt_3269 |
| 3704605 | T | | | | | | C/T | cds_wt_3269 |
| 3704608 | C | | | | | | G/C | cds_wt_3269 |
| 3704617 | T | | | | | | G/T | cds_wt_3269 |
| 3704619 | A | | | | | | C/A | cds_wt_3269 |
| 3704620 | C | | | | | | A/C | cds_wt_3269 |
| 3704629 | C | | | | | | G/C | cds_wt_3269 |
| 3704638 | C | | | | | | G/C | cds_wt_3269 |
| 3704641 | G | | | | | | C/G | cds_wt_3269 |
| 3704647 | C | | | | | | G/C | cds_wt_3269 |
| 3704650 | G | | | | | | C/G | cds_wt_3269 |
| 3704660 | C | | | | | | A/C | cds_wt_3269 |
| 3704662 | G | | | | | | A/G | cds_wt_3269 |
| 3704668 | T | | | | | | C/T | cds_wt_3269 |
| 3704669 | G | | | | | | A/G | cds_wt_3269 |
| 3704670 | T | | | | | | C/T | cds_wt_3269 |
| 3704680 | C | | | | | | G/C | cds_wt_3269 |
| 3704684 | C | | | | | | G/C | cds_wt_3269 |
| 3704686 | G | | | | | | C/G | cds_wt_3269 |
| 3704746 | G | G/C | G/C | G/C | G/C | G/C | C/G | cds_wt_3269 |
| 3704755 | C | C/G | C/G | C/G | C/G | C/G | C/G | cds_wt_3269 |
| 3704767 | A | A/G | A/G | A/G | A/G | A/G | A/G | cds_wt_3269 |
| 3704782 | T | | | | | | T/C | cds_wt_3269 |
| 3704789 | A | | | | | | A/G | cds_wt_3269 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 3704791 | C | | | | | | C/G | cds_wt_3269 |
| 3704806 | C | | | | | | C/T | cds_wt_3269 |
| 3704815 | T | | | | | | T/C | cds_wt_3269 |
| 3704822 | C | | | | | | C/G | cds_wt_3269 |
| 3704844 | C | | | | | | C/A | cds_wt_3269 |
| 3704851 | A | | | | | | A/G | cds_wt_3269 |
| 3704852 | C | | | | | | C/A | cds_wt_3269 |
| 3704866 | T | | | | | | T/C | cds_wt_3269 |
| 3704869 | C | | | | | | C/G | cds_wt_3269 |
| 3704875 | C | | | | | | C/G | cds_wt_3269 |
| 3704906 | G | | | | | A | A | cds_wt_3269 |
| 3706589 | C | | | | | | C/G | cds_wt_3270 |
| 3706625 | G | | | | | | G/C | cds_wt_3270 |
| 3706641 | G | | | | | | G/T | cds_wt_3270 |
| 3706652 | G | | | | | | G/A | cds_wt_3270 |
| 3706655 | C | | | | | | C/G | cds_wt_3270 |
| 3706679 | T | | | | | | T/C | cds_wt_3270 |
| 3706715 | C | | | | | | C/G | cds_wt_3270 |
| 3706735 | C | | | | | | C/G | cds_wt_3270 |
| 3706737 | A | | | | | | A/G | cds_wt_3270 |
| 3706739 | G | | | | | | G/C | cds_wt_3270 |
| 3706784 | C | | | | | | C/T | cds_wt_3270 |
| 3706790 | T | | | | | | T/C | cds_wt_3270 |
| 3706794 | A | | | | | | A/G | cds_wt_3270 |
| 3706805 | G | | | | | | G/C | cds_wt_3270 |
| 3706822 | A | | | | | | A/G | cds_wt_3270 |
| 3706862 | C | C/G | C/G | C/G | C/G | C/G | C/G | cds_wt_3270 |
| 3706926 | G | | | | | | G/T | cds_wt_3270 |
| 3706932 | A | | | | | | A/C | cds_wt_3270 |
| 3706940 | G | | | | | | G/A | cds_wt_3270 |
| 3706945 | G | | | | | | G/C | cds_wt_3270 |
| 3706950 | T | | | | | | T/A | cds_wt_3270 |
| 3706951 | C | | | | | | C/G | cds_wt_3270 |
| 3706958 | T | | | | | | T/C | cds_wt_3270 |
| 3706960 | A | | | | | | A/G | cds_wt_3270 |
| 3706967 | C | | | | | | C/G | cds_wt_3270 |
| 3706983 | C | | | | | | C/G | cds_wt_3270 |
| 3706985 | G | | | | | | G/C | cds_wt_3270 |
| 3706994 | G | | | | | | G/C | cds_wt_3270 |
| 3706996 | A | | | | | | A/C | cds_wt_3270 |
| 3707006 | G | | | | | | G/C | cds_wt_3270 |
| 3707012 | C | | | | | | C/A | cds_wt_3270 |
| 3707013 | A | | | | | | A/G | cds_wt_3270 |
| 3707036 | C | | | | | | C/G | cds_wt_3270 |
| 3711369 | G | | | | | A | A | cds_wt_3273 |
| 3713575 | C | | | | | | T | cds_wt_3274 |
| 3724878 | G | | A | A | A | A | A | cds_wt_3284 |
| 3724955 | G | | A | A | A | A | A | cds_wt_3285 |
| 3727102 | G | | | | | | A | cds_wt_3287 |
| 3727130 | G | | | | | | A | cds_wt_3287 |
| 3727909 | C | | T | T | T | T | T | cds_wt_3288 |
| 3732046 | C | | | | | T | T | cds_wt_3292 |
| 3733052 | G | A | A | A | A | A | A | cds_wt_3293 |
| 3740023 | G | | | | | A | A | cds_wt_3297 |
| 3741710 | G | | | | | A | A | cds_wt_3299 |
| 3744813 | G | | | | | A | A | cds_wt_3301 |
| 3750360 | G | | | | | A | A | cds_wt_3306 |
| 3756113 | C | T | T | T | T | T | T | cds_wt_3312 |
| 3762328 | G | | | | | | A | cds_wt_3318 |
| 3763755 | G | | | | | A | A | cds_wt_3319 |
| 3764788 | G | | A | A | A | A | A | cds_wt_3320 |
| 3771690 | C | T | T | T | T | T | T | cds_wt_3327 |
| 3775098 | G | | | | | | A | cds_wt_3331 |
| 3775718 | G | | | | | A | A | cds_wt_3332 |
| 3776484 | G | | | | | A | A | cds_wt_3333 |
| 3783703 | T | | C | C | C | C | C | cds_wt_3342 |
| 3786947 | G | | | | | A | A | cds_wt_3346 |
| 3788243 | C | | | | | T | T | — |
| 3798429 | G | | | | | A | A | cds_wt_3363 |
| 3799202 | G | | A | A | A | A | A | cds_wt_3364 |
| 3799222 | G | | A | A | A | A | A | cds_wt_3364 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 3802171 | C | T | T | T | T | T | T | cds_wt_3368 |
| 3806580 | C | | | | | T | T | cds_wt_3371 |
| 3825163 | C | | | | | T | T | cds_wt_3394 |
| 3828141 | G | | | | | A | A | — |
| 3831054 | G | | | | | A | A | cds_wt_3401 |
| 3831114 | G | | A | A | A | A | A | cds_wt_3401 |
| 3831589 | C | | | | | T | T | — |
| 3831701 | G | | | | | A | A | — |
| 3837175 | G | | | | | A | A | cds_wt_3406 |
| 3841387 | G | | | | | A | A | cds_wt_3410 |
| 3843222 | C | T | T | T | T | T | T | cds_wt_3413 |
| 3843509 | G | | | | | A | A | cds_wt_3414 |
| 3843815 | G | A | A | A | A | A | A | cds_wt_3414 |
| 3844238 | G | | | | | A | A | cds_wt_3414 |
| 3846121 | G | | | | | | A | cds_wt_3417 |
| 3846452 | G | | | | | A | A | cds_wt_3417 |
| 3852914 | T | | C | C | C | C | C | cds_wt_3423 |
| 3873931 | G | | | | | | A | cds_wt_3442 |
| 3879758 | G | | | | | A | A | cds_wt_3449 |
| 3883035 | C | T | T | T | T | T | T | cds_wt_3453 |
| 3905636 | C | | | | | T | T | cds_wt_3478 |
| 3919216 | C | | T | T | T | T | T | cds_wt_3488 |
| 3920191 | G | | | | | A | A | cds_wt_3489 |
| 3928659 | C | | T | T | T | T | T | cds_wt_3496 |
| 3935704 | C | | | | | | C/T | cds_wt_3503 |
| 3941486 | G | | | | A | A | A | cds_wt_3508 |
| 3964297 | G | | | | | A | A | cds_wt_3529 |
| 3965972 | G | | | A | A | A | A | cds_wt_3530 |
| 3968608 | C | | T | T | T | T | T | cds_wt_3533 |
| 3983198 | C | | T | T | T | T | T | cds_wt_3545 |
| 3993744 | G | | | | | | G/A | cds_wt_3554 |
| 4002370 | G | | A | A | A | A | A | cds_wt_3560 |
| 4004770 | C | | T | T | T | T | T | cds_wt_3562 |
| 4006580 | C | T | T | T | T | T | T | cds_wt_3562 |
| 4006932 | G | | A | A | A | A | A | cds_wt_3562 |
| 4013932 | G | A | A | A | A | A | A | cds_wt_3571 |
| 4014337 | T | | | | C | C | C | cds_wt_3572 |
| 4017638 | C | | | | T | T | T | cds_wt_3574 |
| 4019106 | G | | A | A | A | A | A | cds_wt_3576 |
| 4020770 | C | | T | T | T | T | T | cds_wt_3577 |
| 4025302 | C | T | T | T | T | T | T | cds_wt_3582 |
| 4027304 | G | | | | A | A | A | cds_wt_3584 |
| 4034139 | G | | | | | | G/T | cds_wt_3588 |
| 4043320 | A | | | | | G | G | cds_wt_3599 |
| 4063459 | G | | A | A | A | A | A | cds_wt_3621 |
| 4072648 | C | | T | T | T | T | T | cds_wt_3630 |
| 4073198 | C | | | | | | T | cds_wt_3630 |
| 4073446 | G | | | | | | A | cds_wt_3630 |
| 4074524 | C | | T | T | T | T | T | cds_wt_3631 |
| 4081747 | C | | | | T | T | T | cds_wt_3639 |
| 4086210 | A | G | G | G | G | G | G | cds_wt_3643 |
| 4089001 | C | | | T | T | | T | cds_wt_3647 |
| 4102977 | C | | | | | T | T | cds_wt_3657 |
| 4104004 | C | | | | | T | T | cds_wt_3658 |
| 4114649 | G | | A | A | A | A | A | cds_wt_3670 |
| 4117981 | G | | A | A | A | A | A | cds_wt_3673 |
| 4118234 | C | | T | T | T | T | T | — |
| 4121337 | G | | A | A | A | A | A | — |
| 4124406 | G | | A | A | A | A | A | cds_wt_3680 |
| 4130087 | C | | T | T | T | T | T | cds_wt_3683 |
| 4148633 | C | | | | | T | T | cds_wt_3698 |
| 4150599 | C | | | | | T | T | cds_wt_3700 |
| 4152842 | C | | T | T | T | T | T | cds_wt_3703 |
| 4156366 | G | A | A | A | A | | A | cds_wt_3707 |
| 4156524 | G | | | | | A | A | cds_wt_3707 |
| 4157742 | G | A | A | A | A | A | A | cds_wt_3708 |
| 4157795 | G | A | A | A | A | A | A | cds_wt_3708 |
| 4158022 | G | A | A | A | A | A | A | cds_wt_3708 |
| 4160265 | G | A | | A | A | | A | — |
| 4170648 | C | | T | T | T | T | T | cds_wt_3719 |
| 4186914 | C | | | | T | | T | cds_wt_3734 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 4187188 | G | | | | A | | A | cds_wt_3735 |
| 4192330 | C | | T | T | T | T | T | cds_wt_3740 |
| 4192395 | C | T | T | T | T | T | T | cds_wt_3740 |
| 4194086 | C | T | | T | T | | T | cds_wt_3741 |
| 4196729 | C | T | T | T | T | T | T | cds_wt_3743 |
| 4205330 | C | | | | | | T | cds_wt_3752 |
| 4218066 | G | A | A | A | A | A | A | cds_wt_3764 |
| 4220842 | G | | A | A | A | A | A | cds_wt_3768 |
| 4231722 | C | | T | T | T | T | T | cds_wt_3782 |
| 4251577 | C | | T | T | | | | — |
| 4253562 | G | | | | A | A | A | — |
| 4255089 | G | | A | A | A | A | A | cds_wt_3798 |
| 4268915 | C | T | T | T | T | T | T | cds_wt_3809 |
| 4284264 | C | T | T | T | T | T | T | cds_wt_3820 |
| 4285070 | G | | | | | | A | cds_wt_3821 |
| 4286615 | G | | | | | | A | cds_wt_3823 |
| 4299670 | C | | T | T | T | T | T | — |
| 4302785 | G | | A | A | A | A | A | cds_wt_3840 |
| 4302812 | C | | | | | | T | cds_wt_3840 |
| 4312528 | G | | A | A | A | A | A | cds_wt_3851 |
| 4312875 | C | | | | | T | T | cds_wt_3851 |
| 4314885 | G | | A | A | A | A | A | cds_wt_3852 |
| 4314896 | C | T | T | T | T | T | T | cds_wt_3852 |
| 4314899 | G | | A | A | A | A | A | cds_wt_3852 |
| 4316350 | C | T | T | T | T | T | T | cds_wt_3853 |
| 4318874 | C | | T | T | T | T | T | — |
| 4319625 | C | | | | T | T | T | — |
| 4324089 | G | | | A | A | A | A | cds_wt_3859 |
| 4325174 | G | | A | A | A | A | A | cds_wt_3860 |
| 4325955 | G | | A | A | A | A | A | cds_wt_3860 |
| 4327176 | C | | T | T | T | T | T | cds_wt_3861 |
| 4328372 | C | | T | T | T | T | T | cds_wt_3861 |
| 4329685 | C | | T | T | T | T | T | cds_wt_3862 |
| 4329867 | C | | T | T | T | T | T | cds_wt_3862 |
| 4331851 | C | | T | T | T | T | T | cds_wt_3862 |
| 4331916 | C | | T | T | T | T | T | cds_wt_3862 |
| 4334253 | C | | | | | | T | — |
| 4335755 | C | | | | T | T | T | — |
| 4340706 | C | | | | | T | T | — |
| 4343282 | T | | | | | | C | cds_wt_3868 |
| 4347901 | C | | | | T | T | T | cds_wt_3875 |
| 4352755 | G | A | A | A | A | A | A | cds_wt_3879 |
| 4360959 | G | A | A | A | A | A | A | cds_wt_3884 |
| 4361293 | C | | | | T | T | T | cds_wt_3884 |
| 4362371 | C | | T | T | T | T | T | cds_wt_3885 |
| 4365880 | G | | | | | A | A | cds_wt_3888 |
| 4376161 | C | | | T | T | T | T | cds_wt_3893 |
| 4376238 | C | | T | T | T | T | T | cds_wt_3893 |
| 4378853 | G | | A | A | A | A | A | — |
| 4395837 | G | | | | | A | A | cds_wt_3904 |
| 4396016 | C | | T | T | T | T | T | cds_wt_3904 |
| 4402736 | C | | T | T | T | T | T | cds_wt_3911 |
| 4406151 | G | | | | | A | A | cds_wt_3914 |
| 4414580 | G | A | A | A | A | A | A | — |
| 4414632 | C | | T | T | T | T | T | — |
| 4420655 | C | | | | | T | T | cds_wt_3928 |
| 4433146 | G | | | | | | A | cds_wt_3940 |
| 4438071 | G | | A | A | A | A | A | — |
| 4440571 | T | | C | C | C | C | C | cds_wt_3948 |
| 4440772 | G | | | | | A | A | cds_wt_3949 |
| 4443633 | G | | | | | A | A | cds_wt_3952 |
| 4444731 | C | | | | | | T | cds_wt_3953 |
| 4446487 | T | | C | C | C | C | C | cds_wt_3954 |
| 4463567 | C | T | | | T | | T | cds_wt_3967 |
| 4463766 | G | | A | | | | A | cds_wt_3967 |
| 4467838 | G | | | | | | A | cds_wt_3969 |
| 4474494 | G | | A | A | A | A | A | cds_wt_3976 |
| 4481185 | G | | | A | A | A | A | cds_wt_3981 |
| 4486135 | C | | T | T | T | T | T | cds_wt_3985 |
| 4487769 | G | | | | | | A | cds_wt_3986 |
| 4490385 | G | | A | A | A | A | A | cds_wt_3989 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 4496083 | G | | A | A | A | A | A | cds_wt_3998 |
| 4499876 | C | | T | T | T | T | T | cds_wt_4002 |
| 4503563 | C | T | T | T | T | T | T | cds_wt_4006 |
| 4504062 | C | T | T | T | T | T | T | cds_wt_4006 |
| 4517204 | G | A | A | A | A | A | A | cds_wt_4018 |
| 4524639 | G | | | | A | | A | cds_wt_4025 |
| 4524706 | G | | | | | | A | cds_wt_4025 |
| 4529241 | G | | A | A | A | A | A | cds_wt_4028 |
| 4529778 | G | | A | A | A | A | A | cds_wt_4029 |
| 4531772 | G | A | A | A | A | A | A | cds_wt_4032 |
| 4532547 | G | A | A | A | A | A | A | cds_wt_4032 |
| 4532943 | G | A | A | A | A | A | A | cds_wt_4033 |
| 4533824 | G | A | A | A | A | A | A | cds_wt_4034 |
| 4535251 | G | | A | A | A | A | A | cds_wt_4035 |
| 4537480 | G | | A | A | A | A | A | cds_wt_4036 |
| 4537859 | G | A | A | A | A | A | A | — |
| 4543587 | G | A | A | A | A | A | A | cds_wt_4041 |
| 4547764 | C | | | | | T | T | cds_wt_4046 |
| 4558815 | C | | T | T | T | T | T | — |
| 4558914 | C | | T | T | T | T | T | cds_wt_4060 |
| 4564648 | G | A | A | A | A | A | A | cds_wt_4064 |
| 4564991 | G | A | A | A | A | A | A | cds_wt_4064 |
| 4573497 | C | | T | T | T | T | T | cds_wt_4073 |
| 4573536 | C | | T | T | T | T | T | cds_wt_4073 |
| 4575408 | C | | | | | T | T | cds_wt_4075 |
| 4577334 | C | T | T | T | T | T | T | cds_wt_4076 |
| 4580403 | G | | | | | | A | cds_wt_4079 |
| 4582642 | T | | | | C | C | C | — |
| 4588387 | C | A | A | A | A | A | A | cds_wt_4086 |
| 4588663 | G | | A | A | A | A | A | cds_wt_4087 |
| 4597434 | C | | | | | T | T | — |
| 4598262 | C | | T | T | T | T | T | cds_wt_4091 |
| 4601247 | G | | | | | | G/C | cds_wt_4093 |
| 4601248 | T | | | | | | T/C | cds_wt_4093 |
| 4603166 | C | | | | | T | T | cds_wt_4094 |
| 4611131 | C | | T | T | T | T | T | cds_wt_4099 |
| 4614475 | C | | T | T | T | T | T | cds_wt_4103 |
| 4616665 | G | | A | A | A | A | A | cds_wt_4104 |
| 4617801 | G | | | | | | A | cds_wt_4106 |
| 4619989 | C | | T | T | | | T | cds_wt_4108 |
| 4621439 | G | A | A | A | A | A | A | cds_wt_4109 |
| 4626601 | G | A | | A | A | A | A | cds_wt_4114 |
| 4630752 | C | | T | T | T | T | T | cds_wt_4116 |
| 4649811 | A | | | | | | A/G | cds_wt_4135 |
| 4650590 | C | | | | T | T | T | cds_wt_4136 |
| 4669551 | C | | T | T | T | T | T | cds_wt_4157 |
| 4670815 | G | | | | | | A | cds_wt_4158 |
| 4674426 | G | | | A | A | A | A | cds_wt_4162 |
| 4677968 | C | | T | T | T | T | T | cds_wt_4168 |
| 4688341 | C | | | | | | T | cds_wt_4174 |
| 4697092 | C | | T | T | T | T | T | cds_wt_4179 |
| 4700003 | G | A | A | A | A | A | A | cds_wt_4181 |
| 4702254 | C | T | T | T | T | T | T | cds_wt_4183 |
| 4704691 | C | T | T | T | T | T | T | cds_wt_4185 |
| 4704704 | C | T | T | T | T | T | T | cds_wt_4185 |
| 4713174 | C | | T | T | T | T | T | — |
| 4727776 | G | A | A | A | A | A | A | cds_wt_4209 |
| 4736024 | C | | | | | | T | cds_wt_4219 |
| 4766839 | C | T | T | T | T | T | T | cds_wt_4240 |
| 4769655 | C | T | | T | T | T | T | cds_wt_4243 |
| 4776927 | G | | A | A | A | A | A | cds_wt_4247 |
| 4788381 | C | | | | | T | T | cds_wt_4255 |
| 4794373 | C | T | T | T | T | T | T | cds_wt_4264 |
| 4799012 | G | A | A | A | A | A | A | cds_wt_4268 |
| 4812357 | C | | | | | | T | cds_wt_4277 |
| 4813704 | G | | | | | | G/T | — |
| 4813710 | G | | | | | | G/T | — |
| 4813711 | A | | | | | | A/C | — |
| 4814060 | C | | | | T/C | | C/T | — |
| 4814078 | C | | | | | | C/T | — |
| 4814081 | C | | | | | | C/T | — |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 4814082 | G | | | | | | G/C | — |
| 4814087 | T | | | | | | T/C | — |
| 4818340 | G | | | | A | | A | — |
| 4820651 | C | | | | T | | T | cds_wt_4283 |
| 4821863 | G | A | A | A | A | A | A | — |
| 4852073 | T | | | | | | T/C | — |
| 4852080 | T | | | | | | C/T | cds_wt_4318 |
| 4852093 | T | | | | | | C/T | cds_wt_4318 |
| 4852131 | G | | | | | | A/G | cds_wt_4318 |
| 4852238 | T | | | | C/T | C/T | C/T | cds_wt_4318 |
| 4852271 | T | | | | | | T/C | cds_wt_4318 |
| 4852348 | G | | G/A | G/A | G/A | G/A | G/A | cds_wt_4318 |
| 4852373 | T | | | | | | T/C | cds_wt_4318 |
| 4858842 | C | T | T | T | T | T | T | cds_wt_4320 |
| 4859921 | G | A | A | A | A | A | A | cds_wt_4321 |
| 4860949 | G | | A | A | A | A | A | cds_wt_4321 |
| 4872907 | G | | | | A | A | A | cds_wt_4325 |
| 4879205 | C | | | | T | | T | cds_wt_4332 |
| 4886810 | C | | | | T | | T | cds_wt_4337 |
| 4889101 | G | A | A | A | A | A | A | cds_wt_4340 |
| 4891956 | C | | | | T | | T | cds_wt_4341 |
| 4896797 | C | | T | T | T | T | T | cds_wt_4345 |
| 4903124 | G | | | | | | A | cds_wt_4350 |
| 4904325 | A | | | | | | A/G | — |
| 4904344 | C | | | | | | C/G | — |
| 4904345 | C | | | | | | C/T | — |
| 4904355 | A | | | | | | G | — |
| 4904359 | G | | | | | | G/C | — |
| 4904360 | T | | | | | | T/C | — |
| 4908341 | C | | T | T | T | T | T | — |
| 4908687 | C | | | | | | T | — |
| 4911304 | C | | | | | | T | cds_wt_4356 |
| 4916472 | C | | T | T | T | T | T | cds_wt_4359 |
| 4920831 | C | | | | | | T | cds_wt_4362 |
| 4924034 | C | | T | T | T | T | T | cds_wt_4363 |
| 4924484 | C | | T | T | T | T | T | cds_wt_4363 |
| 4927068 | C | | T | T | T | T | T | cds_wt_4367 |
| 4927798 | C | | T | T | T | T | T | cds_wt_4367 |
| 4929941 | C | | T | T | T | T | T | cds_wt_4370 |
| 4930693 | C | | | T | T | T | T | cds_wt_4370 |
| 4932671 | C | | | | | | T | cds_wt_4373 |
| 4933447 | T | | | | | | T/C | cds_wt_4374 |
| 4948234 | G | | | | | A | A | cds_wt_4390 |
| 4950870 | C | T | T | T | T | T | T | cds_wt_4393 |
| 4951932 | C | T | T | T | T | T | T | cds_wt_4394 |
| 4953821 | C | T | | | T | | T | — |
| 4978515 | G | A | | | | | A | cds_wt_4414 |
| 4981742 | C | | | | | | T | cds_wt_4416 |
| 4984320 | A | | G | G | G | G | G | cds_wt_4417 |
| 4987021 | G | A | A | A | A | A | A | cds_wt_4421 |
| 4987606 | G | | A | A | A | A | A | cds_wt_4421 |
| 4991441 | G | | A | A | A | A | A | cds_wt_4424 |
| 4992870 | G | A | A | A | A | A | A | cds_wt_4425 |
| 5014441 | C | T | T | T | T | T | T | cds_wt_4442 |
| 5016187 | C | T | T | T | T | T | T | cds_wt_4443 |
| 5016773 | C | T | T | T | T | T | T | cds_wt_4443 |
| 5025119 | G | | | | | | A | cds_wt_4454 |
| 5030757 | C | | | | | | T | cds_wt_4459 |
| 5053257 | C | | T | T | T | T | T | cds_wt_4482 |
| 5056010 | C | | T | T | T | T | T | — |
| 5056241 | C | | T | T | T | T | T | cds_wt_4487 |
| 5058845 | C | | | | | T | T | — |
| 5058850 | C | | | | | T | T | — |
| 5060436 | C | | T | T | T | T | T | cds_wt_4489 |
| 5061245 | C | | T | T | T | T | T | cds_wt_4489 |
| 5062621 | C | | T | T | T | T | T | cds_wt_4490 |
| 5063656 | C | | T | T | T | T | T | cds_wt_4492 |
| 5063753 | A | | | | | | A/G | cds_wt_4492 |
| 5063759 | T | | | | | | T/G | cds_wt_4492 |
| 5063766 | C | | | | | | C/T | cds_wt_4492 |
| 5063772 | A | | | | | | A/G | cds_wt_4492 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 5063775 | T | | | | | | T/C | cds_wt_4492 |
| 5063777 | A | | | | | | A/G | cds_wt_4492 |
| 5063883 | T | | | | | | T/C | cds_wt_4492 |
| 5063900 | G | G/A | G/A | G/A | G/A | G/A | G/A | cds_wt_4492 |
| 5063967 | T | | | | | | C/T | cds_wt_4492 |
| 5063994 | C | | | | | | C/G | cds_wt_4492 |
| 5063997 | T | | | | | | C/T | cds_wt_4492 |
| 5064000 | G | | | | | | C/G | cds_wt_4492 |
| 5064054 | C | C/G | C/G | | C/G | | C/G | cds_wt_4492 |
| 5064140 | T | T/A | T/A | T/A | | T/A | A/T | cds_wt_4492 |
| 5064188 | G | G/C | G/C | G/C | G/C | G/C | G/C | — |
| 5064199 | G | G/A | G/A | G/A | G/A | G/A | A/G | — |
| 5064223 | T | T/C | T/C | T/C | T/C | T/C | C/T | — |
| 5064318 | G | G/A | | G/A | G/A | G/A | G/A | — |
| 5064363 | G | | | | | | G/A | — |
| 5064364 | C | | | | | | C/G | — |
| 5064368 | T | T/C | T/C | T/C | T/C | C/T | C/T | — |
| 5066806 | C | | T | T | T | T | T | cds_wt_4496 |
| 5079654 | C | | | | | | T | cds_wt_4505 |
| 5080712 | C | | T | T | T | T | T | cds_wt_4505 |
| 5080760 | G | | A | A | A | A | A | — |
| 5083716 | C | | T | T | T | T | T | cds_wt_4508 |
| 5085149 | C | | T | T | T | T | T | cds_wt_4509 |
| 5087053 | C | | T | T | T | T | T | cds_wt_4509 |
| 5089288 | G | | A | A | A | A | A | cds_wt_4511 |
| 5095356 | C | | T | T | T | T | T | cds_wt_4517 |
| 5096131 | C | | T | T | T | T | T | cds_wt_4517 |
| 5099106 | C | | | | | T | T | cds_wt_4520 |
| 5099331 | C | | | | | T | T | cds_wt_4521 |
| 5099501 | C | | | | | | T | cds_wt_4521 |
| 5104316 | C | | T | T | T | T | T | cds_wt_4525 |
| 5104896 | C | | T | T | T | T | T | cds_wt_4525 |
| 5105840 | C | | T | T | T | T | T | cds_wt_4526 |
| 5107273 | C | | T | T | T | T | T | cds_wt_4528 |
| 5107438 | G | | | | | | A | cds_wt_4528 |
| 5110964 | G | | | | | | A | cds_wt_4534 |
| 5111341 | G | | | A | | | A | cds_wt_4534 |
| 5111525 | G | A | | A | | | A | cds_wt_4534 |
| 5113971 | C | | T | T | T | T | T | cds_wt_4535 |
| 5114926 | C | | | | | | T/C | — |
| 5114933 | C | | | | | | T/C | — |
| 5116995 | G | | | | A | A | A | cds_wt_4538 |
| 5117622 | G | | | | A | A | A | cds_wt_4538 |
| 5126463 | G | | | | A | A | A | — |
| 5128522 | G | | | | A | A | A | cds_wt_4545 |
| 5131328 | G | | A | A | A | A | A | cds_wt_4547 |
| 5132598 | C | | T | T | T | T | T | cds_wt_4548 |
| 5133033 | C | | T | T | T | T | T | cds_wt_4548 |
| 5134996 | G | | A | A | A | A | A | cds_wt_4551 |
| 5136119 | C | | T | T | T | T | T | cds_wt_4552 |
| 5139533 | C | T | T | T | T | T | T | cds_wt_4555 |
| 5141709 | G | | A | A | A | A | A | cds_wt_4556 |
| 5147647 | C | | T | T | T | T | T | cds_wt_4560 |
| 5158997 | C | | T | T | T | T | T | cds_wt_4571 |
| 5171223 | G | A | A | A | A | A | A | — |
| 5189948 | C | | T | T | T | T | T | cds_wt_4598 |
| 5196838 | C | | T | T | T | T | T | cds_wt_4603 |
| 5203530 | G | | | | | | A | cds_wt_4610 |
| 5204859 | C | | T | T | T | T | T | cds_wt_4612 |
| 5213315 | G | | | | | | A | cds_wt_4621 |
| 5216015 | G | | A | A | A | A | A | cds_wt_4624 |
| 5221083 | C | | T | T | T | T | T | cds_wt_4628 |
| 5229965 | G | | A | A | A | A | A | cds_wt_4633 |
| 5233924 | G | | | | | | A | cds_wt_4635 |
| 5246591 | G | | | | A | A | A | cds_wt_4645 |
| 5247914 | C | T | T | T | T | T | T | cds_wt_4646 |
| 5253451 | C | T | | | | | T | cds_wt_4650 |
| 5255901 | C | | T | T | T | T | T | cds_wt_4652 |
| 5259871 | G | | A | A | A | A | A | cds_wt_4654 |
| 5270798 | G | A | A | A | A | A | A | cds_wt_4667 |
| 5277822 | G | A | | A | A | | A | cds_wt_4674 |

-continued

| Position in reference wild type strain SE50-100 | Base in Reference strain | SN223-29-47 | C445-P47 | SN12755-48 | SC3687-18-43 | SC7177-40-17 | SN19910-27-21 | Affected Gene ID |
|---|---|---|---|---|---|---|---|---|
| 5280936 | C | | T | T | T | T | T | cds_wt_4680 |
| 5283902 | G | | | | | A | A | cds_wt_4682 |
| 5292603 | C | T | T | T | T | T | T | cds_wt_4692 |
| 5309793 | G | | A | A | A | A | A | cds_wt_4713 |
| 5317263 | G | | | | A | A | A | cds_wt_4720 |
| 5323245 | G | | | | | A | A | cds_wt_4725 |
| 5323289 | C | | | | | T | T | cds_wt_4725 |
| 5323708 | G | | | | | A | A | cds_wt_4726 |
| 5326705 | G | | | | | A | A | cds_wt_4730 |
| 5339380 | G | A | | | | | A | cds_wt_4742 |
| 5349635 | C | T | T | T | T | | T | cds_wt_4752 |
| 5350111 | G | | A | A | A | A | A | cds_wt_4752 |
| 5356868 | C | | T | T | T | T | T | cds_wt_4756 |
| 5363828 | C | | | | | T | T | cds_wt_4763 |
| 5385564 | C | T | T | T | T | T | T | cds_wt_4780 |
| 5391456 | G | | A | A | A | A | A | cds_wt_4787 |
| 5404805 | G | | | | | A | A | cds_wt_4798 |
| 5415953 | G | A | A | A | A | A | A | cds_wt_4808 |
| 5416207 | C | T | T | T | T | T | T | cds_wt_4808 |
| 5419045 | C | | T | T | T | T | T | cds_wt_4811 |
| 5438747 | G | A | A | A | A | A | A | cds_wt_4833 |
| 5457995 | G | | A | A | A | A | A | cds_wt_4849 |
| 5465469 | C | | | | | T | T | cds_wt_4855 |
| 5481386 | G | | | | | A | A | cds_wt_4866 |
| 5485106 | C | | T | T | T | T | T | cds_wt_4869 |
| 5500846 | G | | A | A | A | A | A | cds_wt_4887 |
| 5514802 | C | | T | T | T | T | T | cds_wt_4901 |
| 5516464 | C | | | | | | T | cds_wt_4902 |
| 5530664 | C | | T | T | T | T | T | cds_wt_4914 |
| 5537010 | G | A | A | A | A | A | A | cds_wt_4920 |
| 5540526 | G | A | | | | | A | — |
| 5541233 | C | | T | T | T | T | T | cds_wt_4926 |
| 5543634 | C | | T | T | T | T | T | cds_wt_4929 |
| 5545010 | C | | | | | | T | cds_wt_4929 |
| 5545574 | G | | | | | A | A | cds_wt_4929 |
| 5548499 | C | | | T | T | T | T | cds_wt_4933 |
| 5557711 | G | A | | A | A | | A | cds_wt_4941 |
| 5574966 | C | T | T | T | T | T | T | cds_wt_4961 |
| 5576016 | C | | T | T | T | T | T | — |
| 5579654 | C | | | | T | T | T | cds_wt_4970 |
| 5582215 | C | | | | | | C/T | cds_wt_4972 |
| 5590781 | T | | | | | | T/A | — |
| 5590796 | C | | | | | | C/T | — |
| 5590809 | T | | | | | | T/C | — |
| 5590810 | G | | | | | | G/A | — |
| 5590823 | G | G/A | G/A | G/A | G/A | G/A | G/A | — |
| 5590828 | A | | | | | | A/G | — |
| 5590847 | G | G/T | G/T | G/T | G/T | G/T | G/T | — |
| 5590861 | G | G/C | G/C | G/C | G/C | G/C | G/C | — |
| 5590867 | A | A/C | A/C | A/C | A/C | A/C | A/C | — |
| 5590868 | A | | | | | | A/G | — |
| 5590886 | G | G/A | G/A | G/A | G/A | G/A | A/G | cds_wt_4977 |
| 5590889 | T | T/C | T/C | T/C | | T/C | C/T | cds_wt_4977 |
| 5590903 | A | | | | | | G/A | cds_wt_4977 |
| 5590909 | G | | | | | | T/G | cds_wt_4977 |
| 5590910 | C | | | | | | G/C | cds_wt_4977 |
| 5590912 | G | | | | | | T/G | cds_wt_4977 |
| 5590918 | G | | | | | | A/G | cds_wt_4977 |
| 5590923 | A | | | | | | G/A | cds_wt_4977 |
| 5590927 | T | | | | | | G/T | cds_wt_4977 |
| 5590933 | G | | | | | | A/G | cds_wt_4977 |
| 5590945 | C | | | | | | G/C | cds_wt_4977 |
| 5590960 | T | | | | | | C/T | cds_wt_4977 |
| 5590961 | C | | | | | | T/C | cds_wt_4977 |
| 5590972 | T | | | | | | C/T | cds_wt_4977 |
| 5590978 | T | | | | | | C/T | cds_wt_4977 |
| 5590981 | G | | | | | | C/G | cds_wt_4977 |
| 5590987 | T | | | | | | C/T | cds_wt_4977 |
| 5590993 | C | C/G | | | | | G/C | cds_wt_4977 |
| 5591002 | G | | | | | | G/A | cds_wt_4977 |
| 5591008 | T | C/T | T/C | T/C | C/T | T/C | C/T | cds_wt_4977 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 5591026 | C | | | | | | G/C | cds_wt_4977 |
| 5591035 | C | | | | | | G/C | cds_wt_4977 |
| 5591054 | C | A/C | C/A | C/A | C/A | C/A | A/C | cds_wt_4977 |
| 5591063 | T | | | | | | C/T | cds_wt_4977 |
| 5591065 | C | | | | | | G/C | cds_wt_4977 |
| 5591069 | A | | | | | | A/G | cds_wt_4977 |
| 5591074 | A | | | | | | G/A | cds_wt_4977 |
| 5591077 | C | | | | | | A/C | cds_wt_4977 |
| 5591092 | A | | | | | | G/A | cds_wt_4977 |
| 5591095 | G | | | | | | C/G | cds_wt_4977 |
| 5591098 | T | | | | | | C/T | cds_wt_4977 |
| 5591115 | G | | | | | | A/G | cds_wt_4977 |
| 5591158 | G | T/G | T/G | T/G | T/G | T/G | T/G | cds_wt_4977 |
| 5591179 | G | | | | | | T/G | cds_wt_4977 |
| 5591220 | C | | G/C | G/C | G/C | | G/C | cds_wt_4977 |
| 5591226 | A | | | G/A | G/A | | G/A | cds_wt_4977 |
| 5591268 | T | | | | | | C/T | cds_wt_4977 |
| 5591361 | C | | | | | | G/C | cds_wt_4977 |
| 5591442 | G | | | | | | A/G | cds_wt_4977 |
| 5591445 | C | | | | | | T/C | cds_wt_4977 |
| 5591457 | G | | | | | | C/G | cds_wt_4977 |
| 5591458 | A | | | | | | C/A | cds_wt_4977 |
| 5591466 | G | | | | | | C/G | cds_wt_4977 |
| 5591469 | G | | | | | | A/G | cds_wt_4977 |
| 5591472 | C | | | | | | G/C | cds_wt_4977 |
| 5591476 | A | | | | | | A/G | cds_wt_4977 |
| 5591496 | G | | | | | | C/G | cds_wt_4977 |
| 5591499 | A | | | | | | C/A | cds_wt_4977 |
| 5591505 | G | | | | | | C/G | cds_wt_4977 |
| 5591508 | T | | | | | | G/T | cds_wt_4977 |
| 5591520 | A | | | | | | G/A | cds_wt_4977 |
| 5591532 | C | | | | | | T/C | cds_wt_4977 |
| 5591541 | C | | | | | | T/C | cds_wt_4977 |
| 5591553 | G | | | | | | A/G | cds_wt_4977 |
| 5591562 | G | | | | | | T/G | cds_wt_4977 |
| 5591565 | G | | | | | | C/G | cds_wt_4977 |
| 5591571 | A | | | | | | G/A | cds_wt_4977 |
| 5591577 | A | | | | | | C/A | cds_wt_4977 |
| 5591596 | C | | | | | | T/C | cds_wt_4977 |
| 5591598 | G | | | | | | C/G | cds_wt_4977 |
| 5591607 | C | C/T | C/T | C/T | C/T | C/T | T/C | cds_wt_4977 |
| 5591613 | T | T/C | T/C | T/C | T/C | T/C | C/T | cds_wt_4977 |
| 5591632 | C | | | | | | A/C | cds_wt_4977 |
| 5591635 | G | | | | | | G/T | cds_wt_4977 |
| 5591640 | T | | | | | | T/C | cds_wt_4977 |
| 5591643 | C | | | | | | C/T | cds_wt_4977 |
| 5591654 | A | | | | | | A/C | cds_wt_4977 |
| 5591656 | A | | | | | | A/G | — |
| 5604643 | G | | A | A | A | A | A | cds_wt_4993 |
| 5612009 | C | | | T | T | T | T | cds_wt_5000 |
| 5626626 | C | T | T | T | T | T | T | — |
| 5629121 | C | | T | T | T | T | T | cds_wt_5011 |
| 5631426 | C | | | | | T | T | cds_wt_5015 |
| 5636810 | G | | A | A | A | A | A | cds_wt_5021 |
| 5657449 | C | T | T | T | T | T | T | cds_wt_5035 |
| 5659036 | G | | A | A | A | A | A | cds_wt_5036 |
| 5692125 | C | | | T | T | T | T | cds_wt_5065 |
| 5694507 | C | | | T | T | T | T | cds_wt_5069 |
| 5696833 | C | | | | | T | T | cds_wt_5070 |
| 5698190 | C | | T | T | T | T | T | — |
| 5705110 | C | | | T | T | T | T | cds_wt_5076 |
| 5708625 | C | | | T | T | T | T | cds_wt_5079 |
| 5709728 | C | | T | T | T | T | T | cds_wt_5079 |
| 5724677 | C | | | T | T | | T | cds_wt_5088 |
| 5727195 | C | | | | | | T | cds_wt_5090 |
| 5728510 | C | | | | | T | T | cds_wt_5091 |
| 5732980 | C | | | T | T | | T | cds_wt_5094 |
| 5738712 | G | | | | | | A | cds_wt_5097 |
| 5738846 | C | | | | | | T | cds_wt_5097 |
| 5745077 | C | | | | | | T | cds_wt_5099 |
| 5751489 | C | | | T | T | T | T | cds_wt_5101 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 5751716 | C | | | | | | T | cds_wt_5101 |
| 5753910 | C | | | T | T | T | T | cds_wt_5103 |
| 5755351 | C | | | T | T | T | T | cds_wt_5105 |
| 5756752 | C | | | | | | T | cds_wt_5107 |
| 5756803 | C | | | | | | T | cds_wt_5107 |
| 5760058 | C | | | | | | G | cds_wt_5110 |
| 5760301 | C | | | | | | T | cds_wt_5110 |
| 5763377 | C | | T | T | T | T | T | cds_wt_5111 |
| 5764363 | C | | | T | T | T | T | cds_wt_5111 |
| 5765100 | C | | | T | T | T | T | cds_wt_5111 |
| 5765446 | C | | | T | T | T | T | cds_wt_5111 |
| 5767623 | C | T | T | T | T | T | T | cds_wt_5113 |
| 5779664 | C | | | | | T | T | cds_wt_5122 |
| 5780052 | C | | | | | T | T | cds_wt_5122 |
| 5781808 | C | | | T | T | T | T | cds_wt_5123 |
| 5783477 | G | | A | A | A | A | A | — |
| 5788208 | C | | | T | T | T | T | cds_wt_5131 |
| 5790337 | C | | | T | T | T | T | cds_wt_5133 |
| 5791404 | C | | | T | T | T | T | cds_wt_5133 |
| 5793414 | G | A | A | A | A | A | A | cds_wt_5134 |
| 5795059 | C | | | T | T | T | T | — |
| 5795465 | G | | A | A | A | A | A | cds_wt_5136 |
| 5799803 | G | | | | | | A | cds_wt_5140 |
| 5803395 | C | | | T | T | T | T | cds_wt_5141 |
| 5803716 | G | | A | A | A | A | A | cds_wt_5141 |
| 5805398 | G | | A | A | A | A | A | cds_wt_5143 |
| 5805735 | G | | A | A | A | A | A | cds_wt_5143 |
| 5807160 | C | T | T | T | T | T | T | cds_wt_5145 |
| 5809295 | G | | | | | | A | cds_wt_5147 |
| 5810587 | G | | | | | A | A | — |
| 5811908 | C | | | | | | T | cds_wt_5148 |
| 5813504 | C | | | T | | | T | cds_wt_5149 |
| 5813556 | C | | T | T | T | T | T | cds_wt_5149 |
| 5834083 | C | | | | | | T | cds_wt_5170 |
| 5842153 | G | | | | | | C | cds_wt_5173 |
| 5843698 | T | | | | | | T/C | cds_wt_5173 |
| 5843724 | C | | | | | | C/A | cds_wt_5173 |
| 5843727 | C | | | | | | C/T | cds_wt_5173 |
| 5843751 | G | | | | | | G/A | cds_wt_5173 |
| 5843752 | G | | | | | | G/C | cds_wt_5173 |
| 5843766 | A | | | | | | A/G | cds_wt_5173 |
| 5843783 | A | | | | | | A/G | cds_wt_5173 |
| 5843786 | G | | | | | | G/C | cds_wt_5173 |
| 5843787 | C | | | | | | C/G | cds_wt_5173 |
| 5843795 | G | | | | | | G/C | cds_wt_5173 |
| 5843796 | T | | | | | | T/A | cds_wt_5173 |
| 5843797 | G | | | | | | G/T | cds_wt_5173 |
| 5843804 | C | | | | | | C/G | cds_wt_5173 |
| 5843810 | C | | | | | | C/T | cds_wt_5173 |
| 5843818 | T | | | | | | T/C | cds_wt_5173 |
| 5843819 | T | | | | | | T/G | cds_wt_5173 |
| 5843831 | C | | | | | | C/T | cds_wt_5173 |
| 5843863 | G | | | | | | G/T | cds_wt_5173 |
| 5843878 | C | | | | | | C/T | cds_wt_5173 |
| 5843881 | G | | | | | | G/T | cds_wt_5173 |
| 5843888 | G | | | | | | G/A | cds_wt_5173 |
| 5843890 | G | | | | | | G/C | cds_wt_5173 |
| 5843897 | C | | | | | | C/G | cds_wt_5173 |
| 5843899 | G | | | | | | G/T | cds_wt_5173 |
| 5843902 | C | | | | | | C/T | cds_wt_5173 |
| 5843942 | C | | | | | | C/T | cds_wt_5173 |
| 5843965 | G | | | | | | G/C | cds_wt_5173 |
| 5843980 | C | | | | | | C/G | cds_wt_5173 |
| 5843981 | C | | | | | | C/T | cds_wt_5173 |
| 5843987 | C | | | | | | C/G | cds_wt_5173 |
| 5843988 | C | | | | | | C/T | cds_wt_5173 |
| 5843992 | C | | | | | | C/T | cds_wt_5173 |
| 5857131 | C | | T | T | T | T | T | cds_wt_5188 |
| 5858663 | C | | | T | T | T | T | cds_wt_5190 |
| 5879695 | G | | A | A | A | A | A | cds_wt_5201 |
| 5880188 | T | | | | | | T/C | cds_wt_5201 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 5880203 | G | | | | | | G/C | cds_wt_5201 |
| 5880223 | C | | | | | | C/T | cds_wt_5201 |
| 5880241 | A | | | | | | A/C | cds_wt_5201 |
| 5880306 | C | | | | | | C/T | cds_wt_5201 |
| 5880307 | T | | | | | | T/C | cds_wt_5201 |
| 5880349 | A | | | | | | A/T | cds_wt_5201 |
| 5880412 | G | | | | | | G/A | cds_wt_5201 |
| 5880421 | C | | | | | | C/T | cds_wt_5201 |
| 5880430 | A | | | | | | A/G | cds_wt_5201 |
| 5880517 | T | T/C | T/C | T/C | T/C | T/C | T/C | cds_wt_5201 |
| 5882826 | G | | A | A | A | A | A | cds_wt_5202 |
| 5887657 | G | | | | | | C/G | cds_wt_5205 |
| 5887660 | G | | | | | | C/G | cds_wt_5205 |
| 5887684 | T | | | | | | C/T | cds_wt_5205 |
| 5887693 | T | | | | | | C/T | cds_wt_5205 |
| 5887696 | G | | | | | | C/G | cds_wt_5205 |
| 5887718 | G | | | | | | G/A | cds_wt_5205 |
| 5887732 | G | | | | | | G/C | cds_wt_5205 |
| 5887734 | G | | | | | | G/A | cds_wt_5205 |
| 5887765 | A | G/A | G/A | G/A | G/A | G/A | A/G/C | cds_wt_5205 |
| 5887771 | G | | | | | | G/C | cds_wt_5205 |
| 5887774 | G | | | | | | G/A | cds_wt_5205 |
| 5887775 | C | T/C | T/C | T/C | T/C | T/C | C/T | cds_wt_5205 |
| 5887784 | T | | | | T/C | | T/C | cds_wt_5205 |
| 5887792 | T | T/C | T/C | | T/C | | T/C | cds_wt_5205 |
| 5887810 | G | | | | | | G/C | cds_wt_5205 |
| 5887813 | G | | | | | | G/C | cds_wt_5205 |
| 5887816 | G | | | | | | G/C | cds_wt_5205 |
| 5887820 | G | G/C | G/C | G/C | G/C | G/C | G/C | cds_wt_5205 |
| 5887824 | C | C/G | C/G | C/G | C/G | C/G | C/G | cds_wt_5205 |
| 5887831 | G | | | | | | G/C | cds_wt_5205 |
| 5887837 | C | | | | | | C/T | cds_wt_5205 |
| 5887843 | C | | | | | | C/G | cds_wt_5205 |
| 5887892 | G | | A/G | A/G | A/G | A/G | A/G | cds_wt_5205 |
| 5887931 | G | G/A/C | A/G | G/A | G/A | G/A | G/A/C | cds_wt_5205 |
| 5887937 | G | | | | | | G/C | cds_wt_5205 |
| 5887938 | C | | | | | | C/G | cds_wt_5205 |
| 5887942 | C | | | | | | C/G | cds_wt_5205 |
| 5887945 | G | | | | | | G/C | cds_wt_5205 |
| 5887951 | G | | | | | | C/G | cds_wt_5205 |
| 5887960 | G | | | | | | G/C | cds_wt_5205 |
| 5887969 | G | | | | | | G/C | cds_wt_5205 |
| 5887970 | C | | | | | | C/G | cds_wt_5205 |
| 5887971 | A | | | | | | A/G | cds_wt_5205 |
| 5887974 | G | | | | | | G/T | cds_wt_5205 |
| 5887975 | C | | | | | | C/T | cds_wt_5205 |
| 5887977 | T | | | | | | T/A | cds_wt_5205 |
| 5887982 | C | | | | | | C/A/T | cds_wt_5205 |
| 5887988 | G | | | | | | G/T | cds_wt_5205 |
| 5887990 | C | | | | | | C/G | cds_wt_5205 |
| 5888003 | A | | | | | | A/C | cds_wt_5205 |
| 5888004 | A | | | | | | A/G | cds_wt_5205 |
| 5888005 | A | | | | | | A/G | cds_wt_5205 |
| 5888026 | C | | | | | | C/T | cds_wt_5205 |
| 5888050 | G | | | | | | G/C | cds_wt_5205 |
| 5888053 | G | | | | | | G/C | cds_wt_5205 |
| 5888056 | G | | | | | | G/C | cds_wt_5205 |
| 5888083 | G | | | | | | G/C | cds_wt_5205 |
| 5888092 | C | | | | | | C/G | cds_wt_5205 |
| 5888095 | C | | | | | | C/G | cds_wt_5205 |
| 5888102 | G | | | | | | G/A | cds_wt_5205 |
| 5888103 | T | | | | | | T/C | cds_wt_5205 |
| 5888122 | C | | | | | | C/T | cds_wt_5205 |
| 5888143 | G | | | | | | G/C | cds_wt_5205 |
| 5890782 | G | | | | | | G/C | cds_wt_5206 |
| 5890839 | T | T/C | T/C | T/C | T/C | T/C | C/T | cds_wt_5206 |
| 5890849 | T | | | | | | A/T | cds_wt_5206 |
| 5890851 | C | | | | | | G/C | cds_wt_5206 |
| 5890863 | C | | | | | | G/C | cds_wt_5206 |
| 5890864 | G | | | | | | A/G | cds_wt_5206 |
| 5890869 | G | | | | | | T/G | cds_wt_5206 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 5890872 | C | | | | | | T/C | cds_wt_5206 |
| 5890893 | C | | | | | | T/C | cds_wt_5206 |
| 5890899 | C | | | | | | T/C | cds_wt_5206 |
| 5890906 | G | | | | | | A/G | cds_wt_5206 |
| 5890908 | G | | | | | | G/A | cds_wt_5206 |
| 5890914 | C | | | | | | T/C | cds_wt_5206 |
| 5890920 | C | | | | | | G/C | cds_wt_5206 |
| 5890923 | C | | | | | | T/C | cds_wt_5206 |
| 5890926 | C | | | | | | G/C | cds_wt_5206 |
| 5890971 | C | | C/T | C/T | C/T | C/T | C/T | cds_wt_5206 |
| 5890992 | C | T/C | T/C | T/C | T/C | T/C | C/T | cds_wt_5206 |
| 5891058 | G | | | | | | C/G | cds_wt_5206 |
| 5891061 | G | | | | | | C/G | cds_wt_5206 |
| 5891070 | C | | | | | | T/C | cds_wt_5206 |
| 5891094 | T | | | | | | C/T | cds_wt_5206 |
| 5891097 | C | | | | | | C/G | cds_wt_5206 |
| 5891100 | C | | | | | | C/T | cds_wt_5206 |
| 5891121 | C | | | | | | T/C | cds_wt_5206 |
| 5891142 | G | | | | | | G/C | cds_wt_5206 |
| 5891145 | C | | | | | | C/G | cds_wt_5206 |
| 5891148 | G | | | | | | C/G | cds_wt_5206 |
| 5891187 | G | | G/C | G/C | G/C | G/C | G/C | cds_wt_5206 |
| 5891220 | G | | | | | | G/C | cds_wt_5206 |
| 5891247 | T | | | | | | T/C | cds_wt_5206 |
| 5891250 | C | | | | | | C/T | cds_wt_5206 |
| 5891263 | T | | | | | | T/C | cds_wt_5206 |
| 5892300 | C | | | | | | C/T | cds_wt_5206 |
| 5892304 | A | | | | | | A/C | cds_wt_5206 |
| 5892312 | C | | | | | | C/G | cds_wt_5206 |
| 5892330 | C | | | | | | C/T | cds_wt_5206 |
| 5892370 | A | | | | | | A/G | cds_wt_5206 |
| 5892413 | C | | | | | | C/T | cds_wt_5206 |
| 5892414 | T | | | | | | T/C | cds_wt_5206 |
| 5892456 | A | | | | | | A/T | cds_wt_5206 |
| 5892519 | G | G/A | G/A | G/A | G/A | G/A | G/A | cds_wt_5206 |
| 5894264 | G | | | | | | A | cds_wt_5207 |
| 5894322 | G | | | | | | A | cds_wt_5207 |
| 5894986 | A | | | | | | A/G | cds_wt_5207 |
| 5894989 | T | | | | | | T/C | cds_wt_5207 |
| 5895041 | G | | | | | | G/A | cds_wt_5207 |
| 5895043 | C | | | | | | C/G | cds_wt_5207 |
| 5895049 | C | | | | | | C/G | cds_wt_5207 |
| 5895054 | T | | | | | | T/C | cds_wt_5207 |
| 5895058 | G | | | | | | G/C | cds_wt_5207 |
| 5895073 | C | C/G | C/G | C/G | C/G | C/G | C/G | cds_wt_5207 |
| 5895100 | G | G/C | G/C | G/C | | | G/C | cds_wt_5207 |
| 5895106 | C | | | | | | G/C | cds_wt_5207 |
| 5895108 | T | | | | | | C/T | cds_wt_5207 |
| 5895115 | C | | | | | | G/C | cds_wt_5207 |
| 5895118 | A | | | | | | C/A | cds_wt_5207 |
| 5895127 | C | | | | | | G/C | cds_wt_5207 |
| 5895130 | C | | | | | | G/C | cds_wt_5207 |
| 5895137 | A | | | | | | T/A | cds_wt_5207 |
| 5895142 | T | | | | | | C/T | cds_wt_5207 |
| 5895147 | G | | | | | | C/G | cds_wt_5207 |
| 5895181 | C | C/T | C/T | C/T | C/T | C/T | T/C | cds_wt_5207 |
| 5895254 | A | | | | | | G/A | cds_wt_5207 |
| 5895280 | T | T/C | C/T | T/C | T/C | T/C | C/T | cds_wt_5207 |
| 5895283 | G | G/C | G/C | G/C | G/C | G/C | C/G | cds_wt_5207 |
| 5895298 | C | C/G | C/G | C/G | C/G | C/G | G/C | cds_wt_5207 |
| 5895299 | G | G/A | G/A | G/A | G/A | G/A | A/G | cds_wt_5207 |
| 5895319 | C | | | | | | G/C | cds_wt_5207 |
| 5895328 | C | | | | | | T/C | cds_wt_5207 |
| 5895334 | C | | | | | | T/C | cds_wt_5207 |
| 5895340 | G | | | | | | C/G | cds_wt_5207 |
| 5895346 | G | | | | | | G/C | cds_wt_5207 |
| 5895349 | C | | | | | | T/C | cds_wt_5207 |
| 5895358 | C | | | | | | T/C | cds_wt_5207 |
| 5895361 | C | | | | | | G/C | cds_wt_5207 |
| 5895370 | C | | | | | | C/T | cds_wt_5207 |
| 5895391 | C | | | | | | T/C | cds_wt_5207 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 5895436 | G | | | | | | C/G | cds_wt_5207 |
| 5895437 | A | | | | | | G/A | cds_wt_5207 |
| 5895439 | C | | | | | | G/C | cds_wt_5207 |
| 5895493 | G | | G/C | G/C | G/C | G/C | C/G | cds_wt_5207 |
| 5895496 | G | | G/C | G/C | G/C | G/C | C/G | cds_wt_5207 |
| 5895505 | C | | | | | | T/C | cds_wt_5207 |
| 5895529 | T | T/C | C/T | T/C | T/C | T/C | C/T | cds_wt_5207 |
| 5895532 | C | C/G | G/C | C/G | C/G | C/G | G/C | cds_wt_5207 |
| 5895577 | G | | | | | | C/G | cds_wt_5207 |
| 5895580 | C | | | | | | G/C | cds_wt_5207 |
| 5895628 | T | | | | | | C/T/G | cds_wt_5208 |
| 5895629 | T | | | | | | C/T | cds_wt_5208 |
| 5895661 | C | | | | | | C/G | cds_wt_5208 |
| 5895847 | C | C/G | C/G | C/G | C/G | C/G | C/G | cds_wt_5208 |
| 5895878 | G | G/A | | G/A | G/A | G/A | G/A | cds_wt_5208 |
| 5895898 | C | | C/T | C/T | C/T | C/T | C/T | cds_wt_5208 |
| 5895899 | A | | A/C | A/C | | A/C | A/C | cds_wt_5208 |
| 5895915 | A | A/G | A/G | A/G | A/G | A/G | G/A | cds_wt_5208 |
| 5895949 | C | | | | | | T/C | cds_wt_5208 |
| 5896081 | C | C/G | C/G | C/G | C/G | C/G | G/C | cds_wt_5208 |
| 5896085 | C | C/T | C/T | C/T | C/T | | T/C | cds_wt_5208 |
| 5896090 | C | C/T | C/T | C/T | C/T | | T/C | cds_wt_5208 |
| 5896115 | C | | | | | | C/T | cds_wt_5208 |
| 5896120 | A | | | | | | A/G | cds_wt_5208 |
| 5896123 | G | | | | | | G/C | cds_wt_5208 |
| 5896126 | T | | | | | | T/C | cds_wt_5208 |
| 5896147 | T | | | | | | T/G | cds_wt_5208 |
| 5896148 | T | | | | | | T/C | cds_wt_5208 |
| 5896154 | T | | | | | | T/C | cds_wt_5208 |
| 5896156 | G | | | | | | G/C | cds_wt_5208 |
| 5896159 | G | | | | | | G/C | cds_wt_5208 |
| 5896246 | T | | | | | | T/C | cds_wt_5208 |
| 5896279 | C | | | | | | T/C | cds_wt_5208 |
| 5896312 | A | | | | | | A/G | cds_wt_5208 |
| 5896324 | A | | | | | | A/G | cds_wt_5208 |
| 5896333 | G | | | | | | G/A | cds_wt_5208 |
| 5896381 | G | | | | | | G/C | cds_wt_5208 |
| 5900925 | C | | | | | | C/G | cds_wt_5209 |
| 5900943 | G | | | | | | G/T | cds_wt_5209 |
| 5900949 | C | | | | | | C/G | cds_wt_5209 |
| 5900955 | C | | | | | | C/T | cds_wt_5209 |
| 5900958 | C | | | | | | C/G | cds_wt_5209 |
| 5900965 | T | | | | | | T/C | cds_wt_5209 |
| 5900971 | G | | | | | | G/C | cds_wt_5209 |
| 5900972 | C | | | | | | C/G | cds_wt_5209 |
| 5900997 | C | | | | | | C/T | cds_wt_5209 |
| 5901000 | C | | | | | | C/T | cds_wt_5209 |
| 5901015 | A | | | | | | A/C | cds_wt_5209 |
| 5901034 | C | | | | | | C/A | cds_wt_5209 |
| 5901048 | C | | | | | | C/T | cds_wt_5209 |
| 5901050 | G | | | | | | G/A | cds_wt_5209 |
| 5901057 | C | | | | | | C/T | cds_wt_5209 |
| 5901068 | G | | | | | | G/A | cds_wt_5209 |
| 5901071 | A | | | | | | A/G | cds_wt_5209 |
| 5901078 | G | G/T | G/T | | | G/T | G/T | cds_wt_5209 |
| 5901099 | C | C/T | C/T | C/T | C/T | C/T | C/T | cds_wt_5209 |
| 5901123 | T | | | | | | T/A | cds_wt_5209 |
| 5901135 | G | | | | | | C/G | cds_wt_5209 |
| 5901172 | G | | | | | | A/G | cds_wt_5209 |
| 5901186 | G | | | | | | G/A | cds_wt_5209 |
| 5901195 | T | | | | | | T/C | cds_wt_5209 |
| 5901204 | G | | | | | | G/A | cds_wt_5209 |
| 5901219 | C | | | | | | A/C | cds_wt_5209 |
| 5901342 | T | T/C | T/C | T/C | T/C | T/C | C/T | cds_wt_5209 |
| 5901345 | T | | | | | | T/G | cds_wt_5209 |
| 5901346 | T | | | | | | T/C | cds_wt_5209 |
| 5901354 | C | | | | | | C/G | cds_wt_5209 |
| 5901615 | C | T/C | T/C | T/C | T/C | T/C | T/C | cds_wt_5209 |
| 5901617 | G | C/G | C/G | C/G | C/G | C/G | C/G | cds_wt_5209 |
| 5901660 | C | | | | | | C/G | cds_wt_5209 |
| 5901664 | T | T/G | T/G | T/G | T/G | T/G | T/G | cds_wt_5209 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 5901669 | C | C/A | C/A | | C/A | C/A | A/C | cds_wt_5209 |
| 5901673 | T | | | | | | A/T | cds_wt_5209 |
| 5901675 | C | | | | | | G/C | cds_wt_5209 |
| 5901679 | C | | | | | | C/T | cds_wt_5209 |
| 5901688 | C | | | | | | T/C | cds_wt_5209 |
| 5901689 | T | | | | | | A/T | cds_wt_5209 |
| 5901690 | G | | | | | | C/G | cds_wt_5209 |
| 5901698 | C | | | | | | A/C | cds_wt_5209 |
| 5901712 | G | | | | | | A/G | cds_wt_5209 |
| 5901713 | T | | | | | | A/T | cds_wt_5209 |
| 5901714 | T | | | | | | T/C | cds_wt_5209 |
| 5901719 | G | | | | | | G/C | cds_wt_5209 |
| 5901726 | G | | | | | | G/C | cds_wt_5209 |
| 5901729 | C | | | | | | C/G | cds_wt_5209 |
| 5901732 | C | | | | | | C/T | cds_wt_5209 |
| 5901733 | G | | | | | | G/A | cds_wt_5209 |
| 5901738 | C | | | | | | C/G | cds_wt_5209 |
| 5901752 | C | | | | | | C/T | cds_wt_5209 |
| 5901757 | G | | | | | | G/A | cds_wt_5209 |
| 5901764 | T | | | | | | C/T | cds_wt_5209 |
| 5901767 | C | | | | | | G/C | cds_wt_5209 |
| 5901771 | G | | | | | | C/G | cds_wt_5209 |
| 5901790 | C | | | | | | G/C | cds_wt_5209 |
| 5901791 | G | | | | | | C/G | cds_wt_5209 |
| 5901793 | G | | | | | | A/G | cds_wt_5209 |
| 5901807 | G | | | | | | C/G | cds_wt_5209 |
| 5901824 | G | | | | | | A/G | cds_wt_5209 |
| 5901826 | G | | | | | | G/A | cds_wt_5209 |
| 5901830 | T | | | | | | T/G | cds_wt_5209 |
| 5901840 | A | | | | | | A/C | cds_wt_5209 |
| 5902914 | C | T | T | T | T | T | T | cds_wt_5209 |
| 5905708 | G | | A | A | A | A | A | cds_wt_5211 |
| 5925008 | C | T | T | T | T | T | T | — |
| 5925517 | G | | A | A | A | A | A | cds_wt_5227 |
| 5926357 | G | | | | | | A | cds_wt_5228 |
| 5928875 | C | | | | | T | T | cds_wt_5231 |
| 5930205 | C | T | T | T | T | T | T | cds_wt_5232 |
| 5933164 | G | A | A | A | A | A | A | — |
| 5947433 | C | T | T | T | T | T | T | cds_wt_5246 |
| 5957471 | G | | | A | A | A | A | — |
| 5960825 | C | | T | T | T | T | T | cds_wt_5274 |
| 5961809 | T | G/T | | | G/T | G/T | G/T | cds_wt_5275 |
| 5961866 | T | | | | | | T/A | — |
| 5970914 | C | | T | T | T | T | T | cds_wt_5279 |
| 5975910 | A | A/G | A/G | A/G | A/G | A/G | G/A | cds_wt_5283 |
| 5975911 | A | A/G | A/G | A/G | A/G | A/G | G/A | — |
| 5975926 | A | A/G | A/G | A/G | A/G | A/G | G/A | — |
| 5978267 | C | T | T | T | T | T | T | cds_wt_5286 |
| 6005749 | C | | T | T | T | T | T | cds_wt_5311 |
| 6009383 | G | A | A | A | A | A | A | cds_wt_5315 |
| 6010024 | C | | | T | T | T | T | cds_wt_5316 |
| 6026234 | C | | T | T | T | T | T | — |
| 6033950 | C | T | T | T | T | T | T | cds_wt_5324 |
| 6042035 | C | | | | | | T | — |
| 6050103 | C | | | | | C/T | C/T | cds_wt_5343 |
| 6050112 | A | | | | | | C/A | cds_wt_5343 |
| 6050115 | G | | | | | | G/C | cds_wt_5343 |
| 6050116 | C | | | | | | C/G | cds_wt_5343 |
| 6050118 | G | | | | | | G/A | cds_wt_5343 |
| 6050509 | G | G/A | A/G | A/G | A/G | A/G | A/G | cds_wt_5343 |
| 6050536 | G | | | | | | G/C | cds_wt_5343 |
| 6050556 | G | | | | | | C/G | cds_wt_5343 |
| 6050557 | C | | | | | | A/C | cds_wt_5343 |
| 6050584 | T | | | | | | T/A | cds_wt_5343 |
| 6050694 | T | | | | | | T/C | cds_wt_5343 |
| 6050727 | A | | | G/A | G/A | G/A | G/A | cds_wt_5343 |
| 6050730 | G | | C/G | C/G | C/G | C/G | C/G | cds_wt_5343 |
| 6050769 | G | | | | | | G/A | cds_wt_5343 |
| 6050820 | A | | | | | | A/C | cds_wt_5343 |
| 6050822 | T | | | | | | T/C | cds_wt_5343 |
| 6050824 | C | | | | | | C/T | cds_wt_5343 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 6050947 | T | | | | | | C/T | cds_wt_5343 |
| 6050949 | A | | | | | | G/A | cds_wt_5343 |
| 6050952 | T | | | | | | T/C | cds_wt_5343 |
| 6050958 | G | | | | | | A/G | cds_wt_5343 |
| 6050965 | A | | | | | | C/A | cds_wt_5343 |
| 6050971 | T | | | | | | C/T | cds_wt_5343 |
| 6051079 | A | G/A | G/A | G/A | G/A | G/A | A/G | cds_wt_5343 |
| 6051571 | G | A | A | A | A | A | A | — |
| 6072579 | C | | | | T | T | T | — |
| 6074412 | G | A | A | A | A | A | A | — |
| 6075058 | G | A | A | A | A | A | A | — |
| 6083188 | C | | | | | T | T | — |
| 6085177 | C | | | | | T | T | cds_wt_5373 |
| 6090298 | C | | T | T | T | T | T | cds_wt_5376 |
| 6094419 | C | T | T | T | T | T | T | cds_wt_5383 |
| 6095825 | C | T | T | T | T | T | T | cds_wt_5386 |
| 6098808 | C | T | T | T | T | T | T | cds_wt_5388 |
| 6099142 | C | T | T | T | T | T | T | cds_wt_5388 |
| 6099801 | C | T | T | T | T | T | T | — |
| 6100131 | C | T | T | T | T | T | T | cds_wt_5389 |
| 6100928 | C | T | T | T | T | T | T | cds_wt_5389 |
| 6114598 | C | | T | T | T | T | T | cds_wt_5399 |
| 6129757 | G | A | A | A | A | A | A | — |
| 6151020 | G | A | A | A | A | A | A | cds_wt_5451 |
| 6157309 | C | | T | T | T | T | T | cds_wt_5456 |
| 6157376 | C | | T | T | T | T | T | cds_wt_5456 |
| 6178150 | G | | A | A | A | A | A | cds_wt_5472 |
| 6188180 | C | | T | T | T | T | T | cds_wt_5481 |
| 6191683 | G | A | | | A | | A | cds_wt_5487 |
| 6207945 | G | A | A | A | A | A | A | cds_wt_5501 |
| 6216366 | C | | T | T | | T | T | cds_wt_5511 |
| 6230439 | A | | G | G | G | | G | cds_wt_5526 |
| 6251389 | G | | A | A | A | A | A | cds_wt_5542 |
| 6251652 | G | | A | A | A | A | A | cds_wt_5542 |
| 6255100 | G | | A | A | A | A | A | cds_wt_5546 |
| 6264179 | G | | | A | A | A | A | cds_wt_5554 |
| 6265855 | G | | A | A | A | A | A | — |
| 6267856 | G | | | A | A | A | A | cds_wt_5556 |
| 6278700 | G | A | A | A | A | A | A | — |
| 6281103 | C | | | | | T | T | cds_wt_5566 |
| 6282875 | C | | T | T | T | T | T | cds_wt_5567 |
| 6286620 | C | | | | | T | T | cds_wt_5571 |
| 6288364 | C | | T | T | T | T | T | cds_wt_5571 |
| 6291716 | C | | T | T | T | T | T | cds_wt_5574 |
| 6297821 | C | | T | T | T | T | T | cds_wt_5578 |
| 6303632 | G | | | | | A | A | cds_wt_5583 |
| 6306219 | C | | T | T | T | T | T | cds_wt_5586 |
| 6309112 | G | | | | | A | A | cds_wt_5588 |
| 6322894 | G | | | | | | A | — |
| 6328731 | C | T | T | T | T | T | T | cds_wt_5605 |
| 6331035 | G | A | A | A | A | A | A | cds_wt_5607 |
| 6338677 | G | A | A | A | A | A | A | cds_wt_5615 |
| 6339429 | C | | | | | T | T | — |
| 6344180 | C | | | | T | T | T | cds_wt_5619 |
| 6346415 | C | | | | T | | T | cds_wt_5622 |
| 6361477 | C | | T | T | T | T | T | cds_wt_5639 |
| 6362282 | G | | | A | A | A | A | cds_wt_5639 |
| 6366940 | C | T | | | T | | T | cds_wt_5641 |
| 6368217 | G | | | | | A | A | cds_wt_5643 |
| 6369699 | G | | | | | A | A | cds_wt_5644 |
| 6375315 | G | A | A | A | A | A | A | cds_wt_5648 |
| 6381431 | C | | T | T | T | T | T | cds_wt_5654 |
| 6401947 | G | A | A | | | A | A | — |
| 6403645 | C | | | | T | T | T | cds_wt_5675 |
| 6437676 | C | T | T | T | T | T | T | cds_wt_5697 |
| 6439389 | G | | | | | A | A | cds_wt_5698 |
| 6450624 | C | | T | T | T | T | T | — |
| 6454248 | C | | T | T | T | T | T | cds_wt_5708 |
| 6454843 | C | | | | | T | T | — |
| 6456678 | C | | | | | T | T | cds_wt_5711 |
| 6456912 | C | | T | T | T | T | T | cds_wt_5712 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 6459047 | G | | | | | | A | cds_wt_5715 |
| 6460584 | T | | C | C | C | C | C | — |
| 6471884 | G | | | | | A | A | cds_wt_5729 |
| 6485358 | C | | T | T | T | T | T | cds_wt_5741 |
| 6499172 | G | | | A | A | A | A | cds_wt_5757 |
| 6500551 | G | | | | | | A | cds_wt_5760 |
| 6507389 | C | T | T | T | T | T | T | cds_wt_5765 |
| 6517707 | C | | | T | T | | T | — |
| 6525706 | G | | | | | A | A | cds_wt_5775 |
| 6538378 | C | | | | | T | T | cds_wt_5786 |
| 6542765 | C | | T | T | T | T | T | cds_wt_5790 |
| 6543445 | C | | T | T | T | T | T | cds_wt_5791 |
| 6543579 | C | | T | T | T | T | T | cds_wt_5791 |
| 6545779 | C | | T | T | T | T | T | cds_wt_5792 |
| 6550507 | C | | | | | T | T | cds_wt_5797 |
| 6553219 | G | | A | A | A | A | A | cds_wt_5800 |
| 6553546 | G | | A | | | | A | cds_wt_5800 |
| 6553589 | G | | A | A | A | A | A | cds_wt_5800 |
| 6555594 | G | | A | A | A | A | A | cds_wt_5804 |
| 6556192 | C | | | | | | T | cds_wt_5804 |
| 6560301 | C | | T | T | T | T | T | — |
| 6561416 | G | | A | A | A | A | A | cds_wt_5810 |
| 6563658 | C | | T | T | | | T | cds_wt_5812 |
| 6564054 | C | | T | T | T | T | T | cds_wt_5812 |
| 6564511 | C | | | T | T | T | T | cds_wt_5813 |
| 6564827 | C | | T | T | T | T | T | cds_wt_5813 |
| 6567102 | C | | T | T | T | T | T | cds_wt_5815 |
| 6567313 | C | | | | | T | T | cds_wt_5816 |
| 6568360 | C | | | | T | | T | cds_wt_5817 |
| 6569524 | C | | T | T | T | T | T | cds_wt_5819 |
| 6569696 | G | | A | A | A | A | A | cds_wt_5819 |
| 6570943 | C | | T | T | T | T | T | cds_wt_5820 |
| 6572188 | C | | | T | T | | T | cds_wt_5821 |
| 6572441 | C | | | T | T | | T | cds_wt_5821 |
| 6580904 | G | | A | A | A | A | A | cds_wt_5830 |
| 6581219 | G | | | | | | G/A | cds_wt_5830 |
| 6589934 | C | | T | T | T | T | T | cds_wt_5837 |
| 6595494 | C | T | | T | T | | T | — |
| 6604343 | C | | | | | | T | cds_wt_5851 |
| 6615272 | C | | | | | | T | cds_wt_5859 |
| 6617190 | G | A | A | A | A | A | A | cds_wt_5861 |
| 6619058 | C | | | | | | T | cds_wt_5862 |
| 6622561 | G | A | A | A | A | A | A | cds_wt_5864 |
| 6629950 | C | | | | T | T | T | cds_wt_5870 |
| 6632292 | C | T | T | T | T | T | T | cds_wt_5872 |
| 6656015 | C | T | | | | T | T | cds_wt_5891 |
| 6669477 | G | | | | | A | A | cds_wt_5901 |
| 6690831 | C | | T | T | T | T | T | cds_wt_5923 |
| 6690855 | G | | | | | A | A | cds_wt_5923 |
| 6696960 | G | | | | | A | A | — |
| 6705369 | G | | A | A | A | A | A | cds_wt_5935 |
| 6716231 | G | | A | A | A | A | A | — |
| 6729998 | G | | A | A | A | A | A | cds_wt_5955 |
| 6734341 | C | | | | T | T | T | cds_wt_5960 |
| 6758247 | G | | | | | A | A | cds_wt_5984 |
| 6759384 | C | | | | | | T | cds_wt_5985 |
| 6767085 | G | | | | | A | A | cds_wt_5990 |
| 6769984 | C | | | | T | T | T | cds_wt_5994 |
| 6780798 | A | | | G | G | G | G | cds_wt_6005 |
| 6801699 | G | A | A | A | A | A | A | cds_wt_6025 |
| 6805336 | G | A | A | A | A | A | A | cds_wt_6026 |
| 6805990 | G | A | A | A | A | A | A | cds_wt_6026 |
| 6808471 | C | | T | T | T | T | T | — |
| 6818998 | G | | A | A | A | A | A | cds_wt_6038 |
| 6830990 | G | | | | | A | A | cds_wt_6049 |
| 6843179 | C | | | | | | T | cds_wt_6061 |
| 6847192 | G | | | | | | A | cds_wt_6063 |
| 6854404 | C | | | | | | T | cds_wt_6068 |
| 6858684 | G | | A | A | A | A | A | cds_wt_6073 |
| 6883984 | C | | T | T | T | T | T | cds_wt_6092 |
| 6884717 | G | | | | | A | A | cds_wt_6092 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 6890659 | G | | A | A | A | A | A | cds_wt_6098 |
| 6892977 | G | | A | A | A | A | A | cds_wt_6100 |
| 6898871 | C | | T | T | T | T | T | cds_wt_6107 |
| 6902839 | A | T | T | T | T | T | T | cds_wt_6112 |
| 6911746 | G | | A | A | A | A | A | cds_wt_6117 |
| 6916561 | G | A | A | A | A | A | A | cds_wt_6122 |
| 6916943 | C | | T | T | T | T | T | cds_wt_6122 |
| 6927456 | G | A | | A | A | | A | cds_wt_6133 |
| 6960103 | G | | A | A | A | A | A | cds_wt_6158 |
| 6961070 | C | | | | | T | T | cds_wt_6159 |
| 6968534 | C | T | T | T | T | T | T | — |
| 6973392 | G | | A | A | A | A | A | — |
| 6987945 | G | | A | A | A | A | A | cds_wt_6176 |
| 6993597 | G | | | | A | A | A | cds_wt_6181 |
| 6995391 | C | | T | T | T | T | T | cds_wt_6182 |
| 6996621 | C | | | | | | T | cds_wt_6183 |
| 6999127 | C | | T | T | T | T | T | cds_wt_6187 |
| 6999520 | C | | | | | T | T | cds_wt_6187 |
| 6999817 | C | | T | T | T | T | T | cds_wt_6188 |
| 7000264 | C | | T | T | T | T | T | cds_wt_6188 |
| 7002458 | G | | A | A | A | A | A | cds_wt_6190 |
| 7003486 | G | | | | | A | A | cds_wt_6192 |
| 7003496 | G | | | | | A | A | cds_wt_6192 |
| 7004068 | C | T | T | T | T | T | T | cds_wt_6193 |
| 7009952 | C | | | | | T | T | — |
| 7010119 | C | | | | | T | T | cds_wt_6198 |
| 7010712 | C | | | | | T | T | cds_wt_6199 |
| 7015917 | G | | A | A | A | A | A | cds_wt_6203 |
| 7019067 | C | | T | T | T | T | T | — |
| 7019437 | C | | T | T | T | T | T | cds_wt_6206 |
| 7020227 | C | | T | T | T | T | T | cds_wt_6207 |
| 7021026 | C | | T | T | T | T | T | cds_wt_6209 |
| 7023202 | C | | T | T | T | T | T | cds_wt_6212 |
| 7024113 | C | | | | | T | T | cds_wt_6213 |
| 7026584 | C | | T | T | T | T | T | cds_wt_6217 |
| 7028273 | C | | T | T | T | T | T | cds_wt_6218 |
| 7028622 | C | | | | | T | T | cds_wt_6218 |
| 7029812 | C | | | | | | T | cds_wt_6219 |
| 7031076 | C | | | | | | T | cds_wt_6219 |
| 7040546 | C | T | T | T | T | T | T | cds_wt_6233 |
| 7053643 | C | | T | T | T | T | T | cds_wt_6243 |
| 7065316 | C | | T | T | T | T | T | cds_wt_6252 |
| 7075215 | C | | T | T | T | T | T | cds_wt_6264 |
| 7098642 | C | | T | T | T | T | T | cds_wt_6283 |
| 7099792 | C | | T | T | T | T | T | cds_wt_6284 |
| 7100617 | C | | | T | T | T | T | cds_wt_6285 |
| 7101023 | C | | T | T | T | T | T | cds_wt_6285 |
| 7103392 | C | | T | T | T | T | T | — |
| 7104098 | C | | T | T | T | T | T | cds_wt_6288 |
| 7109594 | C | | T | T | T | T | T | cds_wt_6291 |
| 7110600 | C | | T | T | T | T | T | cds_wt_6293 |
| 7110641 | C | | T | T | T | T | T | cds_wt_6293 |
| 7112833 | C | | T | T | T | T | T | cds_wt_6295 |
| 7116801 | C | T | T | T | T | T | T | cds_wt_6297 |
| 7135624 | G | A | A | A | A | A | A | cds_wt_6314 |
| 7135635 | G | A | | | | | A | cds_wt_6314 |
| 7146220 | G | | A | A | A | A | A | — |
| 7160415 | C | | T | T | T | | T | — |
| 7161529 | G | | A | A | A | A | A | cds_wt_6338 |
| 7162249 | G | | A | A | A | A | A | cds_wt_6338 |
| 7165660 | C | | | | T | T | T | — |
| 7176091 | G | A | A | A | A | | A | cds_wt_6348 |
| 7177869 | G | A | A | A | A | A | A | cds_wt_6350 |
| 7185280 | G | | | | | | A | cds_wt_6354 |
| 7186525 | C | | T | T | T | T | T | cds_wt_6355 |
| 7211965 | G | | | | | | G/C | cds_wt_6378 |
| 7211966 | A | | | | | | A/T | cds_wt_6378 |
| 7211975 | C | | | | | | C/T | cds_wt_6378 |
| 7211983 | G | | | | | | G/T | cds_wt_6378 |
| 7211992 | G | | | | | | G/T | cds_wt_6378 |
| 7211994 | G | | | | | | G/A | cds_wt_6378 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 7212006 | T | | | | | | T/C | cds_wt_6378 |
| 7212047 | C | | | | | | C/G | cds_wt_6378 |
| 7212067 | T | | | | | | T/A | cds_wt_6378 |
| 7212068 | G | | | | | | G/C | cds_wt_6378 |
| 7212075 | G | | | | | | G/C | cds_wt_6378 |
| 7212088 | A | | | | | | A/T | cds_wt_6378 |
| 7212097 | T | | | | | | T/C | cds_wt_6378 |
| 7212113 | T | | | | | | T/C | cds_wt_6378 |
| 7212121 | G | | | | | | G/T | cds_wt_6378 |
| 7212122 | T | | | | | | T/C | cds_wt_6378 |
| 7212142 | T | | | | | | T/C | cds_wt_6378 |
| 7212144 | C | | | | | | C/G | cds_wt_6378 |
| 7212151 | T | | | | | | T/G | cds_wt_6378 |
| 7212156 | G | | | | | | G/C | cds_wt_6378 |
| 7212180 | C | | | | | | C/G | cds_wt_6378 |
| 7212182 | G | | | | | | G/C | cds_wt_6378 |
| 7212183 | T | | | | | | T/C | cds_wt_6378 |
| 7212206 | T | | | | | | T/C | cds_wt_6378 |
| 7216330 | G | A | A | A | A | A | A | cds_wt_6380 |
| 7218939 | G | A | A | A | A | A | A | — |
| 7219494 | G | | | | | A | A | — |
| 7224067 | G | | | | | | A | cds_wt_6388 |
| 7228023 | G | | | | | | A | — |
| 7240925 | G | A | | A | A | | A | cds_wt_6398 |
| 7241497 | C | | | T | T | | T | cds_wt_6399 |
| 7264121 | G | | A | A | A | A | A | cds_wt_6416 |
| 7266647 | G | A | A | A | A | A | A | cds_wt_6419 |
| 7283171 | C | T | T | T | T | T | T | cds_wt_6434 |
| 7294161 | A | | G | G | G | G | G | — |
| 7303836 | C | T | T | T | T | T | T | cds_wt_6454 |
| 7310019 | G | | A | A | A | A | A | cds_wt_6461 |
| 7314132 | C | | T | T | T | T | T | cds_wt_6463 |
| 7314146 | C | | T | T | T | T | T | cds_wt_6463 |
| 7319151 | G | A | A | A | A | A | A | cds_wt_6467 |
| 7319658 | G | | A | A | A | A | A | cds_wt_6467 |
| 7321495 | G | | | | | | A | cds_wt_6470 |
| 7329181 | G | | A | A | A | A | A | cds_wt_6478 |
| 7330808 | G | | A | A | A | A | A | cds_wt_6480 |
| 7362245 | C | | | | | T | T | cds_wt_6510 |
| 7369374 | C | | | | | T | T | cds_wt_6518 |
| 7371536 | C | | | | | T | T | cds_wt_6520 |
| 7377855 | C | | T | T | T | T | T | cds_wt_6527 |
| 7384932 | G | A | A | A | A | A | A | cds_wt_6533 |
| 7385124 | C | | T | T | T | T | T | cds_wt_6533 |
| 7386113 | G | | A | A | A | A | A | cds_wt_6533 |
| 7389303 | C | | T | T | T | T | T | cds_wt_6535 |
| 7394213 | C | | T | T | T | T | T | cds_wt_6540 |
| 7394997 | C | | | | | T | T | cds_wt_6540 |
| 7400636 | C | | | | | T | T | — |
| 7401592 | C | | T | T | T | T | T | cds_wt_6544 |
| 7422484 | G | | A | A | A | A | A | cds_wt_6563 |
| 7446288 | G | | | | | | A | — |
| 7451085 | C | | T | T | T | T | T | — |
| 7452627 | C | | T | T | T | T | T | cds_wt_6589 |
| 7453489 | C | T | T | T | T | T | T | cds_wt_6590 |
| 7453910 | C | | T | T | T | T | T | cds_wt_6591 |
| 7460642 | C | | T | T | T | T | T | cds_wt_6600 |
| 7462223 | G | A | A | A | A | A | A | cds_wt_6601 |
| 7484067 | C | T | T | T | T | T | T | — |
| 7490770 | G | | | | | A | A | cds_wt_6634 |
| 7492384 | G | | | | | | A | cds_wt_6634 |
| 7498836 | G | | A | A | A | A | A | cds_wt_6639 |
| 7511194 | G | | | | | | A | cds_wt_6648 |
| 7517188 | G | | A | A | A | A | A | cds_wt_6653 |
| 7518982 | C | T | T | T | T | T | T | cds_wt_6654 |
| 7524203 | G | | A | A | A | A | A | cds_wt_6659 |
| 7525798 | C | | T | T | T | T | T | cds_wt_6660 |
| 7546077 | C | | T | T | T | T | T | — |
| 7583090 | G | | A | A | A | A | A | — |
| 7588792 | C | | T | T | T | T | T | cds_wt_6730 |
| 7598819 | G | | A | A | A | A | A | — |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 7600514 | G | | | | | A | A | cds_wt_6738 |
| 7604996 | G | | | | | | A | cds_wt_6743 |
| 7607903 | G | | A | A | A | A | A | cds_wt_6746 |
| 7622689 | G | | A | A | A | A | A | cds_wt_6763 |
| 7627683 | G | | | | | | G/T | cds_wt_6770 |
| 7630530 | G | A | A | A | A | A | A | cds_wt_6772 |
| 7639840 | G | | | | | A | A | cds_wt_6784 |
| 7641043 | G | | | | | | A | cds_wt_6785 |
| 7646004 | G | A | A | A | A | A | A | cds_wt_6788 |
| 7648704 | G | A | A | A | A | A | A | cds_wt_6791 |
| 7652691 | G | A | A | A | A | A | A | cds_wt_6794 |
| 7654254 | G | A | A | A | A | A | A | — |
| 7655513 | G | A | A | A | A | A | A | — |
| 7662521 | G | | A | | A | | A | — |
| 7671626 | C | | | T | T | T | T | cds_wt_6808 |
| 7672126 | G | | | | | | A | cds_wt_6808 |
| 7687061 | G | | | | | | A | cds_wt_6826 |
| 7689723 | G | | A | A | A | A | A | cds_wt_6829 |
| 7714246 | C | | T | T | T | T | T | cds_wt_6856 |
| 7718521 | G | | A | A | A | A | A | cds_wt_6860 |
| 7719226 | G | | A | A | A | A | A | cds_wt_6861 |
| 7719430 | G | | A | A | A | A | A | cds_wt_6861 |
| 7720998 | G | | A | A | A | A | A | cds_wt_6862 |
| 7731353 | G | | A | A | A | A | A | cds_wt_6874 |
| 7733376 | G | | | | | A | A | cds_wt_6876 |
| 7736672 | C | | | | | | C/T | cds_wt_6879 |
| 7740086 | C | T | T | T | T | T | T | cds_wt_6883 |
| 7740896 | G | | | | A | A | A | cds_wt_6884 |
| 7765137 | G | | A | A | A | A | A | cds_wt_6902 |
| 7772239 | G | | A | A | A | A | A | cds_wt_6912 |
| 7789263 | G | A | A | A | A | A | A | cds_wt_6933 |
| 7790304 | G | | | | | | A | cds_wt_6933 |
| 7801751 | G | | A | A | A | A | A | cds_wt_6947 |
| 7802623 | T | | | | | | T/C | — |
| 7802638 | T | | | | | | T/C | — |
| 7802639 | C | | | | | | C/T | — |
| 7802682 | A | | T | T | T | T | T | — |
| 7809752 | G | | | | | A | A | cds_wt_6953 |
| 7809834 | G | | | | | A | A | cds_wt_6953 |
| 7823754 | C | T | T | T | T | T | T | cds_wt_6968 |
| 7825882 | G | | | | A | A | A | cds_wt_6969 |
| 7832540 | G | A | A | A | A | A | A | cds_wt_6976 |
| 7838339 | C | | T | T | T | T | T | cds_wt_6980 |
| 7841392 | C | | T | T | T | T | T | cds_wt_6983 |
| 7841997 | C | | T | T | T | T | T | cds_wt_6983 |
| 7842274 | C | | T | T | T | T | T | cds_wt_6984 |
| 7844241 | G | | A | A | A | A | A | cds_wt_6985 |
| 7855301 | C | | T | T | T | T | T | cds_wt_6993 |
| 7864327 | G | A | A | A | A | A | A | — |
| 7874843 | C | | | | | | T | cds_wt_7008 |
| 7883195 | A | | | | | | G | cds_wt_7018 |
| 7889441 | G | | A | A | A | A | A | cds_wt_7022 |
| 7909245 | G | A | A | A | A | A | A | cds_wt_7036 |
| 7912017 | A | | | | | | G | cds_wt_7038 |
| 7917279 | G | | A | A | A | A | A | cds_wt_7040 |
| 7926998 | G | A | A | A | A | A | A | cds_wt_7045 |
| 7931764 | G | | A | A | A | A | A | cds_wt_7049 |
| 7934819 | G | | A | A | A | A | A | cds_wt_7051 |
| 7948630 | C | T | T | T | T | T | T | cds_wt_7068 |
| 7963950 | G | | A | A | A | A | A | cds_wt_7082 |
| 7967045 | G | | | A | A | A | A | cds_wt_7086 |
| 7969374 | G | A | A | A | A | A | A | cds_wt_7089 |
| 7984213 | G | | A | A | A | A | A | cds_wt_7101 |
| 7984254 | G | | A | A | A | A | A | cds_wt_7101 |
| 7985275 | G | A | | A | | | A | cds_wt_7103 |
| 8009877 | C | T | T | T | T | T | T | cds_wt_7127 |
| 8026754 | C | T | | | | | T | cds_wt_7145 |
| 8036245 | C | | T | T | T | T | T | cds_wt_7152 |
| 8042744 | G | | | A | A | A | A | cds_wt_7156 |
| 8051051 | G | A | A | A | A | A | A | cds_wt_7165 |
| 8053700 | C | | | | | | T | cds_wt_7169 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 8062905 | A | | | | | | T | — |
| 8062911 | C | | | | | | T | — |
| 8075410 | C | T | T | T | T | T | T | cds_wt_7189 |
| 8077440 | G | | A | A | A | A | A | cds_wt_7191 |
| 8087405 | G | A | A | A | A | A | A | cds_wt_7205 |
| 8094018 | G | | A | A | A | A | A | cds_wt_7211 |
| 8095401 | G | A | | | | | A | cds_wt_7213 |
| 8096270 | C | T | | | | | T | cds_wt_7214 |
| 8122172 | G | | | | | | A | cds_wt_7240 |
| 8123295 | G | | A | A | A | A | A | cds_wt_7241 |
| 8123721 | G | | A | A | A | A | A | cds_wt_7241 |
| 8136640 | C | | T | T | T | T | T | cds_wt_7254 |
| 8161493 | C | | T | T | T | T | T | cds_wt_7274 |
| 8165695 | A | | | | | | A/T | cds_wt_7279 |
| 8165703 | A | | | | | | A/G | cds_wt_7279 |
| 8165704 | C | | | | | | C/G | cds_wt_7279 |
| 8167086 | G | | A | A | A | A | A | cds_wt_7280 |
| 8171741 | G | A | A | A | A | A | A | cds_wt_7283 |
| 8179169 | G | | | | A | A | A | cds_wt_7288 |
| 8181933 | G | A | A | A | A | A | A | cds_wt_7290 |
| 8186618 | C | T | T | T | T | T | T | cds_wt_7297 |
| 8193241 | C | | | T | T | T | T | cds_wt_7306 |
| 8195170 | C | | T | T | T | T | T | cds_wt_7307 |
| 8195310 | C | | T | T | T | T | T | cds_wt_7307 |
| 8199221 | G | A | A | A | A | A | A | cds_wt_7312 |
| 8202704 | C | | | | | | C/T | cds_wt_7315 |
| 8205853 | G | A | A | A | A | A | A | cds_wt_7319 |
| 8212158 | C | T | T | T | T | T | T | cds_wt_7324 |
| 8212583 | G | | | | | A | A | cds_wt_7324 |
| 8214951 | C | | T | T | T | T | T | cds_wt_7328 |
| 8221459 | G | A | A | A | A | A | A | cds_wt_7335 |
| 8227017 | G | | | | | | A | cds_wt_7340 |
| 8233448 | C | | | | | T | T | cds_wt_7347 |
| 8237580 | G | | | | | | A | cds_wt_7349 |
| 8239310 | G | | | | | | A | cds_wt_7349 |
| 8240439 | G | | | | | A | A | cds_wt_7350 |
| 8241289 | G | | A | A | A | A | A | cds_wt_7350 |
| 8243590 | G | A | A | A | A | A | A | — |
| 8247542 | G | | A | A | A | A | A | cds_wt_7357 |
| 8248207 | C | | | | | | T | cds_wt_7357 |
| 8256006 | G | | A | A | A | A | A | cds_wt_7367 |
| 8263792 | G | | A | A | A | A | A | cds_wt_7373 |
| 8267543 | G | | A | A | A | A | A | cds_wt_7377 |
| 8272330 | G | | | | | | A | cds_wt_7379 |
| 8273351 | C | | T | T | T | T | T | cds_wt_7380 |
| 8278809 | G | | | | | A | A | cds_wt_7384 |
| 8282707 | G | | | | | | A | cds_wt_7387 |
| 8298405 | T | T/A | T/A | | T/A | | T/A | cds_wt_7401 |
| 8298413 | C | C/G | | C/G | C/G | C/G | C/G | cds_wt_7401 |
| 8302281 | G | A | A | A | A | A | A | cds_wt_7405 |
| 8311927 | T | | C | C | C | C | C | cds_wt_7413 |
| 8323622 | C | | T | T | T | T | T | cds_wt_7423 |
| 8325049 | G | | | | | | G/C | cds_wt_7424 |
| 8325050 | A | | | | | | G/A | cds_wt_7424 |
| 8325073 | C | C/G | C/G | C/G | C/G | C/G | C/G | cds_wt_7424 |
| 8325095 | G | | | | | | G/C | cds_wt_7424 |
| 8325096 | G | | | | | | G/T | cds_wt_7424 |
| 8325102 | C | | | | | | C/G | cds_wt_7424 |
| 8325109 | T | | | | | | C/T | cds_wt_7424 |
| 8325115 | C | | | | | | G/C | cds_wt_7424 |
| 8325118 | C | | | | | | C/G | cds_wt_7424 |
| 8325121 | G | | | | | | G/C | cds_wt_7424 |
| 8325127 | G | | | | | | G/C | cds_wt_7424 |
| 8325133 | C | | | | | | G/C | cds_wt_7424 |
| 8325203 | T | | | | | T/C | T/C | cds_wt_7424 |
| 8325210 | A | A/G | A/G | A/G | A/G | A/G | G/A | cds_wt_7424 |
| 8325277 | C | | | | | | C/G | cds_wt_7424 |
| 8325286 | C | | | | | | C/G | cds_wt_7424 |
| 8349257 | G | | | | A | A | A | cds_wt_7444 |
| 8351616 | G | | | | A | A | A | cds_wt_7445 |
| 8355565 | C | | | | | T | T | cds_wt_7448 |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 8355924 | C | | T | T | T | T | T | cds_wt_7448 |
| 8363036 | G | A | A | A | A | A | A | cds_wt_7452a |
| 8364757 | C | T | T | T | T | T | T | cds_wt_7454 |
| 8365293 | G | A | A | A | A | A | A | cds_wt_7454 |
| 8368404 | G | | | A | A | A | A | cds_wt_7457 |
| 8378911 | G | | A | A | A | A | A | cds_wt_7464 |
| 8379977 | G | | | A | A | A | A | — |
| 8380006 | C | | | | | | T | — |
| 8381094 | G | | A | A | A | A | A | cds_wt_7465 |
| 8384806 | G | | | | A | A | A | cds_wt_7468 |
| 8389000 | C | | | | | T | T | cds_wt_7470 |
| 8389283 | A | G | G | G | G | G | G | cds_wt_7470 |
| 8393915 | G | | A | A | A | A | A | cds_wt_7472 |
| 8396831 | G | | | | | | A | cds_wt_7476 |
| 8397563 | G | | | | A | A | A | cds_wt_7476 |
| 8402662 | G | | A | A | A | A | A | — |
| 8411820 | C | | | T | T | T | T | cds_wt_7490 |
| 8413318 | C | T | T | T | T | T | T | cds_wt_7491 |
| 8414872 | C | | T | T | T | T | T | cds_wt_7491 |
| 8431655 | T | A/T | A/T | A/T | A/T | A/T | T/A | — |
| 8441210 | C | T | | | T | T | T | cds_wt_7510 |
| 8449495 | G | | | | | | G/A | cds_wt_7513 |
| 8453858 | G | | | | A | | A | cds_wt_7514 |
| 8463714 | G | | | | | A | A | cds_wt_7525 |
| 8466767 | G | | A | A | A | A | A | cds_wt_7529 |
| 8491536 | G | A | A | A | A | A | A | — |
| 8497636 | C | | | | | | T | cds_wt_7552 |
| 8506267 | G | | | A | A | A | A | cds_wt_7561 |
| 8509227 | G | | | | | | A | cds_wt_7562 |
| 8515828 | G | | A | A | A | A | A | cds_wt_7566 |
| 8529144 | G | | A | A | A | A | A | cds_wt_7572 |
| 8544731 | G | | A | A | A | A | A | — |
| 8546526 | C | T | T | T | T | T | T | cds_wt_7591 |
| 8556565 | G | | A | | | | A | — |
| 8559522 | G | A | A | A | A | A | A | cds_wt_7602 |
| 8560241 | C | | | | | | T | cds_wt_7603 |
| 8567608 | C | | T | T | T | T | T | cds_wt_7607 |
| 8572238 | C | | | | | T | T | — |
| 8576774 | G | A | | A | A | A | A | — |
| 8582623 | C | | | | | T | T | cds_wt_7615 |
| 8589455 | C | | | | | T | T | cds_wt_7621 |
| 8589459 | C | | | | | T | T | cds_wt_7621 |
| 8595339 | C | T | T | T | T | T | T | cds_wt_7627 |
| 8610015 | C | | T | T | T | T | T | cds_wt_7640 |
| 8622039 | C | T | T | T | T | T | T | cds_wt_7652 |
| 8631175 | G | A | A | A | A | A | A | cds_wt_7660 |
| 8640526 | C | | T | T | T | T | T | cds_wt_7667 |
| 8646416 | G | | A | A | A | A | A | cds_wt_7674 |
| 8647802 | G | | A | A | A | A | A | cds_wt_7675 |
| 8648408 | G | | | | A | A | A | cds_wt_7676 |
| 8655581 | C | T | T | T | T | T | T | cds_wt_7683 |
| 8658688 | G | | A | A | A | A | A | cds_wt_7685 |
| 8668191 | C | | T | T | T | T | T | cds_wt_7693 |
| 8668196 | G | | A | A | A | A | A | cds_wt_7693 |
| 8669919 | G | A | A | A | A | A | A | — |
| 8674137 | C | T | T | T | T | T | T | cds_wt_7700 |
| 8678961 | G | | A | A | A | A | A | cds_wt_7704 |
| 8682722 | G | A | A | A | A | A | A | — |
| 8690364 | C | T | T | T | T | T | T | cds_wt_7711 |
| 8691972 | C | | | | | | T | cds_wt_7712 |
| 8699652 | G | | A | A | A | A | A | cds_wt_7716 |
| 8699708 | G | | A | A | A | A | A | cds_wt_7716 |
| 8709561 | C | | T | T | T | T | T | — |
| 8720459 | G | A | A | A | A | A | A | cds_wt_7731 |
| 8731485 | G | | | | | A | A | cds_wt_7745 |
| 8737851 | G | A | A | A | A | A | A | cds_wt_7749 |
| 8737859 | G | A | A | A | A | A | A | cds_wt_7749 |
| 8742265 | C | | T | | T | T | T | cds_wt_7750 |
| 8743148 | C | | | T | T | | T | cds_wt_7751 |
| 8754468 | G | | A | A | A | A | A | — |
| 8754501 | G | | A | A | A | A | A | — |

-continued

| Position in reference wild type strain SE50-100 | Base in Reference strain | Occurrence in Strain | | | | | | Affected Gene ID |
|---|---|---|---|---|---|---|---|---|
| | | SN223-29-47 | C445-P47 | SN12755-48 | SC3687-18-43 | SC7177-40-17 | SN19910-27-21 | |
| 8759529 | G | | | | | | A | cds_wt_7757 |
| 8761290 | C | | T | T | T | T | T | cds_wt_7757 |
| 8769464 | T | | | | | C | C | — |
| 8792629 | G | | A | A | A | A | A | cds_wt_7788 |
| 8793001 | C | T | T | T | T | T | T | cds_wt_7788 |
| 8809351 | C | | T | T | T | T | T | cds_wt_7801 |
| 8813761 | C | | T | T | T | T | T | cds_wt_7803 |
| 8813866 | C | | T | T | T | T | T | cds_wt_7803 |
| 8816396 | G | A | A | A | A | A | A | cds_wt_7805 |
| 8821923 | G | | A | A | A | A | A | cds_wt_7810 |
| 8825490 | G | | A | A | A | A | A | cds_wt_7813 |
| 8828064 | C | | T | T | T | T | T | cds_wt_7815 |
| 8841828 | G | A | A | A | A | A | A | cds_wt_7827 |
| 8842797 | G | | | | | A | A | cds_wt_7828 |
| 8843541 | G | | | | | | A | cds_wt_7828 |
| 8845199 | T | | C | C | C | C | C | cds_wt_7829 |
| 8848419 | G | A | A | A | A | A | A | cds_wt_7832 |
| 8849052 | G | A | A | A | A | A | A | cds_wt_7833 |
| 8854017 | C | | | T | T | T | T | cds_wt_7839 |
| 8854256 | G | | A | A | A | A | A | cds_wt_7839 |
| 8858030 | G | | A | A | A | A | A | cds_wt_7843 |
| 8859328 | G | | | | | | A | cds_wt_7844 |
| 8860995 | G | | | A | | | A | cds_wt_7846 |
| 8861382 | G | | A | A | A | A | A | — |
| 8871894 | C | T | T | T | T | T | T | — |
| 8872344 | C | | | | | | C/T | cds_wt_7854 |
| 8875526 | G | | A | A | A | A | A | cds_wt_7858 |
| 8881555 | G | | | | A | A | A | cds_wt_7864 |
| 8889242 | G | | | | | | A | cds_wt_7871 |
| 8893686 | G | A | A | A | A | A | A | cds_wt_7877 |
| 8894581 | G | A | A | A | A | A | A | — |
| 8896018 | G | A | A | A | A | A | A | cds_wt_7879 |
| 8901982 | G | A | A | A | A | A | A | cds_wt_7883 |
| 8902511 | G | | A | A | A | A | A | cds_wt_7883 |
| 8902844 | G | | A | A | A | A | A | cds_wt_7884 |
| 8902903 | G | | A | A | A | A | A | cds_wt_7884 |
| 8907784 | G | A | A | A | A | A | A | — |
| 8927137 | G | | | | | | A | — |
| 8929703 | G | A | A | A | A | A | A | cds_wt_7911 |
| 8931762 | C | T | T | T | T | T | T | cds_wt_7914 |
| 8934108 | G | | | | | A | A | cds_wt_7916 |
| 8937518 | C | | | | | | T | cds_wt_7919 |
| 8943513 | C | | | | | | T | cds_wt_7925 |
| 8943676 | C | | | | | | T | cds_wt_7925 |
| 8944024 | C | | | | | | T | — |
| 8945415 | C | | | T | T | T | T | — |
| 8946251 | C | | | T | T | T | T | cds_wt_7927 |
| 8948806 | G | | A | A | A | A | A | cds_wt_7930 |
| 8950622 | C | T | T | T | T | T | T | cds_wt_7931 |
| 8951908 | C | | T | T | T | T | T | cds_wt_7932 |
| 8953417 | G | A | | A | A | | A | cds_wt_7935 |
| 8955117 | G | | | | | A | A | cds_wt_7936 |
| 8956021 | C | | | | | | T | cds_wt_7937 |
| 8956608 | C | | | | | | T | cds_wt_7937 |
| 8958843 | C | T | | | T | T | T | cds_wt_7939 |
| 8959688 | G | | | A | A | A | A | cds_wt_7940 |
| 8974326 | G | | A | A | A | A | A | cds_wt_7953 |
| 8979884 | C | | | T | T | T | T | cds_wt_7957 |
| 8982938 | G | G/C | G/C | | | | G/C | cds_wt_7963 |
| 8982956 | G | G/C | G/C | G/C | G/C | G/C | G/C | cds_wt_7963 |
| 8982975 | G | | | | | | G/C | cds_wt_7963 |
| 8983002 | G | G/A | G/A | G/A | G/A | G/A | G/A | — |
| 8983053 | C | C/T | C/T | C/T | C/T | C/T | C/T | cds_wt_7964 |
| 8983087 | G | | | | | | A/G | cds_wt_7964 |
| 8983088 | G | | | | | | G/C | cds_wt_7964 |
| 8983102 | A | A/G | A/G | A/G | A/G | A/G | G/A | cds_wt_7964 |
| 8983134 | G | G/C | G/C | G/C | G/C | G/C | G/C | cds_wt_7964 |
| 9008254 | C | | | | | | T | cds_wt_7977 |
| 9028349 | G | A | A | A | A | A | A | cds_wt_7991 |
| 9029056 | C | | | | | T | T | cds_wt_7991 |
| 9045846 | G | | A | A | A | A | A | cds_wt_7996 |

-continued

| Position in reference wild type strain SE50-100 | Base in Reference strain | SN223-29-47 | C445-P47 | SN12755-48 | SC3687-18-43 | SC7177-40-17 | SN19910-27-21 | Affected Gene ID |
|---|---|---|---|---|---|---|---|---|
| 9049564 | C | | | | | | T | cds_wt_7998 |
| 9052240 | C | T | T | T | T | T | T | cds_wt_8000 |
| 9052265 | G | | | A | A | A | A | cds_wt_8000 |
| 9053107 | G | A | A | A | A | A | A | — |
| 9058239 | G | A | A | A | A | A | A | cds_wt_8006 |
| 9060181 | C | | T | T | T | T | T | cds_wt_8008 |
| 9064090 | C | T | T | T | T | T | T | cds_wt_8011 |
| 9072129 | C | | | | | | C/T | cds_wt_8017 |

Summary of Identified COG Categories

Table 10 shows details on COG-classified genes of the *A. utahensis* wild type strain SE50-100. For each COG category and its subcategories, the number of annotated genes and the absolute percentage is listed.

| COG-Categories | Population | |
|---|---|---|
| CDS with COG-category | 3,983 | (49.62%) |
| Information storage and processing | 1240 | (15.45%) |
| Translation. ribosomal structure and biogenesis | 200 | (2.49%) |
| RNA processing and modification | 2 | (0.02%) |
| Transcription | 771 | (9.61%) |
| Replication. recombination and repair | 266 | (3.31%) |
| Chromatin structure and dynamics | 1 | (0.01%) |
| Cellular processes and signaling | 1398 | (17.42%) |
| Cell cycle control. cell division. chromosome partitioning | 49 | (0.61%) |
| Nuclear structure | 0 | (0.00%) |
| Defense mechanisms | 84 | (1.05%) |
| Signal transduction mechanisms | 592 | (7.38%) |
| Cell wall/membrane/envelope biogenesis | 302 | (3.76%) |
| Cell motility | 104 | (1.30%) |
| Cytoskeleton | 8 | (0.10%) |
| Extracellular structures | 0 | (0.00%) |
| Intracellular trafficking. secretion. and vesicular transport | 89 | (1.11%) |
| Posttranslational modification. protein turnover. chaperones | 170 | (2.12%) |
| Metabolism | 2409 | (30.01%) |
| Energy production and conversion | 308 | (3.84%) |
| Carbohydrate transport and metabolism | 575 | (7.16%) |
| Amino acid transport and metabolism | 521 | (6.49%) |
| Nucleotide transport and metabolism | 82 | (1.02%) |
| Coenzyme transport and metabolism | 187 | (2.33%) |
| Lipid transport and metabolism | 234 | (2.92%) |
| Inorganic ion transport and metabolism | 257 | (3.20%) |
| Secondary metabolites biosynthesis. transport and catabolism | 245 | (3.05%) |

All Genes with Annotation

Table 11 lists all annotated genes of the *Actinoplanes utahensis* wild type strain SE50-100.

Lengthy table referenced here

US09719064-20170801-T00001

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US09719064B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09719064B2). An electronic copy of the "Sequence Listing" will also be available from the USPTO upon request and payment of the fee set forth in 37 CFR 1.19(b)(3).

The invention claimed is:
1. A mutated comprising DNA the nucleotide sequence of SEQ ID NO.: 16053 and the mutations shown in the Table below:

| Position in SEQ ID 16053 | Nucleotide in SEQ ID 16053 | Mutated Nucleotide |
|---|---|---|
| 7102 | G | A |
| 11919 | G | A |
| 12285 | G | A |
| 12651 | G | A |
| 13511 | G | A |
| 46974 | C | T |
| 62542 | C | T |
| 64957 | C | T |
| 65055 | C | T |
| 65455 | C | T/C |
| 65460 | C | T |
| 65882 | G | A |
| 72685 | A | A/G |
| 72693 | A | A/G |
| 72701 | A | A/G |
| 73373 | C | T |
| 73467 | C | T |
| 76845 | C | T |
| 78965 | C | T |
| 80653 | G | A |
| 85503 | G | A |
| 88269 | G | A |
| 88369 | G | A |
| 89368 | C | T |
| 89901 | C | T |
| 90029 | C | T |
| 91949 | C | T |
| 93427 | C | T |
| 101351 | G | A |
| 103967 | C | T |
| 104063 | C | T |
| 110857 | C | T |
| 112637 | G | A |
| 114499 | G | A |
| 115250 | G | A |
| 115873 | C | T |
| 115983 | C | T |
| 117494 | C | T |
| 119344 | G | A |
| 134489 | C | T |
| 139515 | C | T |
| 146767 | C | T |
| 161035 | G | A |
| 172303 | G | A |
| 176176 | G | A |
| 178880 | G | G/A |
| 180754 | C | T |
| 180925 | C | T |
| 184674 | G | A |
| 190568 | C | T |
| 190644 | C | T |
| 191971 | C | T |
| 193584 | G | A |
| 196028 | C | T |
| 196338 | C | T |
| 214992 | G | A |
| 222841 | G | A |
| 222924 | C | T |
| 228543 | C | T |
| 247200 | C | T |
| 248952 | C | T |
| 253299 | G | A |
| 254551 | G | A |
| 259829 | C | T |
| 268705 | C | T |
| 270822 | G | A |
| 273723 | G | A |
| 276430 | C | T |
| 276561 | C | T |
| 283007 | G | A |
| 283062 | G | A |
| 287132 | C | T |
| 294767 | G | A |
| 295356 | C | T |
| 300028 | C | T |
| 303810 | G | A |
| 313837 | C | T |
| 316698 | G | A |
| 316929 | G | A |
| 325503 | C | T |
| 331088 | G | A |
| 340040 | G | A |
| 342987 | G | A |
| 343915 | G | A |
| 352688 | C | T |
| 353668 | G | A |
| 361019 | G | A |
| 362742 | G | A |
| 375835 | C | T |
| 381358 | G | A |
| 382029 | G | A |
| 391677 | C | T |
| 400166 | C | T |
| 406413 | G | A |
| 409544 | G | A |
| 416199 | G | A |
| 419938 | C | T |
| 425067 | G | A |
| 425419 | G | A |
| 426464 | G | A |
| 438324 | C | T |
| 446368 | G | A |
| 446984 | G | A |
| 447392 | G | A |
| 450492 | G | A |
| 458678 | C | T |
| 459753 | C | T |
| 459833 | A | G |
| 466505 | G | A |
| 474923 | G | A |
| 482599 | G | A |
| 494993 | G | A |
| 500358 | C | T |
| 510408 | C | T |
| 511515 | G | A |
| 512816 | G | A |
| 513902 | C | T |
| 515197 | G | A |
| 518156 | G | A |
| 533618 | G | A |
| 536327 | C | T |
| 542891 | G | A |
| 548989 | C | T |
| 553081 | G | A |
| 553332 | G | A |
| 557884 | G | A |
| 557907 | C | A |
| 567026 | C | T |
| 587166 | A | G |
| 590721 | G | A |
| 602225 | C | T |
| 604184 | C | T |
| 605918 | C | T |
| 621774 | C | T |
| 624361 | C | T |
| 625600 | C | T |
| 626283 | G | A |
| 629283 | G | A |
| 636108 | C | T |
| 648981 | G | A |
| 684062 | Ci | A |
| 702171 | C | T |
| 702650 | C | T |
| 703452 | C | T |
| 706109 | C | T |
| 711168 | G | A |
| 712462 | A | A/G |
| 714678 | G | A |

| Position in SEQ ID 16053 | Nucleotide in SEQ ID 16053 | Mutated Nucleotide |
|---|---|---|
| 714785 | G | A |
| 717602 | G | A |
| 719600 | G | A |
| 724097 | G | A |
| 738525 | C | T |
| 744594 | G | A |
| 746362 | G | A |
| 750285 | C | T |
| 752663 | G | A |
| 763762 | C | C/G |
| 763785 | G | G/C |
| 763792 | C | C/G |
| 763951 | C | C/G |
| 765635 | G | A |
| 766073 | G | A |
| 769289 | G | A |
| 776043 | C | T |
| 780677 | C | T |
| 781916 | C | T |
| 783900 | C | T |
| 786653 | G | A |
| 795572 | C | T |
| 796824 | G | A |
| 798663 | G | A |
| 810530 | G | A |
| 810533 | C | G |
| 810556 | T | T/C |
| 810557 | G | G/C |
| 810563 | C | C/T |
| 810576 | A | A/G |
| 819250 | G | A |
| 829153 | C | T |
| 830171 | C | T |
| 831404 | G | A |
| 838352 | G | A |
| 842068 | G | A |
| 847887 | G | A |
| 861775 | C | T |
| 870304 | G | A |
| 880820 | C | T |
| 897424 | C | T |
| 907842 | G | A |
| 908987 | C | T |
| 921289 | G | A |
| 941088 | G | A |
| 945666 | G | A |
| 959932 | C | T |
| 964504 | G | A |
| 964558 | C | T |
| 970334 | C | T |
| 972781 | C | T |
| 995285 | G | A |
| 1004653 | C | T |
| 1006503 | C | T |
| 1008680 | G | A |
| 1009674 | G | A |
| 1009813 | G | A |
| 1023301 | C | T |
| 1028963 | G | A |
| 1030345 | C | T |
| 1030822 | G | A |
| 1037262 | G | A |
| 1041811 | C | T |
| 1054013 | C | T |
| 1055406 | C | T |
| 1082623 | G | A |
| 1085482 | C | T |
| 1085499 | C | T |
| 1088995 | C | T |
| 1097530 | C | T |
| 1107807 | T | A |
| 1117905 | C | T |
| 1119169 | G | A |
| 1120103 | G | A |
| 1120852 | G | A |
| 1122832 | C | T |
| 1123080 | C | T |
| 1128153 | G | A |
| 1130585 | G | A |
| 1145784 | C | T |
| 1146897 | G | A |
| 1153166 | C | T |
| 1163219 | C | T |
| 1163309 | G | A |
| 1163538 | G | A |
| 1169629 | C | T |
| 1169882 | C | T |
| 1170591 | C | T |
| 1172808 | C | T |
| 1172940 | C | T |
| 1173551 | C | T |
| 1179238 | C | A |
| 1192548 | C | T |
| 1194346 | C | T |
| 1194637 | G | A |
| 1196403 | C | T |
| 1208932 | C | T |
| 1221399 | C | T |
| 1222202 | C | T |
| 1225212 | C | T |
| 1242677 | G | A |
| 1249095 | C | T |
| 1250477 | G | A |
| 1255855 | C | T |
| 1260719 | C | T |
| 1261347 | C | T |
| 1261926 | C | T |
| 1262307 | G | A |
| 1262367 | G | A |
| 1267545 | C | T |
| 1270664 | C | T |
| 1272928 | C | T |
| 1273797 | C | T |
| 1277491 | G | A |
| 1282245 | G | A |
| 1284346 | C | T |
| 1285883 | C | T |
| 1291340 | C | T |
| 1300654 | G | A |
| 1306705 | C | T |
| 1307526 | C | T |
| 1308200 | C | T |
| 1315876 | C | T |
| 1317961 | G | A |
| 1321981 | C | T |
| 1322304 | C | T |
| 1325473 | C | T |
| 1325983 | G | A |
| 1327837 | C | T |
| 1329364 | C | T |
| 1330802 | G | A |
| 1335338 | C | T |
| 1342390 | C | T |
| 1343472 | A | C |
| 1344261 | C | T |
| 1346995 | C | T |
| 1348395 | G | A |
| 1351344 | C | T |
| 1352745 | C | T |
| 1356389 | C | T |
| 1359105 | G | A |
| 1359182 | C | T |
| 1362032 | C | T |
| 1370065 | G | A |
| 1370088 | C | T |
| 1379821 | C | T |
| 1382638 | G | A |
| 1388800 | C | T |
| 1404278 | C | T |
| 1409508 | G | A |
| 1410045 | G | A |
| 1413757 | G | A |

| Position in SEQ ID 16053 | Nucleotide in SEQ ID 16053 | Mutated Nucleotide |
|---|---|---|
| 1415711 | G | A |
| 1415773 | G | A |
| 1418132 | C | T |
| 1419671 | G | A |
| 1420016 | C | T |
| 1428228 | C | T |
| 1428233 | C | T |
| 1435884 | C | T |
| 1438355 | C | T |
| 1440872 | G | A |
| 1443149 | C | T |
| 1450678 | G | A |
| 1453590 | G | A |
| 1454075 | C | T |
| 1455191 | G | A |
| 1463521 | C | T |
| 1473239 | C | T |
| 1474775 | G | A |
| 1482297 | C | T |
| 1494980 | G | A |
| 1502729 | G | A |
| 1514463 | C | T |
| 1525258 | G | A |
| 1533361 | C | T |
| 1545597 | T | T/C |
| 1563822 | C | T |
| 1563854 | C | T |
| 1565818 | C | T |
| 1566866 | C | T |
| 1570236 | G | A |
| 1570636 | C | T |
| 1581033 | T | C |
| 1594972 | G | A |
| 1614616 | C | T |
| 1615586 | C | T |
| 1616152 | C | T |
| 1616981 | C | T |
| 1617561 | C | T |
| 1617928 | C | T |
| 1622589 | G | A |
| 1641656 | C | T |
| 1641711 | C | T |
| 1641953 | C | T |
| 1648653 | G | A |
| 1648676 | G | A |
| 1649444 | C | T |
| 1650400 | G | A |
| 1658589 | G | A |
| 1661376 | G | A |
| 1664324 | C | T |
| 1680524 | C | T |
| 1682349 | G | A |
| 1682842 | C | T |
| 1686608 | C | T |
| 1695571 | C | T |
| 1699167 | G | A |
| 1700705 | G | A |
| 1715788 | T | C |
| 1727072 | G | A |
| 1747963 | C | T |
| 1748448 | C | T |
| 1778278 | C | T |
| 1779396 | C | T |
| 1779723 | C | T |
| 1792608 | G | A |
| 1793069 | C | T |
| 1795610 | C | T |
| 1803172 | C | T |
| 1805902 | C | T |
| 1815104 | C | T |
| 1848170 | G | A |
| 1858054 | C | T |
| 1874864 | G | A |
| 1878368 | C | T |
| 1878456 | C | T |
| 1881797 | G | A |
| 1881821 | G | A |
| 1883780 | G | A |
| 1886024 | G | A |
| 1886177 | G | A |
| 1886499 | G | A |
| 1888003 | G | A |
| 1888277 | G | A |
| 1891012 | G | A |
| 1891205 | C | T |
| 1891493 | G | A |
| 1891608 | G | A |
| 1895230 | C | T |
| 1896121 | G | A |
| 1898465 | G | A |
| 1904126 | G | A |
| 1904415 | G | A |
| 1918600 | G | A |
| 1926767 | G | A |
| 1930239 | G | A |
| 1933689 | G | A |
| 1935111 | G | A |
| 1938524 | G | A |
| 1941158 | G | A |
| 1950155 | C | T |
| 1961896 | C | T |
| 1964247 | C | T |
| 1971635 | A | C |
| 1973884 | G | A |
| 1985968 | G | A |
| 1986215 | C | T |
| 1987891 | C | T |
| 1987907 | C | T |
| 1993612 | G | A |
| 1997079 | C | T |
| 2043866 | G | A |
| 2043889 | G | A |
| 2048938 | C | T |
| 2058063 | G | A |
| 2058998 | G | A |
| 2060664 | G | A |
| 2060796 | G | A |
| 2067415 | G | A |
| 2067911 | G | A |
| 2071535 | G | A |
| 2077305 | A | G/A |
| 2077309 | T | C/T |
| 2077321 | A | G/A |
| 2077324 | G | A/G |
| 2077336 | A | G/A |
| 2077351 | C | T/C |
| 2077353 | A | G/A |
| 2077369 | C | T/C |
| 2077383 | G | A/G |
| 2077384 | C | G/C |
| 2077398 | G | G/C |
| 2077432 | T | C/T |
| 2077603 | A | G/A |
| 2077615 | C | A/C |
| 2077618 | G | A/G |
| 2077636 | T | C/T |
| 2077645 | G | C/G |
| 2077651 | G | C/G |
| 2077652 | A | G/A |
| 2077654 | A | G/A |
| 2077663 | C | A/C |
| 2077669 | G | C/G |
| 2077671 | T | C/T |
| 2077682 | C | G/C |
| 2077688 | G | A/G |
| 2077691 | C | G/C |
| 2077694 | A | C/A |
| 2077697 | G | C/G |
| 2077703 | T | G/T |
| 2077715 | G | A/G |
| 2077724 | A | G/A |
| 2077726 | C | T/C |

| Position in SEQ ID 16053 | Nucleotide in SEQ ID 16053 | Mutated Nucleotide |
|---|---|---|
| 2077730 | G | C/G |
| 2077733 | G | A/G |
| 2077736 | C | C/T |
| 2077742 | G | C/G |
| 2077745 | A | G/A |
| 2077751 | G | A/G |
| 2077762 | T | C/T |
| 2077769 | T | C/T |
| 2077772 | A | G/A |
| 2077775 | G | A/G |
| 2077793 | G | C/G |
| 2077794 | A | G/A |
| 2077795 | C | T/C |
| 2077805 | C | T/C |
| 2080486 | C | T |
| 2086608 | G | A |
| 2096915 | G | A |
| 2098836 | C | T |
| 2099830 | G | A |
| 2126265 | C | T |
| 2131730 | G | A |
| 2135109 | C | T |
| 2136848 | C | T |
| 2144528 | G | A |
| 2147486 | G | A |
| 2154132 | C | T |
| 2154136 | C | T |
| 2188490 | C | T |
| 2191494 | C | T |
| 2199567 | G | A |
| 2208975 | G | A |
| 2212324 | G | A |
| 2212659 | G | A |
| 2230643 | G | A |
| 2235434 | G | A |
| 2250499 | C | T |
| 2259118 | C | T |
| 2260582 | G | A |
| 2266821 | C | T |
| 2271223 | G | A |
| 2273696 | C | T |
| 2277990 | C | T |
| 2291798 | C | T |
| 2293101 | C | C/T |
| 2293102 | G | G/T |
| 2293121 | G | G/C |
| 2293139 | A | A/C |
| 2293157 | G | G/A |
| 2293169 | G | G/C |
| 2293175 | G | G/A |
| 2293176 | A | A/T |
| 2293184 | C | C/G |
| 2293185 | G | G/A |
| 2293187 | A | A/G |
| 2293196 | G | A/G |
| 2293202 | G | G/C |
| 2293205 | G | C/G |
| 2293214 | G | G/C |
| 2293219 | A | A/T |
| 2293220 | G | G/C |
| 2293226 | G | C/G |
| 2293228 | G | G/A |
| 2293234 | A | A/T |
| 2293235 | G | G/C |
| 2293238 | G | G/C |
| 2293244 | G | G/C |
| 2293247 | G | A/G |
| 2293253 | G | A/G |
| 2293268 | G | C/G |
| 2293310 | G | G/A |
| 2293313 | G | G/C |
| 2293316 | G | G/A |
| 2293319 | G | G/A |
| 2293328 | G | G/C |
| 2293337 | G | G/C |
| 2293346 | G | G/C |
| 2293352 | C | C/G |
| 2293367 | G | G/C |
| 2293376 | C | C/G |
| 2293403 | C | C/G |
| 2293463 | C | C/G |
| 2302130 | G | A |
| 2312744 | C | T |
| 2313183 | G | A |
| 2315988 | C | T |
| 2323085 | C | T |
| 2329242 | C | T |
| 2332081 | G | A |
| 2341627 | C | T |
| 2347673 | C | T |
| 2348681 | G | A |
| 2359598 | G | A |
| 2362060 | A | G |
| 2368326 | G | A |
| 2376154 | G | A |
| 2380176 | C | T |
| 2382542 | C | T |
| 2382567 | C | T |
| 2382748 | C | T |
| 2389975 | C | T |
| 2392147 | C | T |
| 2396255 | G | A |
| 2415101 | G | A |
| 2422620 | C | T |
| 2437185 | G | A |
| 2448470 | G | A |
| 2452760 | G | A |
| 2456608 | C | T |
| 2459347 | C | T |
| 2459641 | G | A |
| 2460824 | C | T |
| 2463427 | C | T |
| 2482048 | C | T |
| 2482381 | G | A |
| 2483453 | C | T |
| 2487377 | G | A |
| 2489641 | G | A |
| 2492054 | G | A |
| 2502775 | G | A |
| 2515457 | G | A |
| 2518872 | G | A |
| 2530466 | G | A |
| 2532233 | G | A |
| 2533237 | G | A |
| 2536306 | G | A |
| 2538874 | G | A |
| 2542087 | G | A |
| 2544720 | C | T |
| 2553277 | G | A |
| 2556662 | C | T |
| 2559280 | G | A |
| 2562212 | G | A |
| 2564253 | G | A |
| 2564620 | G | A |
| 2566353 | G | A |
| 2572994 | G | A |
| 2573153 | C | T |
| 2575327 | G | A |
| 2599645 | G | A |
| 2599894 | G | A |
| 2601319 | G | A |
| 2606340 | G | A |
| 2608948 | G | A |
| 2610422 | C | T |
| 2614778 | G | A |
| 2617082 | G | A |
| 2618776 | C | T |
| 2618805 | C | T |
| 2620558 | G | A |
| 2626414 | A | G |
| 2636037 | C | T |
| 2639682 | G | A |

| Position in SEQ ID 16053 | Nucleotide in SEQ ID 16053 | Mutated Nucleotide |
|---|---|---|
| 2642753 | G | A |
| 2644984 | C | T |
| 2651718 | C | T |
| 2652733 | C | T |
| 2653074 | C | T |
| 2653159 | C | T |
| 2653337 | G | A |
| 2655271 | C | T |
| 2655308 | C | T |
| 2657059 | C | T |
| 2658261 | G | A |
| 2659295 | C | T |
| 2663775 | C | T |
| 2670944 | C | T |
| 2671043 | C | T |
| 2672551 | C | T |
| 2676880 | C | T |
| 2677056 | G | A |
| 2677196 | C | T |
| 2678066 | G | A |
| 2679900 | C | T |
| 2686364 | C | T |
| 2687028 | C | T |
| 2688632 | C | T |
| 2694405 | G | A |
| 2701281 | G | A |
| 2712327 | G | A |
| 2720850 | C | T |
| 2728435 | G | A |
| 2731397 | G | A |
| 2735550 | G | G/A |
| 2735576 | G | G/C |
| 2738768 | C | T |
| 2744600 | C | T |
| 2748694 | C | T |
| 2756873 | C | T |
| 2760595 | G | A |
| 2762887 | G | A |
| 2763137 | G | A |
| 2764279 | C | T |
| 2766645 | C | T |
| 2770562 | C | T |
| 2773173 | C | T |
| 2774095 | G | A |
| 2774734 | G | A |
| 2774874 | G | A |
| 2776314 | C | T |
| 2776919 | C | T |
| 2778598 | G | A |
| 2779539 | G | A |
| 2782696 | C | T |
| 2783578 | C | T |
| 2783738 | C | T |
| 2785372 | C | T |
| 2785531 | C | T |
| 2787379 | G | A |
| 2788015 | C | T |
| 2788247 | C | T |
| 2789216 | C | T |
| 2790626 | C | T |
| 2791577 | C | T |
| 2792510 | C | T |
| 2792715 | G | A |
| 2797814 | C | T |
| 2799953 | C | T |
| 2800033 | C | T |
| 2802765 | C | T |
| 2803789 | C | T |
| 2804694 | C | T |
| 2806670 | C | T |
| 2814611 | G | A |
| 2815199 | C | C/T |
| 2816239 | G | A |
| 2821693 | G | A |
| 2838356 | C | T |
| 2841171 | T | T/A |
| 2841177 | C | C/G |
| 2841183 | C | C/G |
| 2841213 | T | T/C |
| 2841228 | C | C/G |
| 2841237 | G | G/C |
| 2841251 | G | G/T |
| 2841255 | C | C/A |
| 2841258 | G | G/T |
| 2841276 | C | C/G |
| 2841293 | C | C/G |
| 2841297 | C | C/A |
| 2841303 | C | C/T |
| 2841306 | G | G/A |
| 2841312 | T | C/T |
| 2841315 | C | G/C |
| 2841322 | A | A/T |
| 2841323 | G | G/T |
| 2841327 | C | G/C |
| 2841335 | G | C/G |
| 2841357 | G | C/G |
| 2841360 | G | C/G |
| 2841369 | G | C/G |
| 2841376 | T | T/C |
| 2841377 | G | T/G |
| 2841384 | G | C/G |
| 2841389 | T | T/C |
| 2841397 | G | G/T |
| 2841398 | A | C/A |
| 2841402 | G | A/G |
| 2841403 | G | C/G |
| 2841409 | T | A/T |
| 2841413 | G | T/G |
| 2841423 | C | G/C |
| 2841444 | G | C/G |
| 2841451 | C | T/C |
| 2841477 | C | G/C |
| 2841514 | G | T/G |
| 2841531 | A | G/A |
| 2841534 | G | C/G |
| 2841536 | T | A/T |
| 2841540 | C | G/G |
| 2841546 | G | C/G |
| 2841552 | G | C |
| 2841554 | T | C/T |
| 2841555 | C | T/C |
| 2841562 | C | T/C |
| 2841563 | A | C/A |
| 2841569 | A | C/A/T |
| 2841575 | C | T/C |
| 2841585 | C | C/G |
| 2841588 | G | C/G |
| 2841594 | G | A/G |
| 2841605 | C | C/A |
| 2841609 | C | C/G |
| 2841617 | T | G/T |
| 2841636 | G | C/G |
| 2841656 | A | C/A |
| 2841660 | G | C/G |
| 2841668 | C | T/C |
| 2841690 | G | C/G |
| 2841700 | G | T |
| 2841701 | C | T |
| 2841708 | G | A/G |
| 2841734 | T | C |
| 2841735 | C | T |
| 2841738 | G | C |
| 2841744 | C | G/C |
| 2841747 | G | A |
| 2841756 | C | G |
| 2841759 | G | C |
| 2841762 | C | G |
| 2841776 | G | T |
| 2841778 | T | G |
| 2841783 | G | C |
| 2841786 | A | T |
| 2841789 | C | T |

| Position in SEQ ID 16053 | Nucleotide in SEQ ID 16053 | Mutated Nucleotide |
|---|---|---|
| 2845157 | G | A |
| 2850318 | G | A |
| 2851372 | G | A |
| 2853353 | C | T |
| 2853817 | G | A |
| 2868405 | C | T |
| 2874011 | C | T |
| 2875055 | G | A |
| 2875488 | G | A |
| 2876911 | G | T |
| 2882407 | C | T |
| 2888545 | C | T |
| 2890510 | C | T |
| 2892791 | G | A |
| 2896239 | G | A |
| 2896828 | G | A |
| 2896833 | G | A |
| 2899845 | C | T |
| 2899865 | C | T |
| 2901123 | C | T |
| 2905469 | C | T |
| 2912026 | G | A |
| 2921100 | C | T |
| 2934976 | G | A |
| 2935134 | G | A |
| 2935223 | G | A |
| 2945715 | G | A |
| 2953167 | C | T |
| 2956464 | C | T |
| 2965167 | G | A |
| 2971031 | C | T |
| 2971761 | C | T |
| 2973653 | C | T |
| 2976296 | C | T |
| 2978371 | C | T |
| 2983351 | G | A |
| 2986416 | C | T |
| 2987675 | C | T |
| 2988967 | C | T |
| 2992035 | C | T |
| 2993614 | A | G |
| 2994097 | G | A |
| 3000921 | G | A |
| 3002748 | G | A |
| 3003382 | G | A |
| 3005352 | G | A |
| 3006201 | C | T |
| 3021497 | G | A |
| 3026718 | C | T |
| 3027132 | G | A |
| 3031683 | C | T |
| 3032969 | C | T |
| 3044082 | G | A |
| 3045579 | G | A |
| 3049857 | G | A |
| 3066905 | C | T |
| 3079916 | T | A/T |
| 3079923 | C | C/T |
| 3079936 | G | A/G |
| 3079950 | A | T/A |
| 3080004 | C | C/T |
| 3080006 | A | T/A |
| 3080035 | C | C/T |
| 3080043 | A | C/A |
| 3080063 | G | C/G |
| 3080084 | C | C/T |
| 3080087 | G | C/T/G |
| 3080098 | C | C/A |
| 3080128 | C | T/C |
| 3080136 | A | G/A |
| 3080160 | C | G/C |
| 3080161 | T | C/T |
| 3080163 | T | C/T |
| 3080183 | T | C/T |
| 3080192 | G | C/G |
| 3080204 | G | C/G |
| 3080237 | G | C/G |
| 3080288 | G | C/G |
| 3080294 | G | T/G |
| 3080316 | C | C/T |
| 3080321 | T | T/C |
| 3080325 | G | T/G |
| 3080326 | C | T/C |
| 3080355 | A | T/A |
| 3080356 | A | A/G |
| 3080357 | A | A/G |
| 3080359 | A | A/G |
| 3080372 | A | A/G |
| 3080375 | A | A/C |
| 3080382 | G | G/A |
| 3080391 | A | A/G |
| 3080393 | C | C/T |
| 3080394 | G | G/A |
| 3080402 | A | A/G |
| 3080406 | A | A/G |
| 3080418 | A | A/G |
| 3080447 | C | C/T |
| 3080465 | T | T/C |
| 3080472 | C | C/T |
| 3080482 | A | A/G |
| 3080485 | C | C/T |
| 3080496 | T | T/C |
| 3082062 | G | A |
| 3084014 | G | A |
| 3087970 | C | T |
| 3089578 | G | A |
| 3090231 | G | G/C |
| 3101153 | G | A |
| 3120006 | C | T |
| 3121040 | C | T |
| 3125035 | C | T |
| 3125407 | C | T |
| 3128098 | C | T |
| 3131738 | C | T |
| 3133651 | C | T |
| 3133766 | G | A |
| 3137673 | C | T |
| 3138173 | G | T |
| 3147694 | C | T |
| 3148142 | C | T |
| 3148342 | C | T |
| 3148452 | C | T |
| 3148777 | C | T |
| 3148960 | C | T |
| 3149335 | C | T |
| 3151547 | C | T |
| 3152279 | C | T |
| 3153365 | G | A |
| 3156844 | C | T |
| 3175067 | G | A |
| 3176311 | C | T |
| 3180510 | C | T |
| 3181134 | C | T |
| 3196810 | C | T |
| 3198674 | G | A |
| 3203788 | G | A |
| 3204764 | G | T |
| 3208464 | G | T |
| 3213080 | C | T |
| 3214059 | C | T |
| 3216019 | C | T |
| 3216133 | C | T |
| 3218109 | C | T |
| 3226281 | C | T |
| 3229241 | G | A |
| 3230387 | G | A |
| 3235932 | C | T |
| 3237109 | C | T |
| 3238700 | C | T |
| 3241279 | C | T |
| 3241643 | G | A |
| 3245145 | C | T |

| Position in SEQ ID 16053 | Nucleotide in SEQ ID 16053 | Mutated Nucleotide |
|---|---|---|
| 3247705 | G | A |
| 3248186 | G | A |
| 3249319 | C | T |
| 3251559 | G | A |
| 3253347 | C | T |
| 3253453 | C | T |
| 3253884 | G | A |
| 3254464 | G | A |
| 3258028 | G | A |
| 3258094 | G | A |
| 3258637 | C | T |
| 3259667 | C | T |
| 3261792 | G | A |
| 3262978 | C | T |
| 3266668 | G | A |
| 3266806 | C | T |
| 3267341 | G | A |
| 3267927 | C | T |
| 3268140 | T | C |
| 3269676 | G | A |
| 3270548 | G | A |
| 3275254 | A | G |
| 3276870 | C | T |
| 3277187 | C | T |
| 3279932 | C | T |
| 3285105 | C | T |
| 3289175 | C | T |
| 3289533 | C | T |
| 3290417 | G | A |
| 3290880 | C | T |
| 3291408 | C | T |
| 3294618 | C | T |
| 3295292 | C | T |
| 3296150 | C | T |
| 3296689 | C | T |
| 3297254 | C | T |
| 3297593 | G | A |
| 3297802 | C | T |
| 3297816 | G | A |
| 3299219 | C | T |
| 3300457 | C | T |
| 3300838 | C | T |
| 3300849 | C | T |
| 3307410 | G | A |
| 3307738 | G | A |
| 3309205 | C | T |
| 3309441 | G | A |
| 3313410 | C | T |
| 3314734 | C | T |
| 3315483 | C | T |
| 3316995 | C | T |
| 3318906 | C | T |
| 3319964 | C | T |
| 3321895 | G | A |
| 3326784 | G | A |
| 3327191 | G | A |
| 3328753 | C | T |
| 3336319 | C | T |
| 3337206 | G | A |
| 3338688 | C | T |
| 3345311 | C | T |
| 3346757 | G | A |
| 3347355 | C | T |
| 3347540 | C | T |
| 3347560 | C | T |
| 3348860 | C | T |
| 3349015 | C | T |
| 3349651 | C | T |
| 3350820 | C | T |
| 3351613 | C | T |
| 3353030 | C | T |
| 3354271 | C | T |
| 3354637 | C | T |
| 3358411 | G | G/A |
| 3358883 | G | A |
| 3361525 | G | A |
| 3363657 | C | T |
| 3368167 | C | T |
| 3368381 | C | C/T |
| 3375301 | C | T |
| 3381507 | C | T |
| 3383846 | C | T |
| 3386322 | C | T |
| 3386914 | G | A |
| 3388650 | C | T |
| 3388663 | C | T |
| 3388840 | G | A |
| 3390202 | G | A |
| 3391187 | C | T |
| 3394129 | C | T |
| 3395838 | C | T |
| 3396692 | C | T |
| 3397717 | C | T |
| 3400152 | C | T |
| 3402866 | G | A |
| 3403044 | C | T |
| 3403253 | C | T |
| 3404959 | C | T |
| 3405078 | C | T |
| 3409620 | G | A |
| 3412544 | G | A |
| 3415574 | A | G |
| 3418558 | C | T |
| 3418906 | G | A |
| 3420004 | C | T |
| 3420345 | C | T |
| 3429994 | C | T |
| 3430020 | G | A |
| 3431269 | C | T |
| 3432683 | G | A |
| 3433788 | G | A |
| 3434662 | C | T |
| 3435439 | G | A |
| 3435661 | G | A |
| 3440357 | G | A |
| 3441404 | C | T |
| 3453288 | C | T |
| 3454769 | G | A |
| 3456480 | C | T |
| 3457161 | C | T |
| 3461043 | C | T |
| 3461116 | G | A |
| 3464902 | C | T |
| 3469479 | C | T |
| 3473066 | G | A |
| 3474749 | C | T |
| 3484337 | G | A |
| 3484696 | C | T |
| 3490633 | G | A |
| 3511395 | C | T |
| 3517523 | G | A |
| 3518338 | C | T |
| 3519210 | C | T |
| 3519280 | C | T |
| 3526212 | G | A |
| 3526229 | G | A |
| 3532172 | C | T |
| 3532281 | C | T |
| 3539856 | C | T |
| 3540438 | C | T |
| 3540952 | C | T |
| 3553678 | G | A |
| 3558780 | G | A |
| 3559503 | G | A |
| 3560298 | T | C |
| 3572036 | C | T |
| 3587529 | C | T |
| 3590513 | C | T |
| 3590937 | C | T |
| 3596971 | C | T |
| 3601304 | C | T |
| 3610733 | G | A |

-continued

| Position in SEQ ID 16053 | Nucleotide in SEQ ID 16053 | Mutated Nucleotide |
|---|---|---|
| 3613460 | C | T |
| 3617806 | G | A |
| 3618063 | C | T |
| 3618082 | G | A |
| 3621113 | G | A |
| 3625554 | C | T |
| 3626449 | C | T |
| 3626548 | C | T |
| 3627377 | C | T |
| 3627686 | C | T |
| 3628977 | C | T |
| 3632788 | C | T |
| 3647003 | C | T |
| 3650159 | G | A |
| 3658514 | C | T |
| 3659174 | C | T |
| 3672218 | G | A |
| 3695232 | G | A |
| 3702963 | C | T |
| 3704185 | C | T |
| 3704278 | G | G/C |
| 3704281 | T | T/G |
| 3704282 | C | C/T |
| 3704293 | T | T/G |
| 3704327 | G | A/G |
| 3704335 | C | T/C |
| 3704338 | C | G/C |
| 3704340 | A | C/A |
| 3704371 | G | C/G |
| 3704386 | T | C/T |
| 3704389 | C | G/C |
| 3704395 | G | C/G |
| 3704404 | G | C/G |
| 3704415 | C | T/C |
| 3704427 | G | A/G |
| 3704428 | C | T/C |
| 3704464 | C | T/C |
| 3704484 | A | C/A |
| 3704485 | C | G/C |
| 3704491 | G | C/G |
| 3704512 | G | C/G |
| 3704519 | A | G/A |
| 3704531 | A | GA |
| 3704534 | G | C/G |
| 3704536 | C | G/C |
| 3704543 | C | G/C |
| 3704544 | T | C/T |
| 3704554 | T | T/G |
| 3704563 | C | G/C |
| 3704573 | A | GA |
| 3704574 | A | G/A |
| 3704577 | G | C/G |
| 3704584 | C | G/C |
| 3704587 | G | A/G |
| 3704590 | G | C/G |
| 3704605 | T | C/T |
| 3704608 | C | G/C |
| 3704617 | T | G/T |
| 3704619 | A | C/A |
| 3704620 | C | A/C |
| 3704629 | C | G/C |
| 3704638 | C | G/C |
| 3704641 | G | C/G |
| 3704647 | C | G/C |
| 3704650 | G | C/A |
| 3704660 | C | A/C |
| 3704662 | G | A/G |
| 3704668 | T | C/T |
| 3704669 | G | A/G |
| 3704670 | T | C/T |
| 3704680 | C | G/C |
| 3704684 | C | G/C |
| 3704686 | G | C/G |
| 3704746 | G | C/G |
| 3704755 | C | C/G |
| 3704767 | A | A/G |

-continued

| Position in SEQ ID 16053 | Nucleotide in SEQ ID 16053 | Mutated Nucleotide |
|---|---|---|
| 3704782 | T | T/C |
| 3704789 | A | VG |
| 3704791 | C | C/G |
| 3704806 | C | C/T |
| 3704815 | T | T/C |
| 3704822 | C | C/G |
| 3704844 | C | C/A |
| 3704851 | A | A/G |
| 3704852 | C | C/A |
| 3704866 | T | T/C |
| 3704869 | C | C/G |
| 3704875 | C | C/G |
| 3704906 | G | A |
| 3706589 | C | C/G |
| 3706625 | G | G/C |
| 3706641 | G | G/T |
| 3706652 | G | G/A |
| 3706655 | C | C/G |
| 3706679 | T | T/C |
| 3706715 | C | C/G |
| 3706735 | C | C/G |
| 3706737 | A | A/G |
| 3706739 | G | G/C |
| 3706784 | C | C/T |
| 3706790 | T | T/C |
| 3706794 | A | A/G |
| 3706805 | G | G/C |
| 3706822 | A | A/G |
| 3706862 | C | C/G |
| 3706926 | G | G/T |
| 3706932 | A | A/C |
| 3706940 | G | G/A |
| 3706945 | G | G/C |
| 3706950 | T | T/A |
| 3706951 | C | C/G |
| 3706958 | T | T/C |
| 3706960 | A | A/G |
| 3706967 | C | C/G |
| 3706983 | C | C/G |
| 3706985 | G | G/C |
| 3706994 | G | G/C |
| 3706996 | A | A/C |
| 3707006 | G | G/C |
| 3707012 | C | C/A |
| 3707013 | A | A/G |
| 3707036 | C | C/G |
| 3711369 | G | A |
| 3713575 | C | T |
| 3724878 | G | A |
| 3724955 | G | A |
| 3727102 | G | A |
| 3727130 | G | A |
| 3727909 | C | T |
| 3732046 | C | T |
| 3733052 | G | A |
| 3740023 | G | A |
| 3741710 | G | A |
| 3744813 | G | A |
| 3750360 | G | A |
| 3756113 | C | T |
| 3762328 | G | A |
| 3763755 | G | A |
| 3764788 | G | A |
| 3771690 | C | T |
| 3775098 | G | A |
| 3775718 | G | A |
| 3776484 | G | A |
| 3783703 | T | C |
| 3786947 | G | A |
| 3788243 | C | T |
| 3798429 | G | A |
| 3799202 | G | A |
| 3799222 | G | A |
| 3802171 | C | T |
| 3806580 | C | T |
| 3825163 | C | T |

| Position in SEQ ID 16053 | Nucleotide in SEQ ID 16053 | Mutated Nucleotide |
|---|---|---|
| 3828141 | G | A |
| 3831054 | G | A |
| 3831114 | G | A |
| 3831589 | C | T |
| 3831701 | G | A |
| 3837175 | G | A |
| 3841387 | G | A |
| 3843222 | C | T |
| 3843509 | G | A |
| 3843815 | G | A |
| 3844238 | G | A |
| 3846121 | G | A |
| 3846452 | G | A |
| 3852914 | T | C |
| 3873931 | G | A |
| 3879758 | G | A |
| 3883035 | C | T |
| 3905636 | C | T |
| 3919216 | C | T |
| 3920191 | G | A |
| 3928659 | C | T |
| 3935704 | C | C/T |
| 3941486 | G | A |
| 3964297 | G | A |
| 3965972 | G | A |
| 3968608 | C | T |
| 3983198 | C | T |
| 3993744 | G | G/A |
| 4002370 | G | A |
| 4004770 | C | T |
| 4006580 | C | T |
| 4006932 | G | A |
| 4013932 | G | A |
| 4014337 | T | C |
| 4017638 | C | T |
| 4019106 | G | A |
| 4020770 | C | T |
| 4025302 | C | T |
| 4027304 | G | A |
| 4034139 | G | G/T |
| 4043320 | A | G |
| 4063459 | G | A |
| 4072648 | C | T |
| 4073198 | C | T |
| 4073446 | G | A |
| 4074524 | C | T |
| 4081747 | C | T |
| 4086210 | A | G |
| 4089001 | C | T |
| 4102977 | C | T |
| 4104004 | C | T |
| 4114649 | G | A |
| 4117981 | G | A |
| 4118234 | C | T |
| 4121337 | G | A |
| 4124406 | G | A |
| 4130087 | C | T |
| 4148633 | C | T |
| 4150599 | C | T |
| 4152842 | C | T |
| 4156366 | G | A |
| 4156524 | G | A |
| 4157742 | Ci | A |
| 4157795 | Ci | A |
| 4158022 | G | A |
| 4160265 | G | A |
| 4170648 | C | T |
| 4186914 | C | T |
| 4187188 | G | A |
| 4192330 | C | T |
| 4192395 | C | T |
| 4194086 | C | T |
| 4196729 | C | T |
| 4205330 | C | T |
| 4218066 | G | A |
| 4220842 | G | A |
| 4231722 | C | T |
| 4251577 | C | T |
| 4253562 | G | A |
| 4255089 | G | A |
| 4268915 | C | T |
| 4284264 | C | T |
| 4285070 | G | A |
| 4286615 | G | A |
| 4299670 | C | T |
| 4302785 | G | A |
| 4302812 | C | T |
| 4312528 | G | A |
| 4312875 | C | T |
| 4314885 | G | A |
| 4314896 | C | T |
| 4314899 | G | A |
| 4316350 | C | T |
| 4318874 | C | T |
| 4319625 | C | T |
| 4324089 | G | A |
| 4325174 | G | A |
| 4325955 | G | A |
| 4327176 | C | T |
| 4328372 | C | T |
| 4329685 | C | T |
| 4329867 | C | T |
| 4331851 | C | T |
| 4331916 | C | T |
| 4334253 | C | T |
| 4335755 | C | T |
| 4340706 | C | T |
| 4343282 | T | C |
| 4347901 | C | T |
| 4352755 | G | A |
| 4360959 | G | A |
| 4361293 | C | T |
| 4362371 | C | T |
| 4365880 | G | A |
| 4376161 | C | T |
| 4376238 | C | T |
| 4378853 | G | A |
| 4395837 | G | A |
| 4396016 | C | T |
| 4402736 | C | T |
| 4406151 | G | A |
| 4414580 | G | A |
| 4414632 | C | T |
| 4420655 | C | T |
| 4433146 | G | A |
| 4438071 | G | A |
| 4440571 | T | C |
| 4440772 | G | A |
| 4443633 | G | A |
| 4444731 | C | T |
| 4446487 | T | C |
| 4463567 | C | T |
| 4463766 | G | A |
| 4467838 | G | A |
| 4474494 | G | A |
| 4481185 | G | A |
| 4486135 | C | T |
| 4487769 | G | A |
| 4490385 | G | A |
| 4496083 | G | A |
| 4499876 | C | T |
| 4503563 | C | T |
| 4504062 | C | T |
| 4517204 | G | A |
| 4524639 | G | A |
| 4524706 | G | A |
| 4529241 | G | A |
| 4529778 | G | A |
| 4531772 | G | A |
| 4532547 | G | A |
| 4532943 | G | A |
| 4533824 | G | A |

| Position in SEQ ID 16053 | Nucleotide in SEQ ID 16053 | Mutated Nucleotide |
|---|---|---|
| 4535251 | G | A |
| 4537480 | G | A |
| 4537859 | G | A |
| 4543587 | G | A |
| 4547764 | C | T |
| 4558815 | C | T |
| 4558914 | C | T |
| 4564648 | G | A |
| 4564991 | G | A |
| 4573497 | C | T |
| 4573536 | C | T |
| 4575408 | C | T |
| 4577334 | C | T |
| 4580403 | G | A |
| 4582642 | T | C |
| 4588387 | C | A |
| 4588663 | G | A |
| 4597434 | C | T |
| 4598262 | C | T |
| 4601247 | G | G/C |
| 4601248 | T | T/C |
| 4603166 | C | T |
| 4611131 | C | T |
| 4614475 | C | T |
| 4616665 | G | A |
| 4617801 | G | A |
| 4619989 | C | T |
| 4621439 | G | A |
| 4626601 | G | A |
| 4630752 | C | T |
| 4649811 | A | A/G |
| 4650590 | C | T |
| 4669551 | C | T |
| 4670815 | G | A |
| 4674426 | G | A |
| 4677968 | C | T |
| 4688341 | C | T |
| 4697092 | C | T |
| 4700003 | G | A |
| 4702254 | C | T |
| 4704691 | C | T |
| 4704704 | C | T |
| 4713174 | C | T |
| 4727776 | G | A |
| 4736024 | C | T |
| 4766839 | C | T |
| 4769655 | C | T |
| 4776927 | G | A |
| 4788381 | C | T |
| 4794373 | C | T |
| 4799012 | G | A |
| 4812357 | C | T |
| 4813704 | G | G/T |
| 4813710 | G | G/T |
| 4813711 | A | A/C |
| 4814060 | C | C/T |
| 4814078 | C | C/T |
| 4814081 | C | C/T |
| 4814082 | G | G/C |
| 4814087 | T | T/C |
| 4818340 | G | A |
| 4820651 | C | T |
| 4821863 | G | A |
| 4852073 | T | T/C |
| 4852080 | T | C/T |
| 4852093 | T | C/T |
| 4852131 | G | A/G |
| 4852238 | T | C/T |
| 4857271 | T | T/C |
| 4852348 | G | G/A |
| 4852373 | T | T/C |
| 4858842 | C | T |
| 4859921 | G | A |
| 4860949 | G | A |
| 4872907 | G | A |
| 4879205 | C | T |
| 4886810 | C | T |
| 4889101 | G | A |
| 4891956 | C | T |
| 4896797 | C | T |
| 4903124 | G | A |
| 4904325 | A | A/G |
| 4904344 | C | C/G |
| 4904345 | C | C/T |
| 4904355 | A | G |
| 4904359 | G | G/C |
| 4904360 | T | T/C |
| 4908341 | C | T |
| 4908687 | C | T |
| 4911304 | C | T |
| 4916472 | C | T |
| 4920831 | C | T |
| 4924034 | C | T |
| 4924484 | C | T |
| 4927068 | C | T |
| 4927798 | C | T |
| 4929941 | C | T |
| 4930693 | C | T |
| 4932671 | C | T |
| 4933447 | T | T/C |
| 4948234 | G | A |
| 4950870 | C | T |
| 4951932 | C | T |
| 4953821 | C | T |
| 4978515 | G | A |
| 4981742 | C | T |
| 4984320 | A | G |
| 4987021 | G | A |
| 4987606 | G | A |
| 4991441 | G | A |
| 4992870 | G | A |
| 5014441 | C | T |
| 5016187 | C | T |
| 5016773 | C | T |
| 5025119 | G | A |
| 5030757 | C | T |
| 5053257 | C | T |
| 5056010 | C | T |
| 5056241 | C | T |
| 5058845 | C | T |
| 5058850 | C | T |
| 5060436 | C | T |
| 5061245 | C | T |
| 5062621 | C | T |
| 5063656 | C | T |
| 5063753 | A | A/G |
| 5063759 | T | T/G |
| 5063766 | C | C/T |
| 5063772 | A | A/G |
| 5063775 | T | T/C |
| 5063777 | A | A/G |
| 5063883 | T | T/C |
| 5063900 | G | G/A |
| 5063967 | T | C/T |
| 5063994 | C | C/G |
| 5063997 | T | C/T |
| 5064000 | G | C/G |
| 5064054 | C | C/G |
| 5064140 | T | A/T |
| 5064188 | G | G/C |
| 5064199 | G | A/G |
| 5064223 | T | C/T |
| 5064318 | G | G/A |
| 5064363 | G | G/A |
| 5064364 | C | C/G |
| 5064368 | T | C/T |
| 5066806 | C | T |
| 5079654 | C | T |
| 5080712 | C | T |
| 5080760 | G | A |
| 5083716 | C | T |
| 5085149 | C | T |

| Position in SEQ ID 16053 | Nucleotide in SEQ ID 16053 | Mutated Nucleotide | Position in SEQ ID 16053 | Nucleotide in SEQ ID 16053 | Mutated Nucleotide |
|---|---|---|---|---|---|
| 5087053 | C | T | 5530664 | C | T |
| 5089288 | G | A | 5537010 | G | A |
| 5095356 | C | T | 5540526 | G | A |
| 5096131 | C | T | 5541233 | C | T |
| 5099106 | C | T | 5543634 | C | T |
| 5099331 | C | T | 5545010 | C | T |
| 5099501 | C | T | 5545574 | G | A |
| 5104316 | C | T | 5548499 | C | T |
| 5104896 | C | T | 5557711 | G | A |
| 5105840 | C | T | 5574966 | C | T |
| 5107273 | C | T | 5576016 | C | T |
| 5107438 | G | A | 5579654 | C | T |
| 5110964 | G | A | 5582215 | C | C/T |
| 5111341 | G | A | 5590781 | T | T/A |
| 5111525 | G | A | 5590796 | C | C/T |
| 5113971 | C | T | 5590809 | T | T/C |
| 5114926 | C | T/C | 5590810 | G | G/A |
| 5114933 | C | T/C | 5590823 | G | G/A |
| 5116995 | G | A | 5590828 | A | A/G |
| 5117622 | G | A | 5590847 | G | G/T |
| 5126463 | G | A | 5590861 | G | G/C |
| 5128522 | G | A | 5590867 | A | A/C |
| 5131328 | G | A | 5590868 | A | A/G |
| 5132598 | C | T | 5590886 | G | A/G |
| 5133033 | C | T | 5590889 | T | C/T |
| 5134996 | G | A | 5590903 | A | G/A |
| 5136119 | C | T | 5590909 | G | T/G |
| 5139533 | C | T | 5590910 | C | G/C |
| 5141709 | G | A | 5590912 | G | T/G |
| 5147647 | C | T | 5590918 | G | A/G |
| 5158997 | C | T | 5590923 | A | G/A |
| 5171223 | G | A | 5590927 | T | G/T |
| 5189948 | C | T | 5590933 | G | A/G |
| 5196838 | C | T | 5590945 | C | G/C |
| 5203530 | G | A | 5590960 | T | C/T |
| 5204859 | C | T | 5590961 | C | T/C |
| 5213315 | G | A | 5590972 | T | C/T |
| 5216015 | G | A | 5590978 | T | C/T |
| 5221083 | C | T | 5590981 | G | C/G |
| 5229965 | G | A | 5590987 | T | C/T |
| 5233924 | G | A | 5590993 | C | G/C |
| 5246591 | G | A | 5591002 | G | G/A |
| 5247914 | C | T | 5591008 | T | C/T |
| 5253451 | C | T | 5591026 | C | G/C |
| 5255901 | C | T | 5591035 | C | G/C |
| 5259871 | G | A | 5591054 | C | A/C |
| 5270798 | G | A | 5591063 | T | C/T |
| 5277822 | G | A | 5591065 | C | G/C |
| 5280936 | C | T | 5591069 | A | A/G |
| 5283902 | G | A | 5591074 | A | G/A |
| 5292603 | C | T | 5591077 | C | A/C |
| 5309793 | G | A | 5591092 | A | G/A |
| 5317263 | G | A | 5591095 | G | C/G |
| 5323245 | G | A | 5591098 | T | C/T |
| 5323289 | C | T | 5591115 | G | A/G |
| 5323708 | G | A | 5591158 | G | T/G |
| 5326705 | G | A | 5591179 | G | T/G |
| 5339380 | G | A | 5591220 | C | G/C |
| 5349635 | C | T | 5591226 | A | G/A |
| 5350111 | G | A | 5591268 | T | C/T |
| 5356868 | C | T | 5591361 | C | G/C |
| 5363828 | C | T | 5591442 | G | A/G |
| 5385564 | C | T | 5591445 | C | T/C |
| 5391456 | G | A | 5591457 | G | C/G |
| 5404805 | G | A | 5591458 | A | C/A |
| 5415953 | G | A | 5591466 | G | C/G |
| 5416207 | C | T | 5591469 | G | A/G |
| 5419045 | C | T | 5591472 | C | G/C |
| 5438747 | G | A | 5591476 | A | A/G |
| 5457995 | G | A | 5591496 | G | C/G |
| 5465469 | C | T | 5591499 | A | C/A |
| 5481386 | G | A | 5591505 | G | C/G |
| 5485106 | C | T | 5591508 | T | G/T |
| 5500846 | G | A | 5591520 | A | G/A |
| 5514802 | C | T | 5591532 | C | T/C |
| 5516464 | C | T | 5591541 | C | T/C |

-continued

| Position in SEQ ID 16053 | Nucleotide in SEQ ID 16053 | Mutated Nucleotide |
|---|---|---|
| 5591553 | G | A/G |
| 5591562 | G | T/G |
| 5591565 | G | C/G |
| 5591571 | A | G/A |
| 5591577 | A | C/A |
| 5591596 | C | T/C |
| 5591598 | G | C/G |
| 5591607 | C | T/C |
| 5591613 | T | C/T |
| 5591632 | C | A/C |
| 5591635 | G | G/T |
| 5591640 | T | T/C |
| 5591643 | C | C/T |
| 5591654 | A | A/C |
| 5591656 | A | A/G |
| 5604643 | G | A |
| 5612009 | C | T |
| 5626626 | C | T |
| 5629121 | C | T |
| 5631426 | C | T |
| 5636810 | G | A |
| 5657449 | C | T |
| 5659036 | G | A |
| 5692125 | C | T |
| 5694507 | C | T |
| 5696833 | C | T |
| 5698190 | C | T |
| 5705110 | C | T |
| 5708625 | C | T |
| 5709728 | C | T |
| 5724677 | C | T |
| 5727195 | C | T |
| 5728510 | C | T |
| 5732980 | C | T |
| 5738712 | G | A |
| 5738846 | C | T |
| 5745077 | C | T |
| 5751489 | C | T |
| 5751716 | C | T |
| 5753910 | C | T |
| 5755351 | C | T |
| 5756752 | C | T |
| 5756803 | C | T |
| 5760058 | C | G |
| 5760301 | C | T |
| 5763377 | C | T |
| 5764363 | C | T |
| 5765100 | C | T |
| 5765446 | C | T |
| 5767623 | C | T |
| 5779664 | C | T |
| 5780052 | C | T |
| 5781808 | C | T |
| 5783477 | G | A |
| 5788208 | C | T |
| 5790337 | C | T |
| 5791404 | C | T |
| 5793414 | G | A |
| 5795059 | C | T |
| 5795465 | G | A |
| 5799803 | G | A |
| 5803395 | C | T |
| 5803716 | G | A |
| 5805398 | G | A |
| 5805735 | G | A |
| 5807160 | C | T |
| 5809295 | G | A |
| 5810587 | G | T |
| 5811908 | C | T |
| 5813504 | C | T |
| 5813556 | C | T |
| 5834083 | C | T |
| 5842153 | G | C |
| 5843698 | T | T/C |
| 5843724 | C | C/A |
| 5843727 | C | C/T |

-continued

| Position in SEQ ID 16053 | Nucleotide in SEQ ID 16053 | Mutated Nucleotide |
|---|---|---|
| 5843751 | G | G/A |
| 5843752 | G | G/C |
| 5843766 | A | A/G |
| 5843783 | A | A/G |
| 5843786 | G | G/C |
| 5843787 | C | C/G |
| 5843795 | G | G/C |
| 5843796 | T | T/A |
| 5843797 | G | G/T |
| 5843804 | C | C/G |
| 5843810 | C | C/T |
| 5843818 | T | T/C |
| 5843819 | T | T/G |
| 5843831 | C | C/T |
| 5843863 | G | G/T |
| 5843878 | C | C/T |
| 5843881 | G | G/T |
| 5843888 | G | G/A |
| 5843890 | G | G/C |
| 5843897 | C | C/G |
| 5843899 | G | G/T |
| 5843902 | C | C/T |
| 5843942 | C | C/T |
| 5843965 | G | C/G |
| 5843980 | C | C/G |
| 5843981 | C | C/T |
| 5843987 | C | C/G |
| 5843988 | C | C/T |
| 5843992 | C | C/T |
| 5857131 | C | T |
| 5858663 | C | T |
| 5879695 | G | A |
| 5880188 | T | T/C |
| 5880203 | G | G/C |
| 5880223 | C | C/T |
| 5880241 | A | A/C |
| 5880306 | C | C/T |
| 5880307 | T | T/C |
| 5880349 | A | A/T |
| 5880412 | G | G/A |
| 5880421 | C | C/T |
| 5880430 | A | A/G |
| 5880517 | T | T/C |
| 5882826 | G | A |
| 5887657 | G | C/G |
| 5887660 | G | C/G |
| 5887684 | T | C/T |
| 5887693 | T | C/T |
| 5887696 | G | C/G |
| 5887718 | G | G/A |
| 5887732 | G | G/C |
| 5887734 | G | G/A |
| 5887765 | A | A/G/C |
| 5887771 | G | G/C |
| 5887774 | G | G/A |
| 5887775 | C | C/T |
| 5887784 | T | T/C |
| 5887792 | T | T/C |
| 5887810 | G | G/C |
| 5887813 | G | G/C |
| 5887816 | G | G/C |
| 5887820 | G | G/C |
| 5887824 | C | C/G |
| 5887831 | G | G/C |
| 5887837 | C | C/T |
| 5887843 | C | C/G |
| 5887892 | G | A/G |
| 5887931 | G | G/A/C |
| 5887937 | G | G/C |
| 5887938 | C | C/G |
| 5887942 | C | C/G |
| 5887945 | G | G/C |
| 5887951 | G | C/G |
| 5887960 | G | G/C |
| 5887969 | G | G/C |
| 5887970 | C | C/G |

| Position in SEQ ID 16053 | Nucleotide in SEQ ID 16053 | Mutated Nucleotide | Position in SEQ ID 16053 | Nucleotide in SEQ ID 16053 | Mutated Nucleotide |
|---|---|---|---|---|---|
| 5887971 | A | A/G | 5895115 | C | G/C |
| 5887974 | G | G/T | 5895118 | A | C/A |
| 5887975 | C | C/T | 5895127 | C | G/C |
| 5887977 | T | T/A | 5895130 | C | G/C |
| 5887982 | C | C/A/T | 5895137 | A | T/A |
| 5887988 | G | G/T | 5895142 | T | C/T |
| 5887990 | C | C/G | 5895147 | G | C/G |
| 5888003 | A | A/C | 5895181 | C | T/C |
| 5888004 | A | A/G | 5895254 | A | G/A |
| 5888005 | A | A/G | 5895280 | T | C/T |
| 5888026 | C | C/T | 5895283 | G | C/G |
| 5888050 | G | G/C | 5895298 | C | G/C |
| 5888053 | G | G/C | 5895299 | G | A/G |
| 5888056 | G | G/C | 5895319 | C | G/C |
| 5888083 | G | G/C | 5895328 | C | T/C |
| 5888092 | C | C/G | 5895334 | C | T/C |
| 5888095 | C | C/G | 5895340 | G | C/G |
| 5888102 | G | G/A | 5895346 | G | G/C |
| 5888103 | T | T/C | 5895349 | C | T/C |
| 5888122 | C | C/T | 5895358 | C | T/C |
| 5888143 | G | G/C | 5895361 | C | G/C |
| 5890782 | G | G/C | 5895370 | C | C/T |
| 5890839 | T | C/T | 5895391 | C | T/C |
| 5890849 | T | A/T | 5895436 | G | C/G |
| 5890851 | C | G/C | 5895437 | A | G/A |
| 5890863 | C | G/C | 5895439 | C | G/C |
| 5890864 | G | A/G | 5895493 | G | C/G |
| 5890869 | G | T/G | 5895496 | G | C/G |
| 5890872 | C | T/C | 5895505 | C | T/C |
| 5890893 | C | T/C | 5895529 | T | C/T |
| 5890899 | C | T/C | 5895532 | C | G/C |
| 5890906 | G | A/G | 5895577 | G | C/G |
| 5890908 | G | G/A | 5895580 | C | G/C |
| 5890914 | C | T/C | 5895628 | T | C/T/G |
| 5890920 | C | G/C | 5895629 | T | CT |
| 5890923 | C | T/C | 5895661 | C | C/G |
| 5890926 | C | G/C | 5895847 | C | C/G |
| 5890971 | C | C/T | 5895878 | G | G/A |
| 5890992 | C | C/T | 5895898 | C | C/T |
| 5891058 | G | C/G | 5895899 | A | A/C |
| 5891061 | G | C/G | 5895915 | A | G/A |
| 5891070 | C | T/C | 5895949 | C | T/C |
| 5891094 | T | C/T | 5896081 | C | G/C |
| 5891097 | C | C/G | 5896085 | C | T/C |
| 5891100 | C | C/T | 5896090 | C | T/C |
| 5891121 | C | T/C | 5896115 | C | C/T |
| 5891142 | G | G/C | 5896120 | A | A/G |
| 5891145 | C | C/G | 5896123 | G | G/C |
| 5891148 | G | C/G | 5896126 | T | T/C |
| 5891187 | G | G/C | 5896147 | T | T/G |
| 5891220 | G | G/C | 5896148 | T | T/C |
| 5891247 | T | T/C | 5896154 | T | T/C |
| 5891250 | C | C/T | 5896156 | G | G/C |
| 5891263 | T | T/C | 5896159 | G | G/C |
| 5892300 | C | C/T | 5896246 | T | T/C |
| 5892304 | A | A/C | 5896279 | C | T/C |
| 5892312 | C | C/G | 5896312 | A | A/G |
| 5892330 | C | C/T | 5896324 | A | A/G |
| 5892370 | A | A/G | 5896333 | G | G/A |
| 5892413 | C | C/T | 5896381 | G | G/C |
| 5892414 | T | T/C | 5900925 | C | C/G |
| 5892456 | A | A/T | 5900943 | G | G/T |
| 5892519 | G | G/A | 5900949 | C | C/A |
| 5894264 | G | A | 5900955 | C | C/T |
| 5894322 | G | A | 5900958 | C | C/G |
| 5894986 | A | A/G | 5900965 | T | T/C |
| 5894989 | T | T/C | 5900971 | G | G/C |
| 5895041 | G | G/A | 5900972 | C | C/G |
| 5895043 | C | C/G | 5900997 | C | C/T |
| 5895049 | C | C/G | 5901000 | C | C/T |
| 5895054 | T | T/C | 5901015 | A | A/C |
| 5895058 | G | G/C | 5901034 | C | C/A |
| 5895073 | C | C/G | 5901048 | C | C/T |
| 5895100 | G | G/C | 5901050 | G | GA |
| 5895106 | C | G/C | 5901057 | C | C/T |
| 5895108 | T | C/T | 5901068 | G | G/A |

| Position in SEQ ID 16053 | Nucleotide in SEQ ID 16053 | Mutated Nucleotide |
|---|---|---|
| 5901071 | A | A/G |
| 5901078 | G | G/T |
| 5901099 | C | C/T |
| 5901123 | T | T/A |
| 5901135 | G | C/G |
| 5901172 | G | A/G |
| 5901186 | G | G/A |
| 5901195 | T | T/C |
| 5901204 | G | G/A |
| 5901219 | C | A/C |
| 5901342 | T | C/T |
| 5901345 | T | T/G |
| 5901346 | T | T/C |
| 5901354 | C | C/G |
| 5901615 | C | T/C |
| 5901617 | G | C/G |
| 5901660 | C | C/G |
| 5901664 | T | T/G |
| 5901669 | C | A/C |
| 5901673 | T | A/T |
| 5901675 | C | G/C |
| 5901679 | C | C/T |
| 5901688 | C | T/C |
| 5901689 | T | A/T |
| 5901690 | G | C/G |
| 5901698 | C | A/C |
| 5901712 | G | A/G |
| 5901713 | T | A/T |
| 5901714 | T | T/C |
| 5901719 | G | G/C |
| 5901726 | G | G/C |
| 5901729 | C | C/G |
| 5901732 | C | C/T |
| 5901733 | G | G/A |
| 5901738 | C | C/G |
| 5901752 | C | C/T |
| 5901757 | G | G/A |
| 5901764 | T | C/T |
| 5901767 | C | G/C |
| 5901771 | G | C/G |
| 5901790 | C | G/C |
| 5901791 | G | C/G |
| 5901793 | G | A/G |
| 5901807 | G | C/G |
| 5901824 | G | A/G |
| 5901826 | G | GA |
| 5901830 | T | T/G |
| 5901840 | A | A/C |
| 5902914 | C | T |
| 5905708 | G | A |
| 5925008 | C | T |
| 5925517 | G | A |
| 5926357 | G | A |
| 5928875 | C | T |
| 5930205 | C | T |
| 5933164 | G | A |
| 5947433 | C | T |
| 5957471 | G | A |
| 5960825 | C | T |
| 5961809 | T | G/T |
| 5961866 | T | T/A |
| 5970914 | C | T |
| 5975910 | A | G/A |
| 5975911 | A | G/A |
| 5975926 | A | G/A |
| 5978267 | C | T |
| 6005749 | C | T |
| 6009383 | G | A |
| 6010024 | C | T |
| 6026234 | C | T |
| 6033950 | C | T |
| 6042035 | C | T |
| 6050103 | C | C/T |
| 6050112 | A | C/A |
| 6050115 | G | G/C |
| 6050116 | C | C/G |
| 6050118 | G | G/A |
| 6050509 | G | A/G |
| 6050536 | G | G/C |
| 6050556 | G | C/G |
| 6050557 | C | A/C |
| 6050584 | T | T/A |
| 6050694 | T | T/C |
| 6050727 | A | G/A |
| 6050730 | G | C/G |
| 6050769 | G | G/A |
| 6050820 | A | A/C |
| 6050822 | T | T/C |
| 6050824 | C | C/T |
| 6050947 | T | C/T |
| 6050949 | A | G/A |
| 6050952 | T | T/C |
| 6050958 | G | A/G |
| 6050965 | A | C/A |
| 6050971 | T | C/T |
| 6051079 | A | A/G |
| 6051571 | G | A |
| 6072579 | C | T |
| 6074412 | G | A |
| 6075058 | G | A |
| 6083188 | C | T |
| 6085177 | C | T |
| 6090298 | C | T |
| 6094419 | C | T |
| 6095825 | C | T |
| 6098808 | C | T |
| 6099142 | C | T |
| 6099801 | C | T |
| 6100131 | C | T |
| 6100928 | C | T |
| 6114598 | C | T |
| 6129757 | G | A |
| 6151020 | G | A |
| 6157309 | C | T |
| 6157376 | C | T |
| 6178150 | G | A |
| 6188180 | C | T |
| 6191683 | G | A |
| 6207945 | G | A |
| 6216366 | C | T |
| 6230439 | A | G |
| 6251389 | G | A |
| 6251652 | G | A |
| 6255100 | G | A |
| 6264179 | G | A |
| 6265855 | G | A |
| 6267856 | G | A |
| 6278700 | G | A |
| 6281103 | C | T |
| 6282875 | C | T |
| 6286620 | C | T |
| 6288364 | C | T |
| 6291716 | C | T |
| 6297821 | C | T |
| 6303632 | G | A |
| 6306219 | C | T |
| 6309112 | G | A |
| 6322894 | G | A |
| 6328731 | C | T |
| 6331035 | G | A |
| 6338677 | G | A |
| 6339429 | C | T |
| 6344180 | C | T |
| 6346415 | C | T |
| 6361477 | C | T |
| 6362282 | G | A |
| 6366940 | C | T |
| 6368217 | G | A |
| 6369699 | G | A |
| 6375315 | G | A |
| 6381431 | C | T |
| 6401947 | G | A |

| Position in SEQ ID 16053 | Nucleotide in SEQ ID 16053 | Mutated Nucleotide | Position in SEQ ID 16053 | Nucleotide in SEQ ID 16053 | Mutated Nucleotide |
|---|---|---|---|---|---|
| 6403645 | C | T | 6858684 | G | A |
| 6437676 | C | T | 6883984 | C | T |
| 6439389 | G | A | 6884717 | G | A |
| 6450624 | C | T | 6890659 | G | A |
| 6454248 | C | T | 6892977 | G | A |
| 6454843 | C | T | 6898871 | C | T |
| 6456678 | C | T | 6902839 | A | T |
| 6456912 | C | T | 6911746 | G | A |
| 6459047 | G | A | 6916561 | G | A |
| 6460584 | T | C | 6916943 | C | T |
| 6471884 | G | A | 6927456 | G | A |
| 6485358 | C | T | 6960103 | G | A |
| 6499172 | G | A | 6961070 | C | T |
| 6500551 | G | A | 6968534 | C | T |
| 6507389 | C | T | 6973392 | G | A |
| 6517707 | C | T | 6987945 | G | A |
| 6525706 | G | A | 6993597 | G | A |
| 6538378 | C | T | 6995391 | C | T |
| 6542765 | C | T | 6996621 | C | T |
| 6543445 | C | T | 6999127 | C | T |
| 6543579 | C | T | 6999520 | C | T |
| 6545779 | C | T | 6999817 | C | T |
| 6550507 | C | T | 7000264 | C | T |
| 6553219 | G | A | 7002458 | G | A |
| 6553546 | G | A | 7003486 | G | A |
| 6553589 | G | A | 7003496 | G | A |
| 6555594 | G | A | 7004068 | C | T |
| 6556192 | C | T | 7009952 | C | T |
| 6560301 | C | T | 7010119 | C | T |
| 6561416 | G | A | 7010712 | C | T |
| 6563658 | C | T | 7015917 | G | A |
| 6564054 | C | T | 7019067 | C | T |
| 6564511 | C | T | 7019437 | C | T |
| 6564827 | C | T | 7020227 | C | T |
| 6567102 | C | T | 7021026 | C | T |
| 6567313 | C | T | 7023202 | C | T |
| 6568360 | C | T | 7024113 | C | T |
| 6569524 | C | T | 7026584 | C | T |
| 6569696 | G | A | 7028273 | C | T |
| 6570943 | C | T | 7028622 | C | T |
| 6572188 | C | T | 7029812 | C | T |
| 6572441 | C | T | 7031076 | C | T |
| 6580904 | G | A | 7040546 | C | T |
| 6581219 | G | G/A | 7053643 | C | T |
| 6589934 | C | T | 7065316 | C | T |
| 6595494 | C | T | 7075215 | C | T |
| 6604343 | C | T | 7098642 | C | T |
| 6615272 | C | T | 7099792 | C | T |
| 6617190 | G | A | 7100617 | C | T |
| 6619058 | C | T | 7101023 | C | T |
| 6622561 | G | A | 7103392 | C | T |
| 6629950 | C | T | 7104098 | C | T |
| 6632292 | C | T | 7109594 | C | T |
| 6656015 | C | T | 7110600 | C | T |
| 6669477 | G | A | 7110641 | C | T |
| 6690831 | C | T | 7112833 | C | T |
| 6690855 | G | A | 7116801 | C | T |
| 6696960 | G | A | 7135624 | G | A |
| 6705369 | G | A | 7135635 | G | A |
| 6716231 | G | A | 7146220 | G | A |
| 6729998 | G | A | 7160415 | C | T |
| 6734341 | C | T | 7161529 | G | A |
| 6758247 | G | A | 7162249 | G | A |
| 6759384 | C | T | 7165660 | C | T |
| 6767085 | G | A | 7176091 | G | A |
| 6769984 | C | T | 7177869 | G | A |
| 6780798 | A | G | 7185280 | G | A |
| 6801699 | G | A | 7186525 | C | T |
| 6805336 | G | A | 7211965 | G | G/C |
| 6805990 | G | A | 7211966 | A | A/T |
| 6808471 | C | T | 7211975 | C | C/T |
| 6818998 | G | A | 7211983 | G | G/T |
| 6830990 | G | A | 7211992 | G | G/T |
| 6843179 | C | T | 7211994 | G | G/A |
| 6847192 | G | A | 7212006 | T | T/C |
| 6854404 | C | T | 7212047 | C | C/G |

| Position in SEQ ID 16053 | Nucleotide in SEQ ID 16053 | Mutated Nucleotide |
|---|---|---|
| 7212067 | T | T/A |
| 7212068 | G | G/C |
| 7212075 | G | G/C |
| 7212088 | A | A/T |
| 7212097 | T | T/C |
| 7212113 | T | T/C |
| 7212121 | G | G/T |
| 7212122 | T | T/C |
| 7212142 | T | T/C |
| 7212144 | C | C/G |
| 7212151 | T | T/G |
| 7212156 | G | G/C |
| 7212180 | C | C/G |
| 7212182 | G | G/C |
| 7212183 | T | T/C |
| 7212206 | T | T/C |
| 7216330 | G | A |
| 7218939 | G | A |
| 7219494 | G | A |
| 7224067 | G | A |
| 7228023 | G | A |
| 7240925 | G | A |
| 7241497 | C | T |
| 7264121 | G | A |
| 7266647 | G | A |
| 7283171 | C | T |
| 7294161 | A | G |
| 7303836 | C | T |
| 7310019 | G | A |
| 7314132 | C | T |
| 7314146 | C | T |
| 7319151 | G | A |
| 7319658 | G | A |
| 7321495 | G | A |
| 7329181 | G | A |
| 7330808 | G | A |
| 7362245 | C | T |
| 7369374 | C | T |
| 7371536 | C | T |
| 7377855 | C | T |
| 7384932 | G | A |
| 7385124 | C | T |
| 7386113 | G | A |
| 7389303 | C | T |
| 7394213 | C | T |
| 7394997 | C | T |
| 7400636 | C | T |
| 7401592 | C | T |
| 7422484 | G | A |
| 7446288 | G | A |
| 7451085 | C | T |
| 7452627 | C | T |
| 7453489 | C | T |
| 7453910 | C | T |
| 7460642 | C | T |
| 7462223 | G | A |
| 7484067 | C | T |
| 7490770 | G | A |
| 7492384 | G | A |
| 7498836 | G | A |
| 7511194 | G | A |
| 7517188 | G | A |
| 7518982 | C | T |
| 7524203 | G | A |
| 7525798 | C | T |
| 7546077 | C | T |
| 7583090 | G | A |
| 7588792 | C | T |
| 7598819 | G | A |
| 7600514 | G | A |
| 7604996 | G | A |
| 7607903 | G | A |
| 7622689 | G | A |
| 7627683 | G | G/T |
| 7630530 | G | A |
| 7639840 | G | A |
| 7641043 | G | A |
| 7646004 | G | A |
| 7648704 | G | A |
| 7652691 | G | A |
| 7654254 | G | A |
| 7655513 | G | A |
| 7662521 | G | A |
| 7671626 | C | T |
| 7672126 | G | A |
| 7687061 | G | A |
| 7689723 | G | A |
| 7714246 | C | T |
| 7718521 | G | A |
| 7719226 | G | A |
| 7719430 | G | A |
| 7720998 | G | A |
| 7731353 | G | A |
| 7733376 | G | A |
| 7736672 | C | C/T |
| 7740086 | C | T |
| 7740896 | G | A |
| 7765137 | G | A |
| 7772239 | G | A |
| 7789263 | G | A |
| 7790304 | G | A |
| 7801751 | G | A |
| 7802623 | T | T/C |
| 7802638 | T | T/C |
| 7802639 | C | C/T |
| 7802682 | A | T |
| 7809752 | G | A |
| 7809834 | G | A |
| 7823754 | C | T |
| 7825882 | G | A |
| 7832540 | G | A |
| 7838339 | C | T |
| 7841392 | C | T |
| 7841997 | C | T |
| 7842274 | C | T |
| 7844241 | G | A |
| 7855301 | C | T |
| 7864327 | G | A |
| 7874843 | C | T |
| 7883195 | A | G |
| 7889441 | G | A |
| 7909245 | G | A |
| 7912017 | A | G |
| 7917279 | G | A |
| 7926998 | G | A |
| 7931764 | G | A |
| 7934819 | G | A |
| 7948630 | C | T |
| 7963950 | G | A |
| 7967045 | G | A |
| 7969374 | G | A |
| 7984213 | G | A |
| 7984254 | G | A |
| 7985275 | G | A |
| 8009877 | C | T |
| 8026754 | C | T |
| 8036245 | C | T |
| 8042744 | G | A |
| 8051051 | G | A |
| 8053700 | C | T |
| 8062905 | A | T |
| 8062911 | C | T |
| 8075410 | C | T |
| 8077440 | G | A |
| 8087405 | G | A |
| 8094018 | G | A |
| 8095401 | G | A |
| 8096270 | C | T |
| 8122172 | G | A |
| 8123295 | G | A |
| 8123721 | G | A |
| 8136640 | C | T |

-continued

| Position in SEQ ID 16053 | Nucleotide in SEQ ID 16053 | Mutated Nucleotide |
|---|---|---|
| 8161493 | C | T |
| 8165695 | A | A/T |
| 8165703 | A | A/G |
| 8165704 | C | C/G |
| 8167086 | G | A |
| 8171741 | G | A |
| 8179169 | G | A |
| 8181933 | G | A |
| 8186618 | C | T |
| 8193241 | C | T |
| 8195170 | C | T |
| 8195310 | C | T |
| 8199221 | G | A |
| 8202704 | C | C/T |
| 8205853 | G | A |
| 8212158 | C | T |
| 8212583 | G | A |
| 8214951 | C | T |
| 8221459 | G | A |
| 8227017 | G | A |
| 8233448 | C | T |
| 8237580 | G | A |
| 8239310 | G | A |
| 8240439 | G | A |
| 8241289 | G | A |
| 8243590 | G | A |
| 8247542 | G | A |
| 8248207 | C | T |
| 8256006 | G | A |
| 8263792 | G | A |
| 8267543 | G | A |
| 8272330 | G | A |
| 8273351 | C | T |
| 8278809 | G | A |
| 8282707 | G | A |
| 8298405 | T | T/A |
| 8298413 | C | C/G |
| 8302281 | G | A |
| 8311927 | T | C |
| 8323622 | C | T |
| 8325049 | G | G/C |
| 8325050 | A | G/A |
| 8325073 | C | C/G |
| 8325095 | G | G/C |
| 8325096 | G | G/T |
| 8325102 | C | C/G |
| 8325109 | T | C/T |
| 8325115 | C | G/C |
| 8325118 | C | C/G |
| 8325121 | G | G/C |
| 8325127 | G | G/C |
| 8325133 | C | G/C |
| 8325203 | T | T/C |
| 8325210 | A | G/A |
| 8325277 | C | C/G |
| 8325286 | C | C/G |
| 8349257 | G | A |
| 8351616 | G | A |
| 8355565 | C | T |
| 8355924 | C | T |
| 8363036 | G | A |
| 8364757 | C | T |
| 8365293 | G | A |
| 8368404 | G | A |
| 8378911 | G | A |
| 8379977 | G | A |
| 8380006 | C | T |
| 8381094 | G | A |
| 8384806 | G | A |
| 8389000 | C | T |
| 8389283 | A | G |
| 8393915 | G | A |
| 8396831 | G | A |
| 8397563 | G | A |
| 8402662 | G | A |
| 8411820 | C | T |

-continued

| Position in SEQ ID 16053 | Nucleotide in SEQ ID 16053 | Mutated Nucleotide |
|---|---|---|
| 8413318 | C | T |
| 8414872 | C | T |
| 8431655 | T | T/A |
| 8441210 | C | T |
| 8449495 | G | G/A |
| 8453858 | G | A |
| 8463714 | G | A |
| 8466767 | G | A |
| 8491536 | G | A |
| 8497636 | C | T |
| 8506267 | G | A |
| 8509227 | G | A |
| 8515828 | G | A |
| 8529144 | G | A |
| 8544731 | G | A |
| 8546526 | C | T |
| 8556565 | G | A |
| 8559522 | G | A |
| 8560241 | C | T |
| 8567608 | C | T |
| 8572238 | C | T |
| 8576774 | G | A |
| 8582623 | C | T |
| 8589455 | C | T |
| 8589459 | C | T |
| 8595339 | C | T |
| 8610015 | C | T |
| 8622039 | C | T |
| 8631175 | G | A |
| 8640526 | C | T |
| 8646416 | G | A |
| 8647802 | G | A |
| 8648408 | G | A |
| 8655581 | C | T |
| 8658688 | G | A |
| 8668191 | C | T |
| 8668196 | G | A |
| 8669919 | G | A |
| 8674137 | C | T |
| 8678961 | G | A |
| 8682722 | G | A |
| 8690364 | C | T |
| 8691972 | C | T |
| 8699652 | G | A |
| 8699708 | G | A |
| 8709561 | C | T |
| 8720459 | G | A |
| 8731485 | G | A |
| 8737851 | G | A |
| 8737859 | G | A |
| 8742265 | C | T |
| 8743148 | C | T |
| 8754468 | G | A |
| 8754501 | G | A |
| 8759529 | G | A |
| 8761290 | C | T |
| 8769464 | T | C |
| 8792629 | G | A |
| 8793001 | C | T |
| 8809351 | C | T |
| 8813761 | C | T |
| 8813866 | C | T |
| 8816396 | G | A |
| 8821923 | G | A |
| 8825490 | G | A |
| 8828064 | C | T |
| 8841828 | G | A |
| 8842797 | G | A |
| 8843541 | G | A |
| 8845199 | T | C |
| 8848419 | G | A |
| 8849052 | G | A |
| 8854017 | C | T |
| 8854256 | G | A |
| 8858030 | G | A |
| 8859328 | G | A |

-continued

| Position in SEQ ID 16053 | Nucleotide in SEQ ID 16053 | Mutated Nucleotide |
|---|---|---|
| 8860995 | G | A |
| 8861382 | G | A |
| 8871894 | C | T |
| 8872344 | C | C/T |
| 8875526 | G | A |
| 8881555 | G | A |
| 8889242 | Ci | A |
| 8893686 | G | A |
| 8894581 | G | A |
| 8896018 | G | A |
| 8901982 | G | A |
| 8902511 | G | A |
| 8902844 | G | A |
| 8902903 | G | A |
| 8907784 | G | A |
| 8927137 | G | A |
| 8929703 | G | A |
| 8931762 | C | A |
| 8934108 | G | A |
| 8937518 | C | T |
| 8943513 | C | T |
| 8943676 | C | T |
| 8944024 | C | T |
| 8945415 | C | T |
| 8946251 | C | T |
| 8948806 | G | A |
| 8950622 | C | T |
| 8951908 | C | T |
| 8953417 | G | A |
| 8955117 | G | A |
| 8956021 | C | T |
| 8956608 | C | T |
| 8958843 | C | T |
| 8959688 | G | A |

-continued

| Position in SEQ ID 16053 | Nucleotide in SEQ ID 16053 | Mutated Nucleotide |
|---|---|---|
| 8974326 | G | A |
| 8979884 | C | T |
| 8982938 | G | G/C |
| 8982956 | G | G/C |
| 8982975 | G | G/C |
| 8983002 | G | G/A |
| 8983053 | C | C/T |
| 8983087 | G | A/G |
| 8983088 | G | G/C |
| 8983102 | A | G/A |
| 8983134 | G | G/C |
| 9008254 | C | T |
| 9028349 | G | A |
| 9029056 | C | T |
| 9045846 | G | A |
| 9049564 | C | T |
| 9052240 | C | T |
| 9052265 | G | A |
| 9053107 | G | A |
| 9058239 | G | A |
| 9060181 | C | T |
| 9064090 | C | T |
| 9072129 | C | C/T. |

2. A microorganism comprising the DNA of claim 1, wherein said microorganism is *Actinoplanes utahensis*.

3. A method for producing Acarbose comprising the steps:
   a) cultivating the microorganism of claim 2 to produce Acarbose; and
   b) harvesting said Acarbose produced by the microorganism.

* * * * *